(12) United States Patent
Mills

(10) Patent No.: US 7,608,045 B2
(45) Date of Patent: Oct. 27, 2009

(54) METHOD FOR NONINVASIVE CONTINUOUS DETERMINATION OF PHYSIOLOGIC CHARACTERISTICS

(75) Inventor: Alexander K. Mills, San Antonio, TX (US)

(73) Assignee: Woolsthorpe LLC, Brentwood, TN (US)

( * ) Notice: Subject to any disclaimer, the term of this patent is extended or adjusted under 35 U.S.C. 154(b) by 995 days.

(21) Appl. No.: 10/912,721

(22) Filed: Aug. 4, 2004

(65) Prior Publication Data

US 2005/0177046 A1 Aug. 11, 2005

Related U.S. Application Data

(62) Division of application No. 10/008,245, filed on Nov. 7, 2001, now Pat. No. 6,819,950.

(51) Int. Cl.
*A61B 5/00* (2006.01)

(52) U.S. Cl. ................ 600/500; 600/485; 600/526

(58) Field of Classification Search ............... None
See application file for complete search history.

(56) References Cited

U.S. PATENT DOCUMENTS 6,120,456 A * 9/2000 Oka et al. ............... 600/485
6,122,536 A * 9/2000 Sun et al. ............... 600/341

* cited by examiner

*Primary Examiner*—Robert L Nasser
(74) *Attorney, Agent, or Firm*—Francis Law Group

(57) ABSTRACT

The invention comprises methods for noninvasively monitoring physiological characteristics of a patient's blood. Determinations of blood constituent concentrations may be made by comparing absorbance of radiation at varying parameters, such as path length and blood pressure. Preferably, changes in pressure are effected by changing the height of the probes relative to the patient's heart. Determinations of blood pH may be made by comparing absorbance of the blood at different wavelengths. The temperature of the blood, and thus of the patient's core, may also be accurately determined. Further, cardiac output characteristics and blood pressures may be noninvasively determined using the methods of the invention.

10 Claims, 27 Drawing Sheets

```
Computational Algorithm for Determination of Hemoglobin Concentration
C      A   is the measured absorbance
C      A1  is the absorbance after dividing out extinction coefficients
C          and correcting for saturation
C      A2,A3, ... will be the absorbances at different path lengths,
C          created by multiplying by constants
C      A1,A3, ... and L2,L3, etc.
          constant M2=0.9
          constant M3=0.8
          constant M4=0.7
          constant M5=0.6
          constant M6=0.5
          constant M7=0.4
          constant M8=0.3
C
C      read in the value for hemoglobin absorbance and a value k
C      representing the extinction coefficient for the wavelength and
C      the oxygen saturation
          Begin
          Read, A
          Read, k
          A1:=A/k
          A2:=A1*M2
          A3:=A1*M3
          A4:=A1*M4
          A5:=A1*M5
          A6:=A1*M6
          A7:=A1*M7
          A8:=A1*M8
C
          k1234 = log(A1) * log(A2) - log(A3) * log(A4)
          k5678 + log(A5) * log(A6) - log(A7) * log(A8)
          kd:=[ log(A1*A2) - log(A3*A4) ] / [ log(A5*A6) - log(A7*A8) ]
C
C      combine all the A terms that occur as coefficients,
          kAc := log(A2/A1) - log(A3/A1) - log(A4/A1) - [(kd * log(A5/A1)] -
               - [kd * log(A6/A1) + [kd * log(A7/A1)] + [kd * log(A8/A1)]
C
C      combine all the A terms that occur alone
          kAa :=- [log(A3/A1) * log(A4/A1)] ) -
               - kd * [log(A5/A1) * log(A6/A1)] +
               + kd* [(log(A7/A1) * log(A8/A1)]
C
C      k1234 - ( kd * k5678 ) = klg(L) * kAc + kAa
C      log(L) = [k1234 - (kd * k5678) - kAa] / kAc
C      L = antilog{[k1234-(kd * k5678) - kAa] / kAc}
C      use EXP or antilog function
          L = EXP([k1234 - (kd * k5678) - kAa] / kAc)
C      L is the path length
C      C is the concentration of hemoglobin
          C = A1 / L
C
          END
```

FIG.-33

METHOD FOR NONINVASIVE CONTINUOUS DETERMINATION OF PHYSIOLOGIC CHARACTERISTICS

CROSS-REFERENCE TO RELATED APPLICATIONS

This Application is a division of application Ser. No. 10/008,245 filed Nov. 7, 2001 now U.S. Pat. No. 6,819,950.

FIELD OF THE INVENTION

The present invention relates generally to noninvasive methods of quantitatively determining various physiologic parameters relating to cardiovascular and respiratory function. More particularly, the invention relates to methods and devices for continuous, noninvasive determination of: hemoglobin, glucose and other blood constituent concentrations, blood pH and acid-base balance, blood flow differentials, blood temperature, arterial blood pressure, venous pressure, arterial oxygen saturation, venous oxygen saturation, arterial pulse wave velocity, aortic pulse wave velocity, aortic pulse flow velocity, cardiac stroke volume, cardiac index, cardiac output, heart rate, respiratory rate and cardiac ejection fraction.

BACKGROUND OF THE INVENTION

Critically ill and seriously injured patients require constant care and attention. Doctors, nurses, and hospital technicians need a continuous flow of information about the many patients under their care. Heart rate and blood pressure measurements are two primary vital signs that indicate the health of patients under their care. When these two common indices of wellness fall below normal readings, a patient is usually in distress and requires immediate attention.

Dangerous conditions brought about by a cardio-vascular or pulmonary disease, severe trauma, or drug abuse may bring about a failure of the lungs and heart to supply the bloodstream with life-giving oxygen. Such a fatal deficiency can be detected by continually gauging the amount of hemoglobin in the bloodstream that is carrying oxygen. This third vital sign, which manifests oxygen saturation of the blood, is especially critical because a rapid decline in oxygen in the bloodstream is associated with increased risk of patient mortality.

It is well known that blood pressure can be directly measured by placing a fluid-filled catheter directly into the vessel and coupling this to an electromechanical transducer. This is the most accurate means, but has all the disadvantages of invasive measurement, including pain on insertion, risk of infection or disease transmission, risk of bleeding or thrombosis, and great expense. A further disadvantage is the creation of toxic medical waste (needle, gloves, skin dressing, etc).

Blood pressure measurement can also be measured indirectly using an occlusive cuff (with either auscultation or oscillometry to make the determination). This is the most common means of blood pressure measurement. Illustrative is U.S. Pat. Nos. 5,582,179, 5,048,533, 5,152,296 and 4,793,360.

A further occlusive cuff apparatus is disclosed in U.S. Pat. No. 5,766,130. According to the invention, the apparatus includes multiple "pressurized pneumatic cuffs" that are used to "plot blood pressure and/or volumetric blood flow wave forms from a plurality of separate digits and/or extremities of a patient so that circulatory parameters may be measured rapidly and recorded from a great number of the patient's digits or limbs".

Although commonly employed, the occlusive cuff also has numerous disadvantages, which include discomfort, intermittent readings, and poor reliability.

An additional means of determining blood pressure is through an assessment of "pulse wave velocity". Several prior art references disclose methods and/or apparatus employing such means. Illustrative is U.S. Pat. No. 5,649,543.

There are also several prior art references that disclose methods and/or apparatus for determining blood pressure through a "pulse wave amplitude" assessment. Illustrative are U.S. Pat. Nos. 4,735,213, 4,872,461, 4,793,360, 5,265,011, 5,385,149, 5,511,303, 5,582,179, 5,680,867 and 5,882,311.

Additional physiologic characteristics such as blood temperature and pH provide further information regarding the status of the patient. Moreover, combinations of measurements can be used to determine specific cardio-pulmonary parameters.

Acid-base balance (the most common measure is pH) is perhaps the most important factor in the chemistry of both biologic and non-biologic systems. It figures in speed of reactions; indeed, if a reaction will occur at all. In most biologic systems, determination of pH requires laboratory analysis. The monetary costs are high, and procedures involve risk for patient subject and laboratory technicians among others. Toxic medical waste (syringes, gloves, etc.) is created and must be disposed of safely. In other systems (and to some extent in biologic systems), pH measurement is done in one of two common ways: colorimetric and electrochemical. Noninvasive measurement of arterial blood pH is described in U.S. Pat. No. 5,978,691.

Although most of the noted noninvasive monitoring methods and apparatus, particularly the occlusive cuff, have been employed for many years by health care personnel, the conventional methods and apparatus have one major, common drawback—the need for separate calibration.

Accordingly, there is a need for noninvasive methods and devices capable of continuously determining various physiological characteristics, such as blood pressure, central venous pressure and cardiac output, without separate calibration. There is also a similar need for noninvasive methods and devices for determining various blood parameters including hemoglobin, glucose and other blood constituent concentrations, blood pH and acid-base balance, blood flow differentials, blood temperature, blood pressures and pressure wave differentials. As will be appreciated by one having ordinary skill in the art, the present invention satisfies these and other needs.

SUMMARY OF THE INVENTION

The invention comprises methods for noninvasively determining the concentration of a blood constituent, generally including the steps of providing a tissue probe having a radiation emitter with a wavelength and a detector configured to receive the wavelength after absorbance through a path length of the patient's blood; measuring absorbance of the patient's blood by emitting and detecting radiation after passage through the patient's blood; varying the path length of to provide multiples of path length; measuring absorbance of the patient's blood at each multiple of the path length; and determining the concentration of the blood constituent based upon the changing absorbance. Preferably, the determination is made continuously. The determination can also be made using calculated multiples of the path length.

Alternatively, the invention comprises the steps of providing a first and second tissue probe each having a radiation emitter with a wavelength and a radiation detector configured to receive the wavelength after absorbance through a path length of the patient's blood at a position relative to the heart of the patient; measuring absorbance of the patient's blood by emitting radiation and detecting radiation after passage through a first path length of the patient's blood; varying the pressure of the blood within the first and second probes; measuring absorbance of the blood as the pressure is varied; and computing the time of arrival and amplitude of the pulse based on the absorbance at the varying pressures. Preferably, the pressure of the blood within the probes can be varied by changing the hydrostatic pressure relative to the heart such as by changing the height of the probe.

These techniques can be applied to arterial or venous blood. Preferably, the blood constituent being measured comprises hemoglobin. By measuring hemoglobin oxygen saturation or blood pH at different probe locations, blood corresponding to a single flow wave can be identified. By comparing the timing of the flow wave arrival at the different probe locations, multiple determinations of cardiac characteristics can be made, including arterial pulse wave velocity, aortic pulse wave velocity, aortic pulse flow velocity, cardiac stroke volume, cardiac index, cardiac output, heart rate, respiratory rate and cardiac ejection fraction. In other embodiments, tissue probes having more than one radiation emitter and detector pairs can be employed.

The invention also comprises methods for noninvasively determining the pH of blood of a patient, generally including the steps of providing a first tissue probe having a first and second radiation emitter with a first and second wavelength, respectively, and a first and second radiation detector configured to receive the first and second wavelength, respectively, after absorbance through the patient's blood; measuring absorbance of the patient's blood by emitting radiation at the first and second wavelength through the patient's blood and detecting the radiation after passage through the patient's blood; and computing the pH of the blood based upon the measured absorbance at the first and second wavelengths. The first and second wavelengths are selected so that the absorbance of the first wavelength depends upon the pH of the blood and the absorbance of the second wavelength is substantially independent of the pH of the blood. Preferably, the method is tailored to measuring the absorbance spectrum of hemoglobin species that have certain pH dependent absorption peaks. Since pH is also dependant upon temperature, more accurate results can be obtained if the blood temperature is varied. Alternatively, if the pH of the blood is characterized, the temperature of the blood can accurately be determined.

Yet another embodiment of the invention is a method for non-invasively determining the concentration of a blood constituent comprising the steps of measuring absorbance of arterial and venous blood; determining arterial and venous oxygen saturation; subtracting hemoglobin absorbance based upon the arterial and venous saturation; and determining the concentration of a blood constituent based upon remaining absorbance. Preferably, the blood constituent comprises glucose.

The invention also includes a device for the noninvasive monitoring of a physiologic characteristic of a patient's blood. In one embodiment, the device comprises a tissue probe having a radiation emitter and a radiation detector configured to receive the radiation after absorbance through the patient's blood; a position sensor for determining the relative height of the probe compared to a level corresponding to the patient's heart; and a controller for computing the physiologic characteristic of the patient's blood based on the absorbance of the first wavelength of radiation and the relative height of the probe. The radiation emitters of the invention can utilize a single wavelength or a plurality of discrete wavelengths and may include visible light, infrared light, and ultraviolet light. The probes are adapted for use with hands, fingers, feet, toes, ears, earlobes, nares, lips, tongue and the like. Additional radiation emitters and detectors may also be used. Preferably, the probe further comprises ECG leads.

An alternative embodiment of the device of the invention comprises a tissue probe and controller in conjunction with a movement generator for inducing a position change of the probe with respect to a level corresponding to the patient's heart. Preferably, the movement generator induces a known position change of the probe and moves the probe to positions above and below a level corresponding to the patient's heart.

The invention also comprises methods for determining other physiological characteristics of a patient's blood noninvasively. In one embodiment, absorbance characteristics of the blood are measured at varying positions relatively to the level of the patient's heart. By comparing blood parameters such as pulse amplitude, pulse velocity, pulse delay, pulse contour, flow velocity and flow delay to hydrostatic pressure differences induced by the position changes, characteristics such as arterial and central venous blood pressure and cardiac output can be determined. Alternatively, two probes are used to compute pulse delays between coupled tissues or opposing tissues.

The subject invention relates novel methods for noninvasive determination of physiologic characteristics. The first new and unique method and device utilizes changes in hydrostatic pressure induced by positional changes to facilitate measurements. A second new and unique method and device for noninvasive determination of cardiac output by measuring delays in pulse arrival times in coupled organs or members on opposite sides of the body is also described. The two methods are such that they can advantageously be used together.

By varying the hydrostatic pressure in an extremity, one can not only perform self-calibration for a blood pressure determination, but also change the pulse wave velocity and pulse propagation delay with respect to the opposite extremity. With this information, pulse wave velocity, and consequently flow wave velocity at the aortic root can be determined.

Similar techniques of varying hydrostatic pressure can be used to assess venous pressure and saturation. The technique of repetitious determinations made while altering position or other variables allows a multitude of additional analyses to be made. The determinations can be made intermittently or continuously.

Further objects of the invention are exemplified by the following potential applications:

(A-1). A patient is anesthetized for a surgical procedure. Probes are attached to the index fingers of each hand, and a movement generator is placed on one arm. A complete set of vital signs and physiologic characteristics is generated continuously, including: arterial blood pressure, venous pressure, arterial oxygen saturation, venous oxygen saturation, arterial pulse wave velocity, aortic pulse wave velocity, aortic pulse flow velocity, cardiac stroke volume, cardiac output, heart rate, and respiratory rate. Other characteristics can be calculated if desired.

(A-2). A patient is anesthetized for a cardiac surgical procedure. As access to the arms is difficult, probes are attached to the patient's temples. A complete set of vital signs and physiologic characteristics is continuously generated.

(A-3). A patient is anesthetized for a cardiac surgical procedure; this time the procedure includes valvular repair or replacement. Since the cardiac output and other characteristics can be continuously computed, the adequacy of the surgical repair can be judged immediately.

(A4). As the number of endoscopic or minimally invasive cardiac surgical procedures is expected to increase, the demand for less invasive monitoring will also increase. The device described herein provides noninvasive, continuous monitoring of essentially all cardiovascular characteristics.

(A-5). Cardiac catheterization procedures are often done on critically ill patients. As the procedures are usually relatively brief and accomplished without general anesthesia, invasive monitoring methods are often not desired despite the illness of the patients. The device described herein will provide the necessary monitoring that is typically provided by much more invasive, expensive, and time consuming monitors (A-6). A patient is hospitalized in the intensive care unit of a hospital after a heart attack. Probes are attached to the index fingers of each hand, and a movement generator is placed on an arm or a leg. A complete set of vital signs and physiologic characteristics can be continuously generated. In addition, arrhythmias can be detected and diagnosed.

(A-7). The patient noted above is now moved to a "step-down" or telemetry unit from the intensive care unit. Because the device described herein eliminates the need for invasive monitoring lines, a complete set of vital signs and physiologic characteristics can still be continuously generated. As the patient has mobility of arms and legs, a movement generator is no longer needed, as the patient's spontaneous motion, even during sleep, will generate hydrostatic pressures in the limbs, allowing all computations to be made. In addition, the probes may be made wireless, and connected to a central nursing station by means of infrared or radio frequency communication.

(A-8). The patient noted in applications 6 and 7 above is now moved to a regular hospital bed, and does not require continuous monitoring. However, vital signs can still be recorded by a technician moving the device from bedside to bedside on a cart. The device does not require highly trained nursing personnel to operate.

(A-9). The patient noted in applications 6, 7, and 8 above has now been discharged from the hospital, and now presents to his physician's office for follow-up. The same device can be used in physician's offices, as it provides better care at lower cost.

(A-10). Ambulances, emergency vehicles, and military vehicles can also employ this device as it is very simple to operate, and provides data that currently is impossible for them to obtain. In addition, the information can be transmitted to central stations where medical personnel are available for help and advice.

(A-11). The device and methods of the invention will provide means of monitoring patients or checking vital signs for extended care facilities, nursing homes, and other health-related facilities (A-12). Blood pressure screening clinics and drugstores will have a greatly improved means of determining patient's blood pressures and other vital signs. Airports and airplanes are able to purchase medical equipment, but often do not have personnel trained to operate the equipment. The device is simple and quick to operate.

(A-13). The patient noted in applications 6 through 9 above can also monitor his heart disease and health care at home. The operation of the device is straightforward enough to be used by the layman with minimal instruction, and inexpensive enough for personal home use. The patient can measure his cardiovascular characteristics daily, or as frequently as he and his physician desire. A communication means, such as a modem, can easily be incorporated into the device. This, with appropriate software and support, would allow essentially instantaneous communication with a physician's office, clinic, or hospital. In addition, a permanent record can be made and stored electronically. If desired, the device could automatically "sign on" to the Internet or other network, and link to the appropriate website or other address. The ability to participate more fully in their own health care will improve the welfare of individuals.

(A-14) The patient of above presents to the emergency room of a hospital with chest pain. The ER physician can access, via the Internet or other means, the patient's vital sign history, including ECG. This allows the physician to determine if abnormalities are new or chronic. Changes, such as dysrhythmias, can be identified as to when they first occurred, perhaps to within a time frame of hours or less.

(A-15). People without diagnosed cardiovascular disease can use the device to allow themselves to participate in their own health care. This will allow virtually immediate diagnosis of any problems, allowing early intervention. In addition, a permanent record can be created if desired.

(A-16). The device will impact fitness and physical training for everyone from lay people to military personnel to professional athletes.

(A-17). The device can be employed in the diagnosis and management of peripheral vascular disease. Measurement of pulse wave velocity in the extremities, and particular differential pulse wave velocities in the lower extremities, can be used to diagnose peripheral vascular disease. Since measurements are real time and continuous, they can also be used in management. For example, if balloon angioplasty of an artery is performed, the clinician can tell immediately if flow has improved. In the case of angioplasty of coronary arteries, the clinician can follow cardiac characteristics on a beat-by-beat basis.

(A-18). In addition to peripheral vascular disease, other diseases, such as abdominal aortic aneurysm, can be diagnosed and managed. Changes in pulse wave velocity and waveform can be followed for years if desired.

(A-19). Some of the most important potential uses of the device relate to the health care of neonates and young children. For these patients, the measurement of common characteristics such as blood pressure can be difficult even for highly trained personnel in well-equipped facilities. The simple placement of probes on fingers will alleviate this. The device will also allow noninvasive diagnosis of congenital cardiac defects and anomalies. Analysis of differential pulse wave velocity and blood pressure will allow rapid, accurate, and specific diagnosis of many disorders, including Tetralogy of Fallot and transposition of the great vessels. The ability to distinguish both arterial and venous saturations and pressures will allow diagnosis of patent ductus arteriosus, truncus arteriosus, atrial septal defect, and ventricular septal defect. Differential arm and leg pulse wave velocities and pressures will confirm diagnosis of coarctation of the aorta. Because of its continuous measurements, the device can be used for only for diagnosis but confirmation of adequacy of repair, including intraoperatively. As the device is inexpensive and easy to operate, it may become a screening tool for newborns and infants.

(A-20). The device can be used in conjunction with intra-aortic balloon pump (IABP) counterpulsation. Beat-by-beat analysis of effectiveness and ability to wean from counterpulsation can be made.

(A-21). The device can be used in conjunction with placement of cardiac pacemakers, to set proper rate and timing intervals. In addition, efficacy of pacemakers can be checked as frequently as desired, and scheduling of reprogramming or replacement made automatically.

(A-22). It is straightforward to incorporate other devices, such as the electroencephalogram (EEG) or electromyogram (EMG), into probes of the invention. As a general-purpose monitor, the device will invite the addition of specialized add-ons.

(A-23). Many enhancements are included in the invention. For example, addition of chest (horizontal) leads allows full diagnostic ECGs to be performed.

(A-24). Under some circumstances, such as severe hypotension, the pulse cannot be identified in the periphery. In such cases, many of the determinations claimed herein cannot be made. However, the ability of the device to identify venous blood can still give important information.

(A-25). Forces other than gravity can be used. In a microgravity environment such as a space station orbiting the Earth, a device such as the one described could be constructed to perform all indicated determinations using acceleration caused by movement in place of gravitational acceleration.

(A-26). As mentioned in the examples above, an anticipated use is in the field of home health care, with the possibility of automatic sign-on and direction to a website. As the user is already participating in his or her health care, the extension of providing access to related health or other information via the Internet® is a natural one.

(A-27). A verification means, such as fingerprint scanning, can be incorporated into a personal-use device, to ensure that any medical information gathered belonged to the individual using the device.

(A-28). The device will be used in conjunction with the Penaz technique or other methods, such as calibration with a cuff or other means, as desired.

(A-29). Nerve blocks, such as spinal or epidural anesthesia, block the actions of the sympathetic nervous system, producing both arterial and venous dilation. This device can be used to assess these effects.

(A-30). A patient with suspected peripheral vascular disease of the lower extremities is tested. A probe of the invention is placed on a toe of one foot, and an identical probe is placed on a toe of the other foot. Pulse velocities and possible pulse delay between the two extremities are measured.

(A-31). The patient from application 30 is tested further. Another identical probe is placed on a finger. Pulse velocities and possible pulse delay between the two lower extremities are measured. In addition, comparison is made with pulse velocity and propagation time in the upper extremity.

(A-32). The patient from applications 30 and 31 is tested further. This time, the legs are raised and lowered to gain further information on pulse velocities and propagation times.

(A-33). A person suffers severe trauma to the lower extremities in a motor vehicle accident. His physicians are concerned about the possibility of his developing "compartment syndrome", which is compromise of blood supply due to swelling of injured tissues. Probes of the invention are placed on his feet to monitor the integrity of the vascular supply.

(A-34). A pharmaceutical company develops a new drug to manage hypertension, CHF, arrhythmias. Instead of long trials or invasive trials, they are conducted on subjects using this device.

(A-35). Taking vital signs on a space station. The techniques described herein lend themselves well to the special problems of this unique environment.

BRIEF DESCRIPTION OF THE FIGURES

Further features and advantages will become apparent from the following and more particular description of the preferred embodiments of the invention, as illustrated in the accompanying drawings, and in which like referenced characters generally refer to the same parts or elements throughout the views, and in which:

FIG. 33 is a computer algorithm for determining hemoglobin concentration, according to the invention;

DETAILED DESCRIPTION OF THE INVENTION

Functionally the heart is divided into two sides or sections. The right or pulmonary circulation section that receives blood from the veins of the body and pumps it through the lungs and the left or systemic circulation section that receives the blood from the lungs and pumps it to the body. The blood is then collected in the veins to be returned to the right side of the heart.

Figure 1:
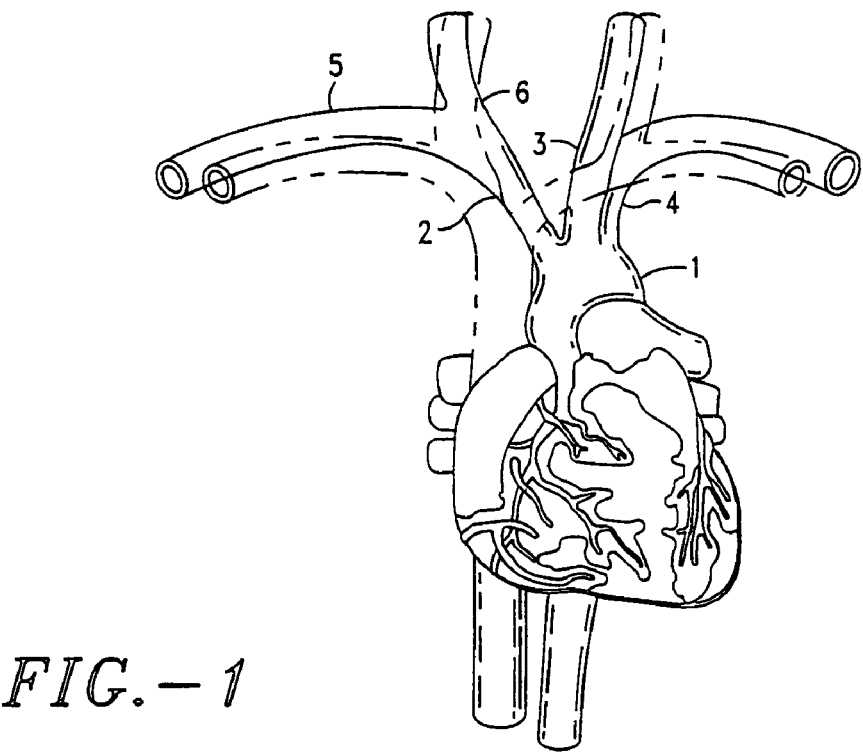
FIG. 1 is a diagram of the central cardiovascular system, showing the asymmetry of origins of the vessels off the aortic arch.

Referring to FIG. 1, the arterial system begins at the aorta 1, to which the left ventricle of the heart pumps. The first three branches of the aorta are the brachiocephalic or innominate artery 2, the left (common) carotid artery 3, and the left subclavian artery 4. The brachiocephalic artery branches into the right subclavian 5 and right (common) 6 carotid arteries. These arteries provide the blood supply for the head and upper extremities. The aorta then passes down (caudal) through the body, continuing to provide arterial branches to organs, terminating as a bifurcation creating the iliac arteries. The brachiocephalic or innominate artery is the first branch of the aorta. It in turn branches into the right subclavian and right carotid arteries. In contrast, the left subclavian and left carotid arteries originate directly off the aortic arch. Thus, the subclavian and carotid arteries and any of their branches to one side of the body have different paths from their counterparts on the opposite side of the body.

Because of the different origins from the aorta and different branching pattern of the arterial tree, it can be appreciated that blood ejected from the left ventricle will not follow symmetrical pathways to opposite arms or body or opposite sides of the head. Similarly, the pressure pulse wave associated with left ventricular ejection will follow different pathways, and can be expected to arrive at different times for paired organs or members of the upper body, or members of the upper body compared to the lower body.

Measurements performed by the inventor have shown this delay can range from less than one millisecond to several milliseconds, depending on the subject and circumstances. In addition, the inventor has found that this delay can be altered by several methods disclosed herein. This propagation delay, its alterations, and other factors make possible several determinations heretofore not possible by noninvasive means.

Blood pressure is the pressure exerted by the blood within a vessel upon the wall of the vessel. It is measured in units of force per unit area. Central venous pressure is the pressure within the large veins in the chest and the right atrium, which is the common emptying point for the venous system. Cardiac output is the amount of blood pumped by the heart, expressed in units of volume per time.

Central venous pressure (CVP) is defined as the distending pressure present in the veins in the chest (proximate to the heart), and is considered equal to the pressure in the right atrium (which is the emptying point for the venous system). Pressure should be the same throughout the venous system, but there are valves to ensure that the blood does flow back toward the heart (for example, when standing the venous blood must flow uphill, and there is no pump as on the arterial side).

As discussed in detail below, the present invention generally includes a radiation emitter having at least one wavelength being applied through a patient's tissue to the patient's blood; a radiation detector which detects reception of the at least one wavelength after absorbance through the blood, a movement generator for inducing position changes in the tissue; and a controller for computing the various characteristics based on the absorbance of the at least one wavelength of radiation at various position levels. In a preferred embodiment, the radiation emitter and detector are inserted in a probe which can be placed about the tissue/blood to be measured. A number of suitable configurations for probes are shown in FIGS. 2-8 and disclosed in Co-Pending application Ser. No. 09/684,104, which is incorporated by reference herein.

Figure 2:
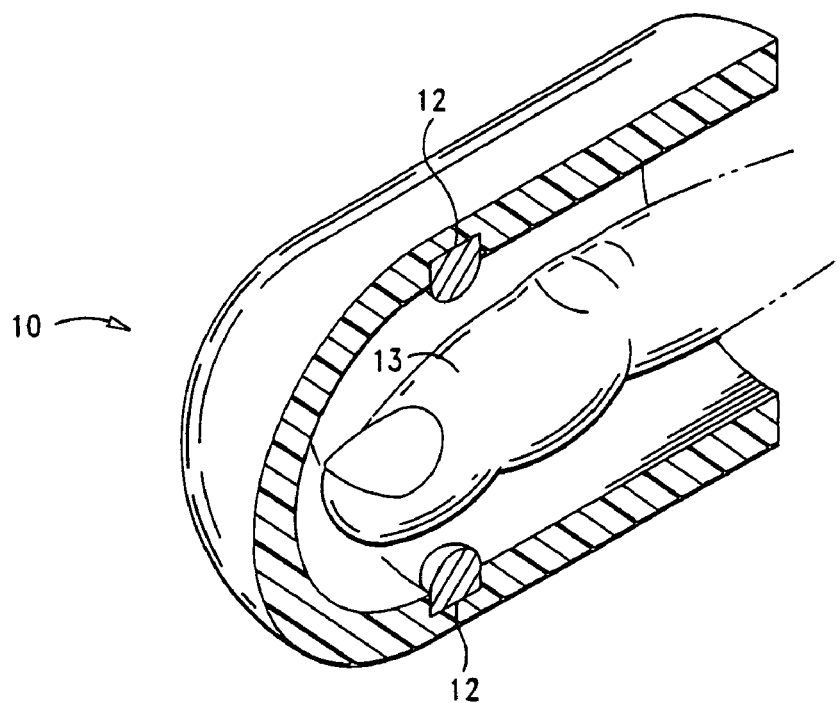
FIG. 2 is a partial perspective view of one embodiment of a physiologic "tissue" probe with a single emitter-detector pair, according to the invention.
Figure 3:
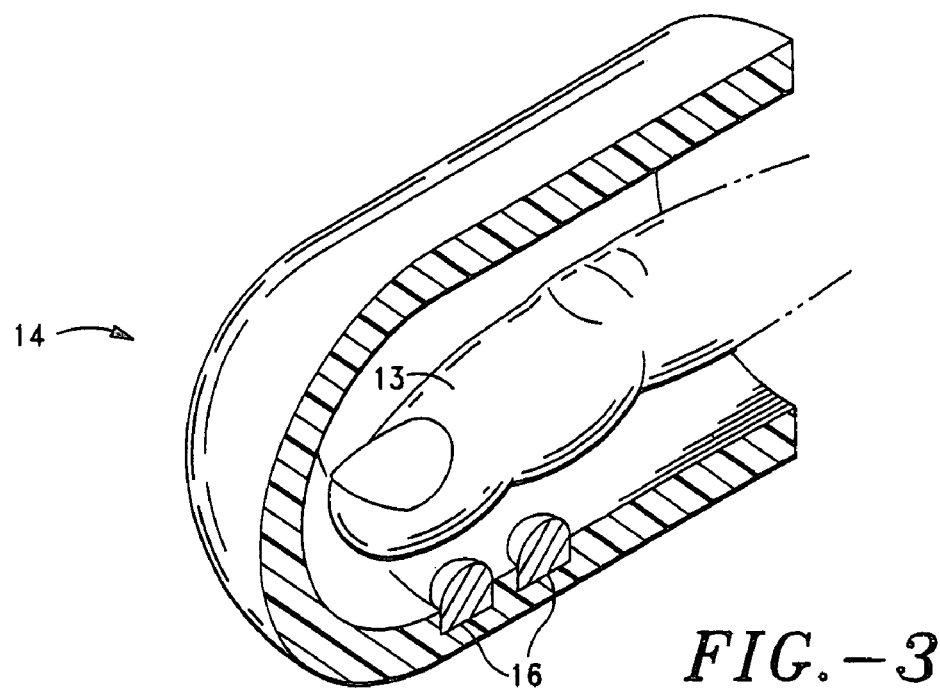
FIG. 3 is a partial perspective view of an alternative embodiment of a tissue probe with a single emitter-detector pair, according to the invention.
Figure 4:
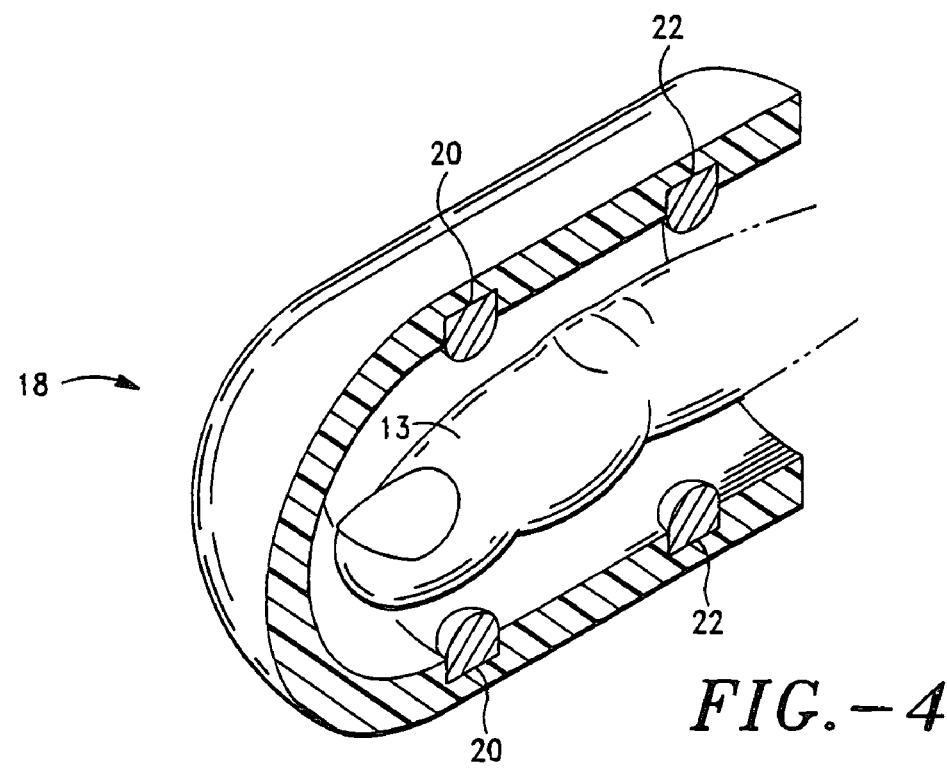
FIG. 4 is a partial perspective view of an alternative embodiment of a tissue probe with two emitter-detectors, according to the invention.

For example, FIG. 2 shows a representative probe 10 with a single emitter-detector pair 12. The emitter and detector are placed such that transmittance through a body member, such as a finger 13, is measured. Generally, any part of the body that can be successfully transilluminated with the radiant energy used can be utilized. Thus, toes, ears, etc. could also be used. In addition, pulse oximetry can be accomplished with this and all of the following embodiments. FIG. 3 shows a representative probe 14 with a single emitter-detector pair 16 placed such that reflectance of a body member, such as a finger, is measured. Further, FIG. 4 shows a probe 18 with two emitter-detector pairs 20 and 22 spaced a known distance apart. This can be used to measure the velocity of the pulse wave within the probe itself.

Figure 5:
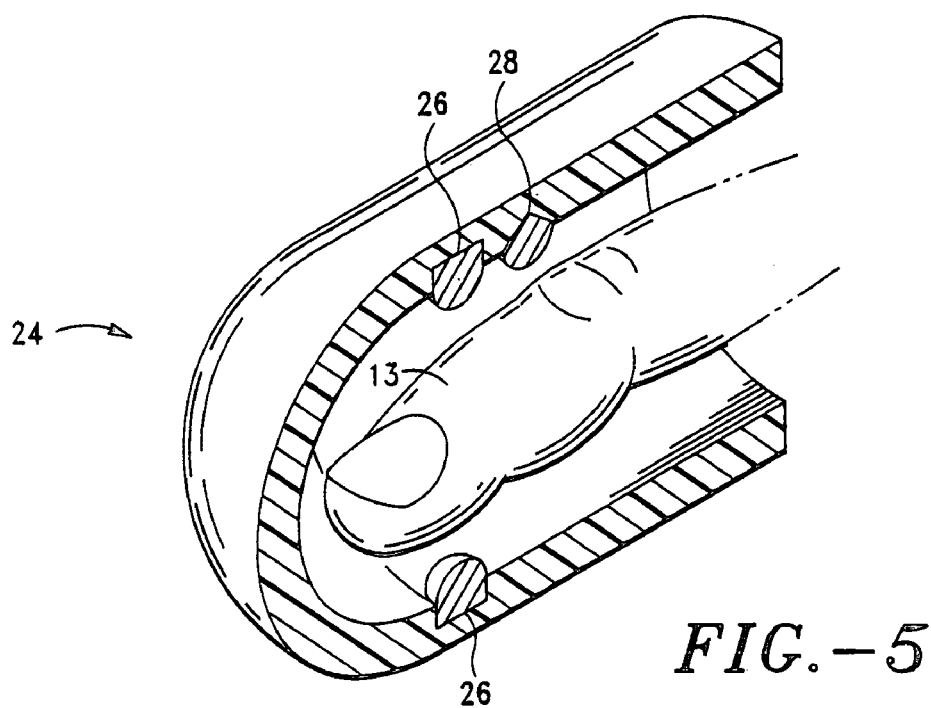
FIG. 5 is a partial perspective view of an alternative embodiment of a tissue probe with a single emitter-detector pair and a single electrocardiogram (ECG) electrode, according to the invention.
Figure 6:
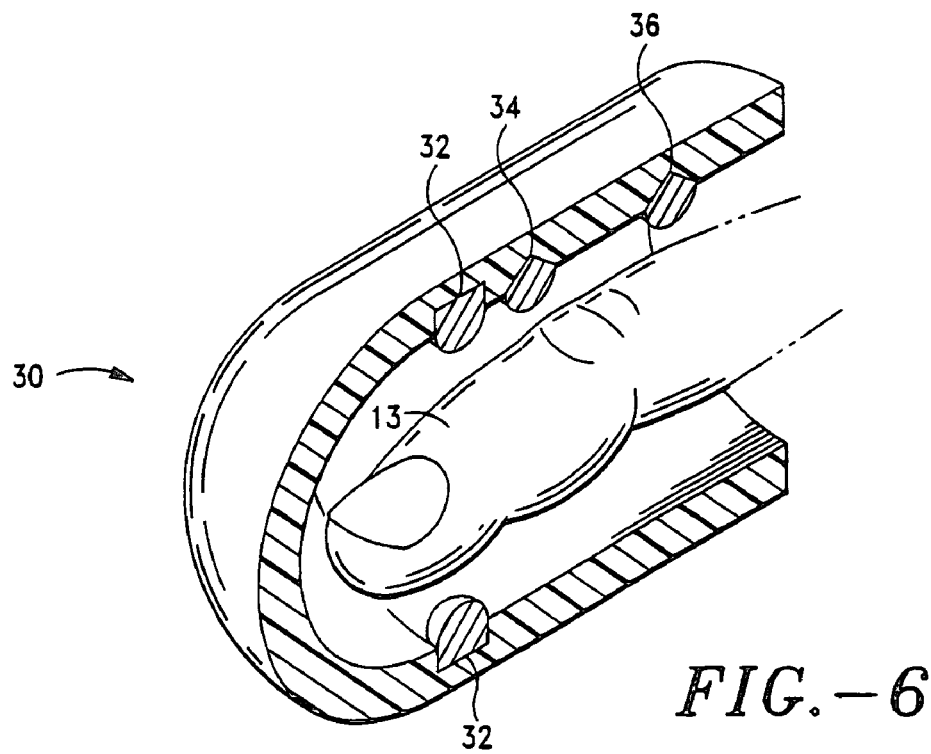
FIG. 6 is a partial perspective view of an alternative embodiment of a tissue probe with a single emitter-detector pair and two ECG electrodes, according to the invention.
Figure 7:
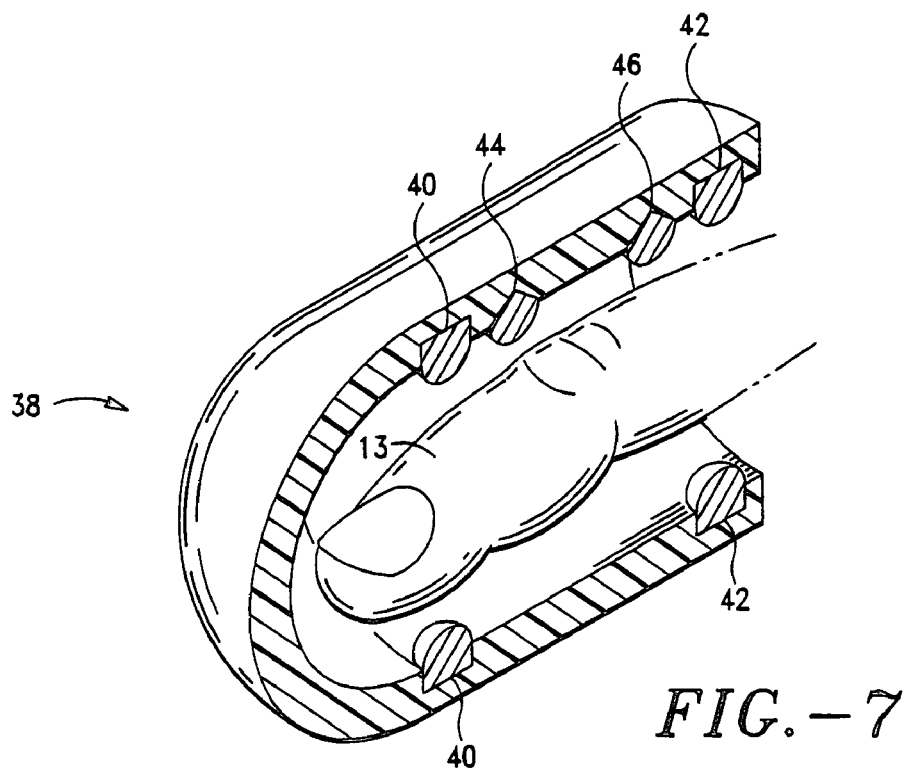
FIG. 7 is a partial perspective view of an alternative embodiment of a tissue probe with a two emitter-detector pairs and two ECG electrodes, according to the invention.

In certain embodiments of the invention, the probe comprises one or more electrocardiogram (ECG) electrodes in conjunction with the emitter-detector pairs. For example, FIG. 5 shows a probe 24 with a single emitter-detector pair 26 and a single electrocardiogram (ECG) electrode 28. Similarly, FIG. 6 shows a probe 30 with a single emitter-detector pair 32 and two ECG electrodes 34 and 36 and FIG. 7 shows a probe 38 with two emitter-detector pairs 40 and 42 and two ECG electrodes 44 and 46. Such probes, if placed on opposite extremities of a patient, can be used to measure central and peripheral pulse wave velocity as well as ECG. Other configurations, such as double emitter-detector pairs and single ECG electrode, can be envisioned.

Figure 8:
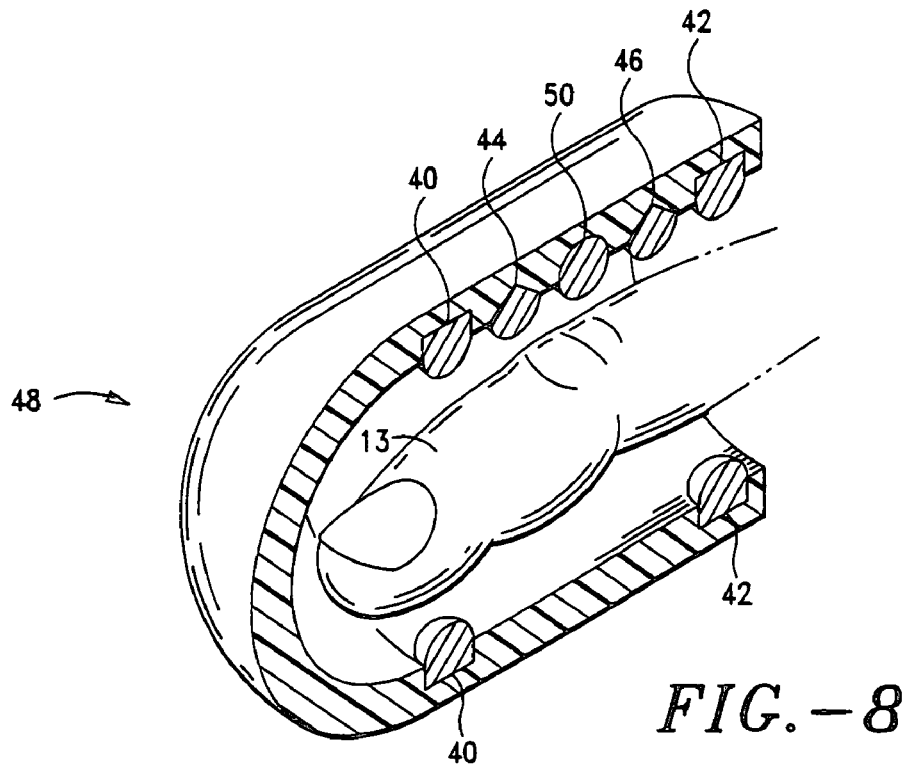
FIG. 8 is a partial perspective view of an alternative embodiment of a tissue probe having a position sensor, according to the invention.

In yet other embodiments of the invention, the probe further comprises a position sensing or measuring device together with the emitter-detector pairs and/or ECG electrodes. FIG. 8 shows a probe 48 similar to that shown in FIG. 7 with the addition of a position sensor 50. This position sensor could be used in conjunction with a position sensor placed at heart level in order to determine the hydrostatic pressure difference between the two position sensors.

As discussed in detail herein, the invention employs hydrostatic pressure to enable precise self-calibration of the devices in a completely noninvasive manner. Hydrostatic pressure affects all liquids. Gravity or other acceleration will affect both the arterial and venous sides of the circulation. It affects all aspects of the blood pressure equally—mean, systolic, diastolic. For example, an increase in height that causes a change of 10 torr will change every pressure measurement during the cardiac cycle by this amount.

For example, if the "true" blood pressure (taken level with the heart) is 120/80, when the arm is raised an amount needed to decrease the measured pressure by 10 torr, the measured pressure in the arm will be 110/70. The pulse pressure will be the same, but the transmural pressure will be 10 torr lower at all times. In addition, the vessel will be smaller at all points.

The heart is taken to be the center of the circulatory system, and all values are in reference to it. This is not necessary for the practice of the invention, but serves as reference points for values in the current medical literature.

The electromagnetic radiation in this description will refer to light in the visible and infrared range although, as noted in the attached claims, it is conceivable that other forms could be used.

Similarly, while the present invention primarily describes the use of transillumination, it will be appreciated that reflectance spectrophotometry may alternatively be employed.

Operating Principles

It is well known that Incident radiation passing through a body part is attenuated (absorbed) in the tissue. The theoretical basis for spectrophotometic techniques is Beer's law (the Beer-Lambert-Bouguer law) which expresses the incident intensity in terms of transmitted intensity and extinction coefficients of the tissue compartments through which the radiation has passed. The equation can be written as:

$$\ln(I/Io) = E*C*L \qquad \text{Eq. 1}$$

where:
Io=the incident intensity of the source radiation;
I=the transmitted intensity of the source through the sample;
E=the extinction coefficient of the component of interest;
C=the concentration of the component in the tissue itself;
L=the optical path length (distance) through the absorber; and
E*C*L=absorbance.

Beer's law and the practice of spectrophotometry and oximetry have been exhaustively reviewed in the literature. Generally, pulse oximetry in effect filters out signals other that pulsating (AC). In the body, it can be assumed that the pulsatile component of the signal is arterial blood, while all other tissue absorbers should be non-pulsatile (DC).

An additional feature of this invention, not found in any previous disclosure, is the use of hydrostatic pressure changes to vary not only the amount of arterial blood, but also the amount of venous blood within a body member such as a finger. Thus, hydrostatic changes can be used in a similar manner to the pulse to perform measurements on both arterial and venous blood. If a finger is contained within a probe, raising the probe will lower the hydrostatic pressure of all vessels in the finger, both arterial and venous. Both arteries and veins (and arterioles and venules) will be smaller due to lower pressure distending their walls. Most change will occur on the venous side of the circulation due to lower pressure. Total absorbance of the finger will decrease. As the arterial oxygen saturation can be measured by pulse oximetry, the venous oxygen saturation can be calculated in a similar manner.

A light signal of a known intensity and wavelength is produced by means of light-emitting diodes (LEDs) as in currently used oximeters or, as in one possible embodiment, a broad-band light source whereby wavelengths are isolated by a rotating filter or diffusion grating. In the latter case, the emitted light is distilled through a filter which allows a known wavelength and intensity of light to penetrate. Use of tunable lasers or other equipment is also possible. If the light source is proximate to the point of use, no further mode of transmission will be needed. If it is not, the light will be transported to the desired point by means such as a fiber optic cable, preserving the wavelength and intensity.

Several means of motion induction are possible. While a movement induction means is described herein, voluntary movement or other means are certainly possible. Various means of position measurement are also possible. For example, a liquid filled tube with an end open to the atmosphere can be employed. Other position sensors are known to those having skill in the art, and include electromagnetic, spectroscopic, ultrasonic, and chemical means. Preferably, a broad-band photo detector (in the case of visible or infrared light) or other means is employed to measure the quantity of transmitted light.

To generate a single data point, the movement induction means is used to bring the finger (or other space of interest) to a known position relative to the heart. Light of known wavelength and intensity is emitted (and transmitted if necessary) on the surface of interest. Detection of the light signal at a distinct point (normally opposing surface) is made and the relative absorbance and extinction of the signal is calculated. Signal processing is used to determine the pulsatile portion of the signal. The arrival time of the pulse is recorded, as is the amplitude and waveform. This measurement may be repeated one or more times to ensure the accuracy of the measurement; this can be done within a very short time frame (less than a millisecond).

To generate multiple data points, the process outlined in the previous step will be repeated at the next chosen wavelength, while still at the same predetermined position. The range and number of wavelengths can be selected, and changed for different applications.

Once the desired number of wavelengths has been examined, the movement induction means would bring the finger or other volume to a predetermined second position, and the data collection of steps would be repeated. At the completion of measurements and determinations for this second position, the movement induction means will bring the space to a third predetermined position, and the measurements and determinations repeated. This process would be continued until the desired range of positions has been scrutinized.

In order to make computations of pulse propagation delay, identical measurements would be made simultaneously with a probe on the same member on the opposite side of the body. For example, if one probe were placed on the index finger of the right hand, the other probe would be placed on the index finger of the left hand.

Because the arterial path to the arm is essentially identical after the second part of the subclavian artery, any differences in pulse wave velocity and pulse wave propagation time must occur prior to this point; that is, very close to the root of the aorta. In any case, pulse wave velocity increases rapidly as the pulse wave propagates down the aorta and into the periphery (Fung). Thus, any timing differences in the periphery will be greatly reduced by the high wave velocity, leaving central effects as the most prominent.

The apparatus of the invention can be operated intermittently or continuously. In the intermittent mode, a single set of calculations can be used for analysis to produce the determinations claimed. However, the device can also be easily operated in continuous mode, with the process outlined above repeated as often as wished (constantly if desired). In addition, a rapid ("stat") mode can be offered with the minimum number of measurements made that will provide an accurate estimation of correct values. Such a rapid mode would be useful in emergency situations.

While this methodology should give precise values, further adjustment may be desired to compensate for any discrepancies between theoretical and in vivo measurements. Contemporary oximeters in fact use a calibration curve when determining oxygen saturation, with the curve being generated with data from normal volunteers.

Calculations and Analysis

The following algorithms are further examples of the use of the present invention. Some variables have degrees of co-dependence. In these cases, values are calculated by iterative computational techniques.

Figure 9:
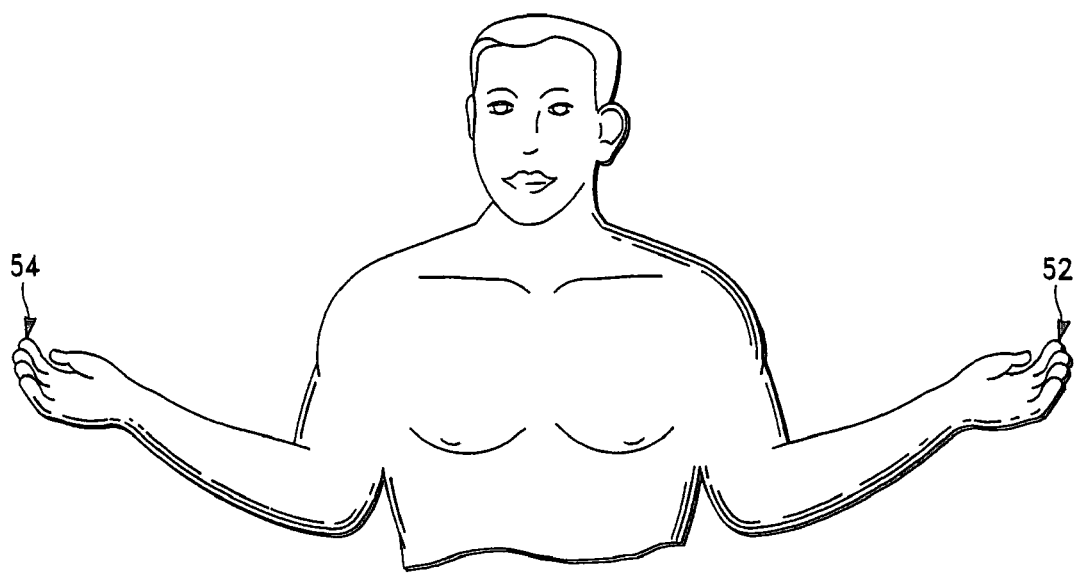
FIG. 9 is a schematic illustration of a patient with tissue probes placed on opposite digits according to the invention.
Figure 10:
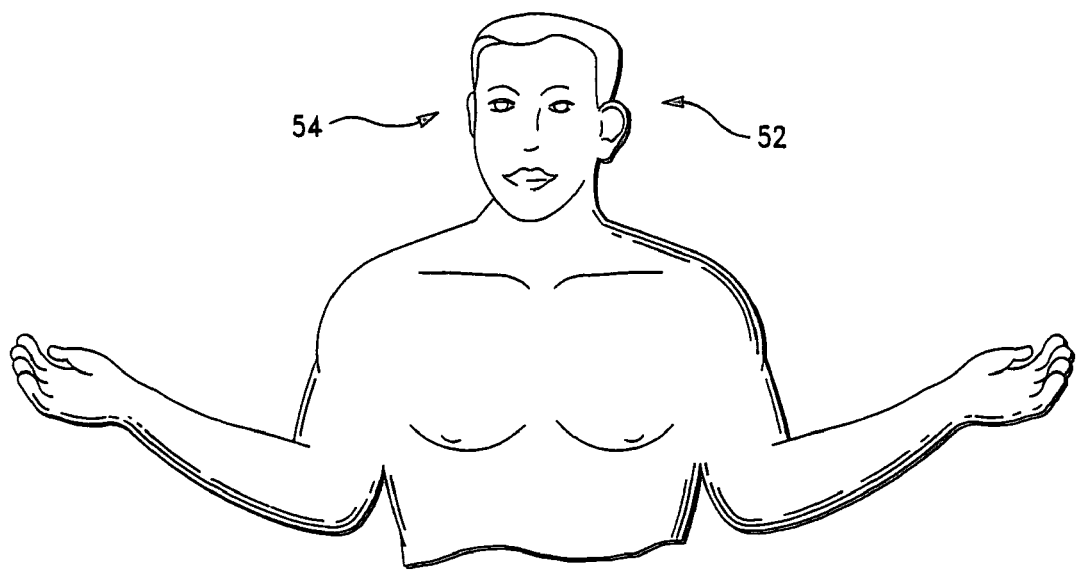
FIG. 10 is a schematic illustration of a patient with probes placed on opposite temples, according to the invention.

According to the invention, measurement of pulse wave amplitude and timing is made using probes such as that shown in FIG. 2, using methods similar to standard oximetry described in the prior art. Referring to FIG. 9, a first probe 52 is placed on a finger and set at a known position relative to the heart. Another, simultaneous measurement of pulse wave amplitude and timing is made by a second probe 54 placed on a finger on the hand opposite that of the first probe. The pulse delay occurring between the two measurements is made. Alternatively, as shown in FIG. 10, probes 52 and 54 can be placed on opposite temples of the patient to measure pulse wave values and delay. The probes can also be placed on the patient's ears.

From this information alone, an estimate of pulse wave velocity at the aortic root could be made, by utilizing a table of normal values for the distance of the central anatomical difference.

If a measurement of blood pressure is then made, one can perform the following calculation:

$$p = c*u*\rho \qquad \text{Eq. 2}$$

where:
c=pulse wave velocity;
u=flow wave velocity; and
$\rho$=the density of the blood (approximately 1.055 grams/cm$^3$).

According to the invention, p and c are measured, and $\rho$ is known. This allows one to solve for u, which is the flow wave velocity at the aortic root. This by itself is a measure of cardiac output. If one makes an estimate of aortic root diameter, one can then compute cardiac stroke volume.

According to the invention, various well-known, conventional reconstruction techniques can be employed to convert or "transform" peripheral blood pressures and waveforms to the corresponding pressure and waveform at the aortic root. Ideally, the blood pressure at the aortic root should be used as the pressure term in Fung's equation.

One can improve on the above determination in several ways. The first way is by additionally measuring the peripheral pulse wave velocity. To do this, measurement of pulse wave amplitude and timing is made by a first probe such as that shown in FIG. 5. The probe is at a set known position relative to the heart. Another, simultaneous measurement of pulse wave amplitude and timing is made by a second probe placed on a finger on the hand opposite that of the first probe. The pulse delay occurring between the two measurements is made. The respective peripheral pulse wave velocities are also computed. If the peripheral pulse wave velocities are different, it can be assumed that this is because of the different central anatomies from which the respective pulses traveled. This information alone may be enough to compute central pulse wave velocity from a table of normals. However, when combined with the pulse wave delay information, this data enables one to construct a function of pulse wave speed from the periphery back to the aortic root, thus giving another measure of central pulse wave velocity.

Another method of the invention is to vary the position of the probes relative to the heart. If the first probe is at heart level and the second probe is raised above (with respect to the earth) heart level, the hydrostatic pressure of the blood vessels within the second probe will be lower than those within the first probe. In turn, in accordance with Fung's equation stated above, this means that the pulse wave velocity of the arterial vessels within the second probe will be lower than that in the arterial vessels within the first probe. This will change both the measured pulse delay between the two probes, and the measured peripheral pulse wave velocities. This creates additional measurements by which to compute central pulse wave velocity.

According to the invention, changes in hydrostatic pressure are controlled by the following equation:

$$p = \rho*g*h \qquad \text{Eq. 3}$$

where:
$\rho$=blood density;
g=gravitational acceleration (approximately 9.8 meters/sec$^2$); and
h=height above a reference point (with respect to the earth).

The difference in hydrostatic pressure between the vessels in two probes is thus governed completely by their difference in heights relative to the heart (referenced to the surface of the earth). Therefore, a known change in position produces a known change in hydrostatic pressure.

According to the invention, the above measurements can be employed to derive a number of physiological properties. Preferably, the probes of the invention are connected to a controller to aid the data collection and analysis used to make the desired determination. The controller includes a computing device or standard personal computer (PC) with a monitor. Included within the controller are algorithms for the calculation of variables not measured directly.

Figure 11:
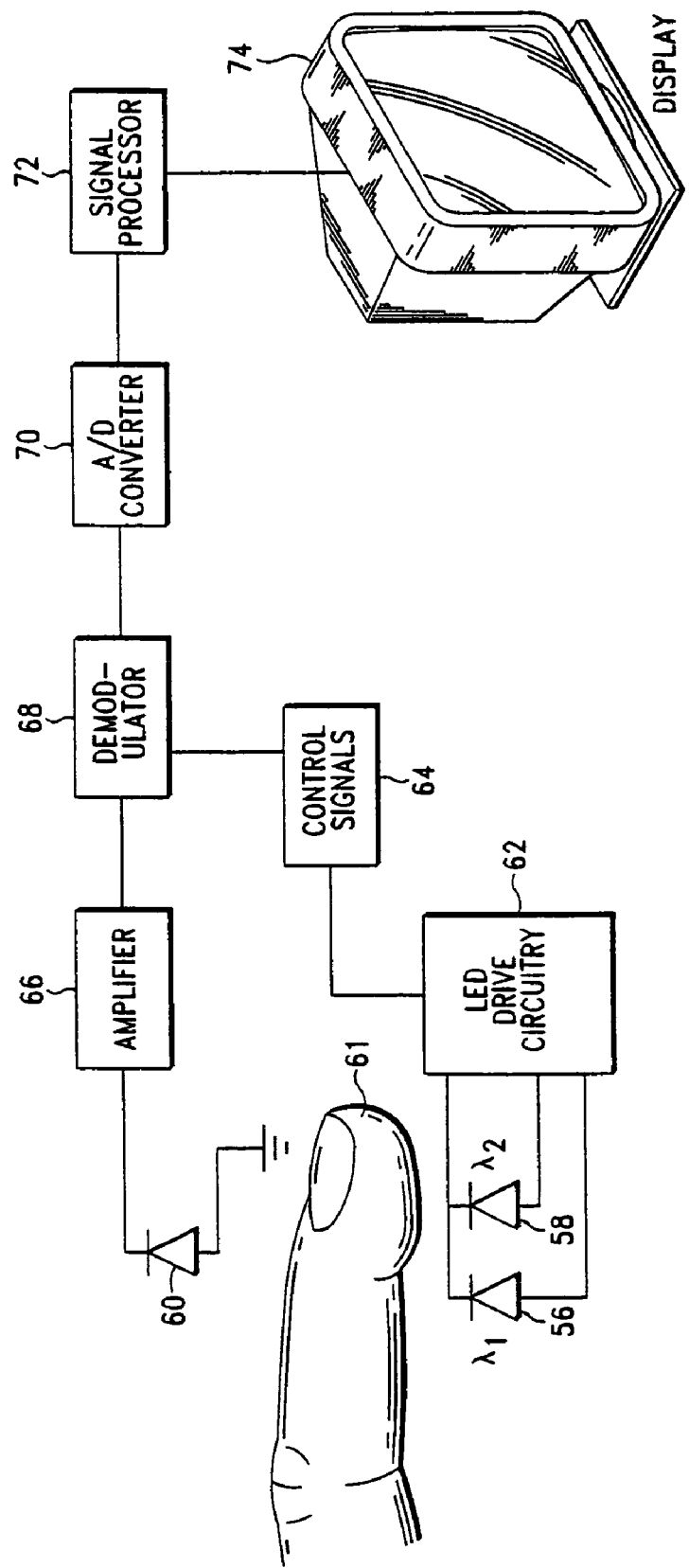
FIG. 11 is one embodiment of a circuit schematic including a photoplethysmogram, according to the invention.

For example, referring to FIG. 11, there is shown a circuit schematic for a one or two wavelength photo-plethysmograph. Emitters 56 and 58 and detector 60 are positioned adjacent the tissue being measured, such as a finger 61. Emitters 56 and 58 are driven by drive circuitry 62, which is in turn governed by control signal circuitry 64. Detector 60 is connected to amplifier 66. The signal from amplifier 66 is sent to demodulator 68, which is also synched to control signal circuitry 62. The signal from the demodulator 68 is sent to analog-digital converter 70. The desired computations are performed on the output from the converter 70 by signal processor 72 and the results sent to display 74. Emitters 56 and 58 operate specific wavelengths, such as 805 nm, and may comprise light emitting diodes (LEDs) or laser diodes. Detector 60 preferably comprises a silicon photodiode. Such emitter-detector pairs are shown in FIGS. 2 and 3.

Figure 12:
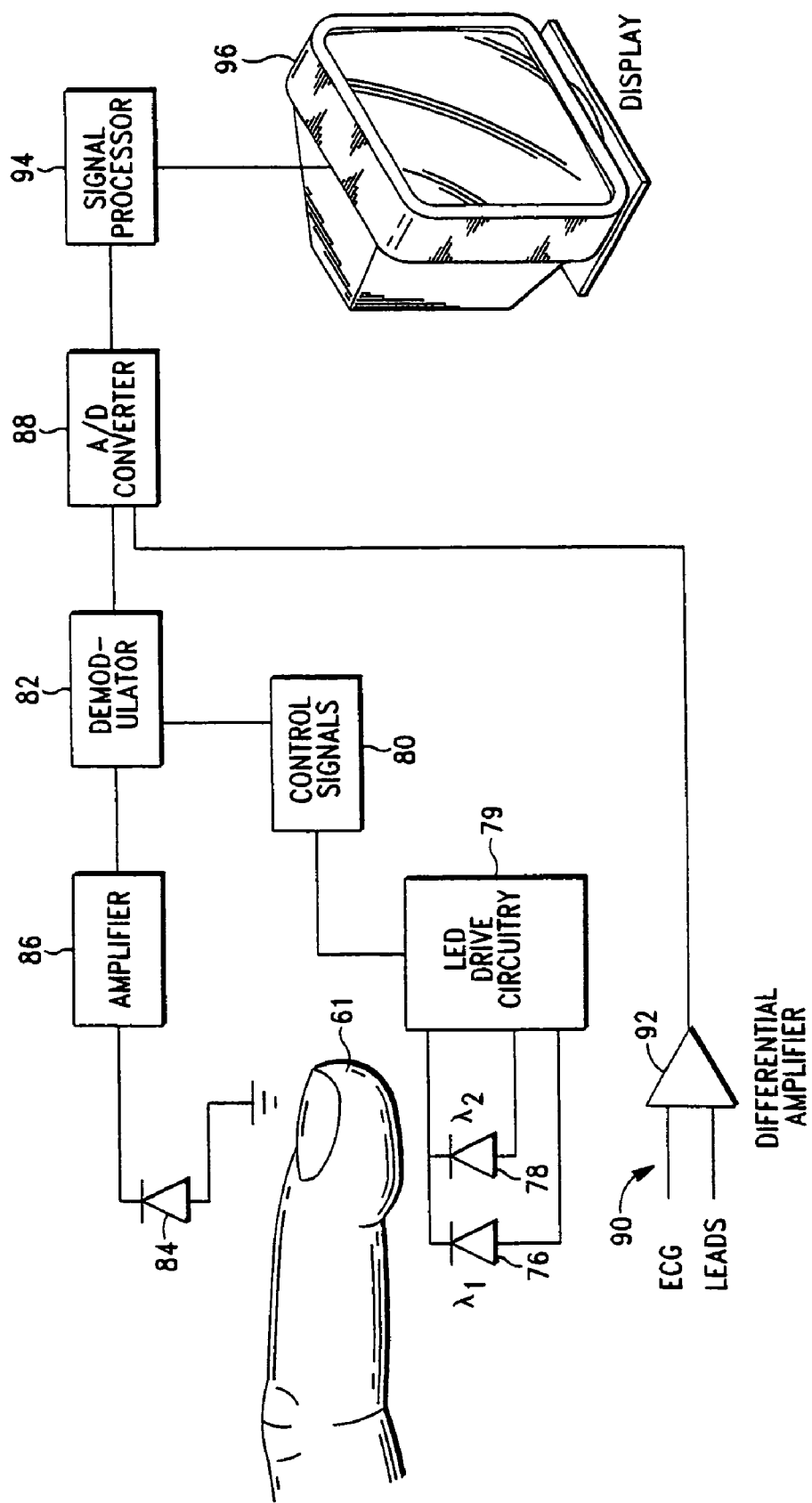
FIG. 12 is an alternative embodiment of a circuit schematic having a photoplethysmogram with an ECG amplifier, according to the invention.

Referring now to FIG. 12, there is shown a schematic of an alternate embodiment of suitable circuitry. As with FIG. 10, emitters 76 and 78 are connected via LED drive circuitry 79 and control signal circuitry 80 to demodulator 82. Signal from detector 84 is amplified at circuit block 86 and sent to demodulator 82. Output from demodulator 82 is sent to A/D converter 88. In addition, ECG leads 90 are connected to differential amplifier 92 and the signal is sent to converter 88. Output from converter 88 is processed at block 94 and the results sent to display 96. A probe such as those shown in FIGS. 5 and 6 may be used with the circuitry. The ECG leads are preferably silver/silver chloride or stainless steel.

Figure 13:
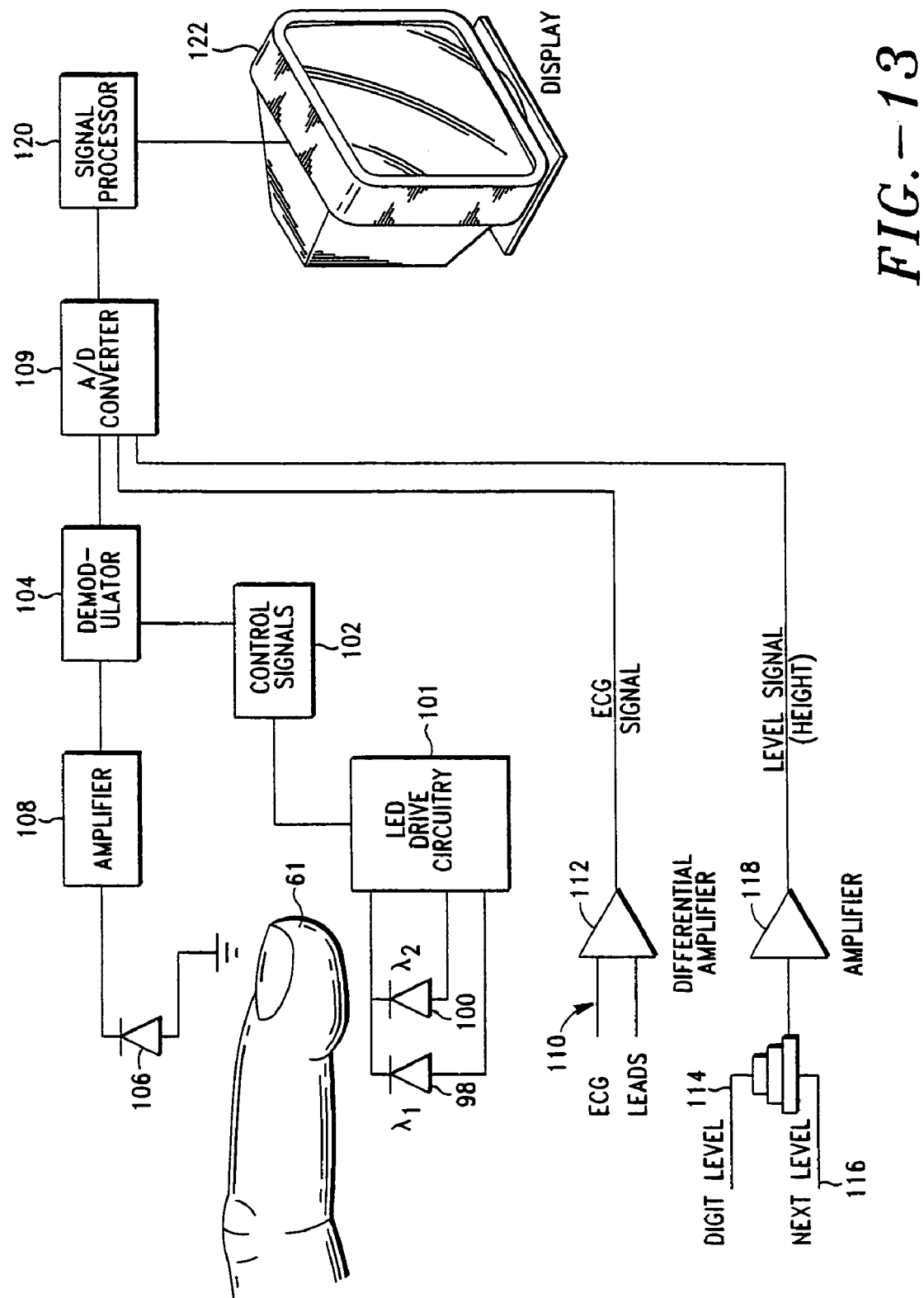
FIG. 13 is an alternative embodiment of a circuit schematic having a photoplethysmogram with an ECG amplifier and a level signal, according to the invention.

Yet another embodiment of the invention is shown in FIG. 13. Emitters 98 and 100 are connected via LED drive circuitry 101 and control signal circuitry 102 to demodulator 104. Signal from detector 106 is amplified at circuit block 108 and sent to demodulator 104. Output from demodulator 104 is sent to A/D converter 109. ECG leads 110 are connected to differential amplifier 112 and the signal is sent to converter 109. Digit level sensor 114 and heart level sensor 116 are connected to amplifier 118 and the signal is sent to converter 109. Output from converter 109 is processed at block 120 and the results sent to display 122.

Figure 14:
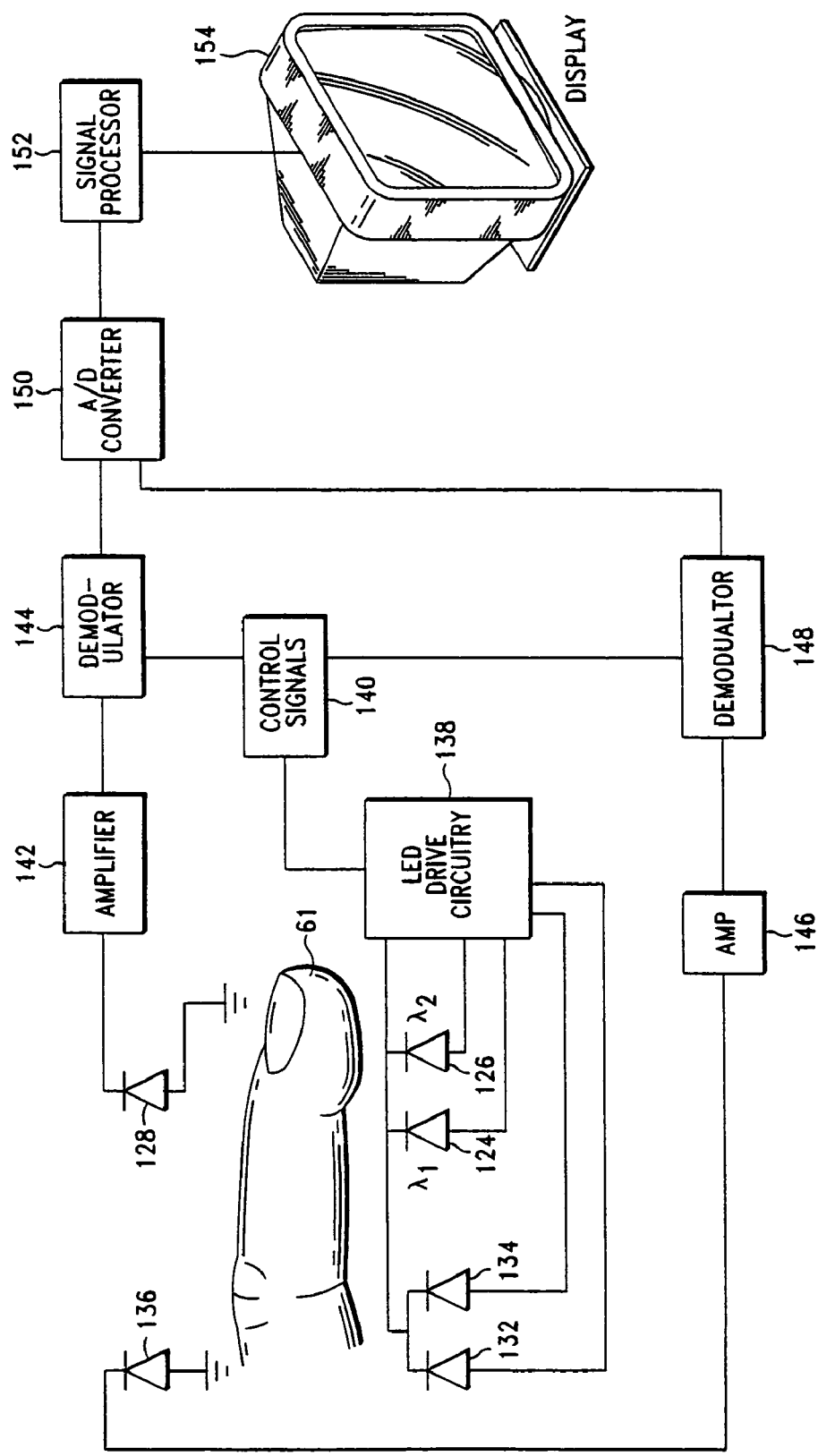
FIG. 14 is an alternative circuit schematic having a photoplethysmogram with two independent channels, according to the invention.

Referring to FIG. 14, there is shown a circuit schematic suitable for use with a probe having two physically independent channels, such as the one shown in FIG. 4. A first emitter-detector pair comprising emitters 124 and 126 and detector 128 are positioned adjacent the tissue being measured, such as a finger. A second pair comprising emitters 132 and 134 and detector 136 are positioned a selected distance from the first pair. Emitters 124, 126, 132 and 134 are driven by drive circuitry 138, which is in turn governed by control signal circuitry 140. Signal from detector 128 is amplified by block 142 and sent to demodulator 144. Independently, signal from detector 136 is amplified and demodulated at blocks 146 and 148, respectively. Output from demodulators 144 and 148 is sent to analog-digital converter 150. The desired computations are performed on the output from the converter 150 by signal processor 152 and the results sent to display 154.

Figure 15:
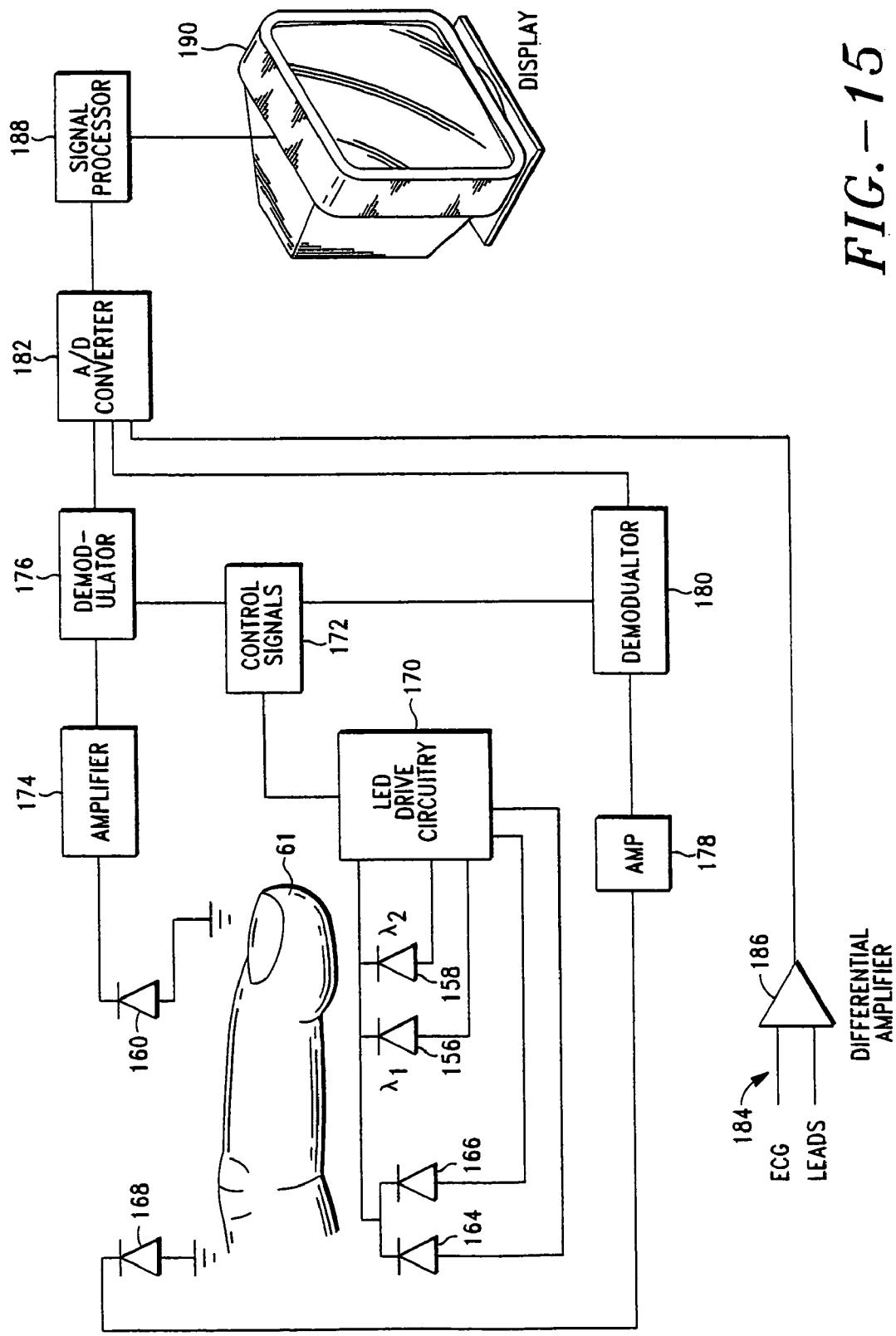
FIG. 15 is an alternative circuit schematic having a photoplethysmogram with two independent channels and an ECG amplifier, according to the invention.

An alternative embodiment configured for use with a probe having two physically independent channels and an ECG lead, such as the one shown in FIG. 7, is schematically illustrated in FIG. 15. A first emitter-detector pair comprising emitters 156 and 158 and detector 160 are positioned adjacent the tissue being measured, such as a finger. A second pair comprising emitters 164 and 166 and detector 168 are positioned a selected distance from the first pair. Emitters 156, 158, 164 and 166 are driven by drive circuitry 170 which is in turn governed by control signal circuitry 172. Signal from detector 160 is amplified by block 174 and sent to demodulator 176. Independently, signal from detector 168 is amplified and demodulated at blocks 178 and 180, respectively. Output from demodulators 176 and 180 is sent to analog-digital converter 182. ECG leads 184 are connected to differential amplifier 186 and the signal is also sent to converter 182 The desired computations are performed on the output from the converter 182 by signal processor 188 and the results sent to display 190.

Figure 16:
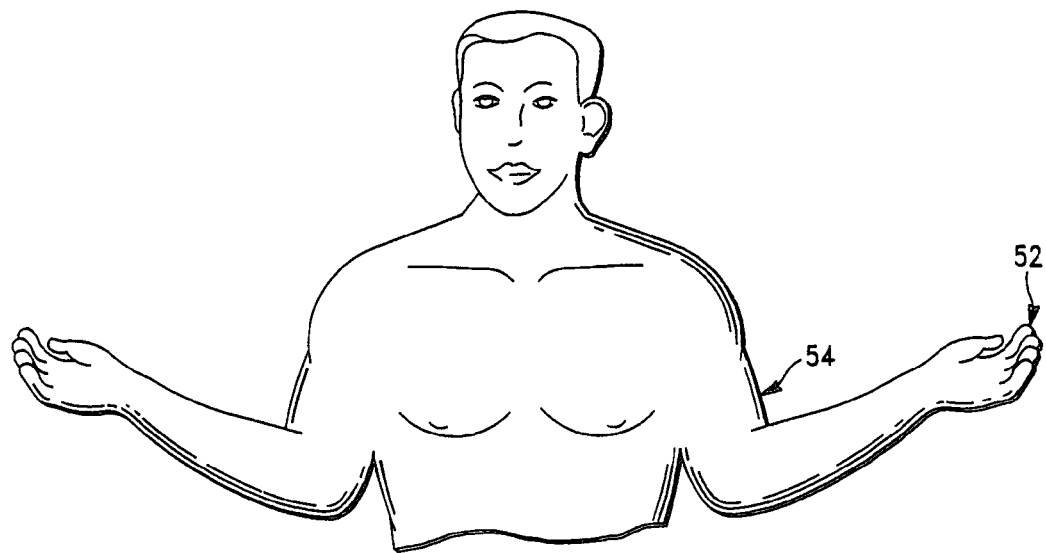
FIG. 16 is a schematic illustration of a patient with tissue probes placed on the digit and arm near the brachial artery, according to the invention.
Figure 19:
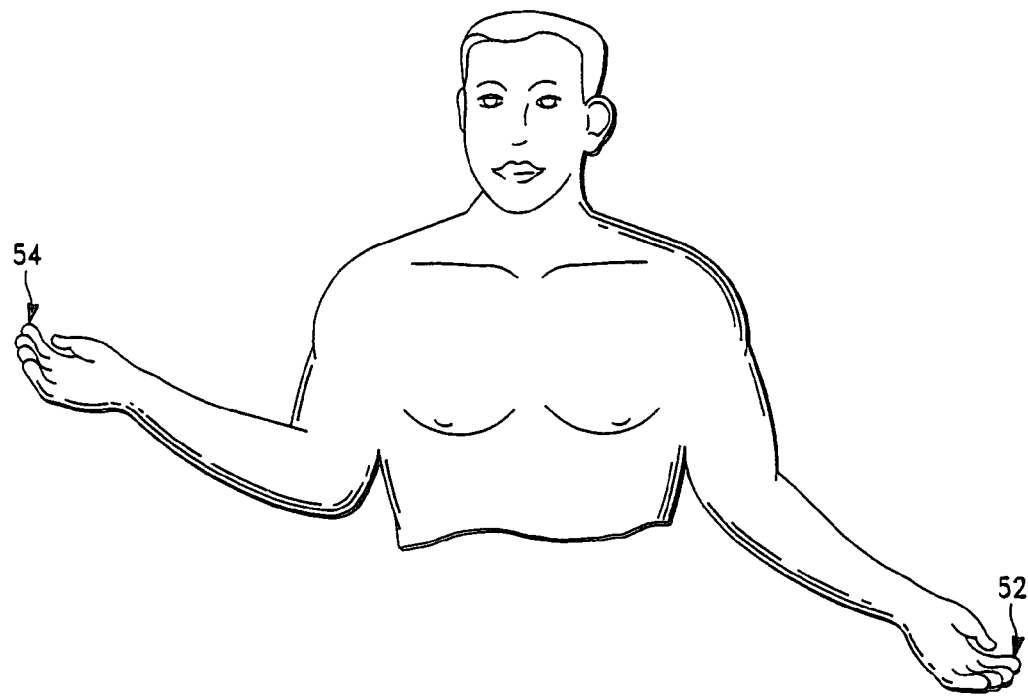
FIGS. 19 and 20 are schematic illustrations of patients with tissue probes placed on opposite digits and positioned at differential heights relative to the patients' heart, according to the invention.
Figure 17:
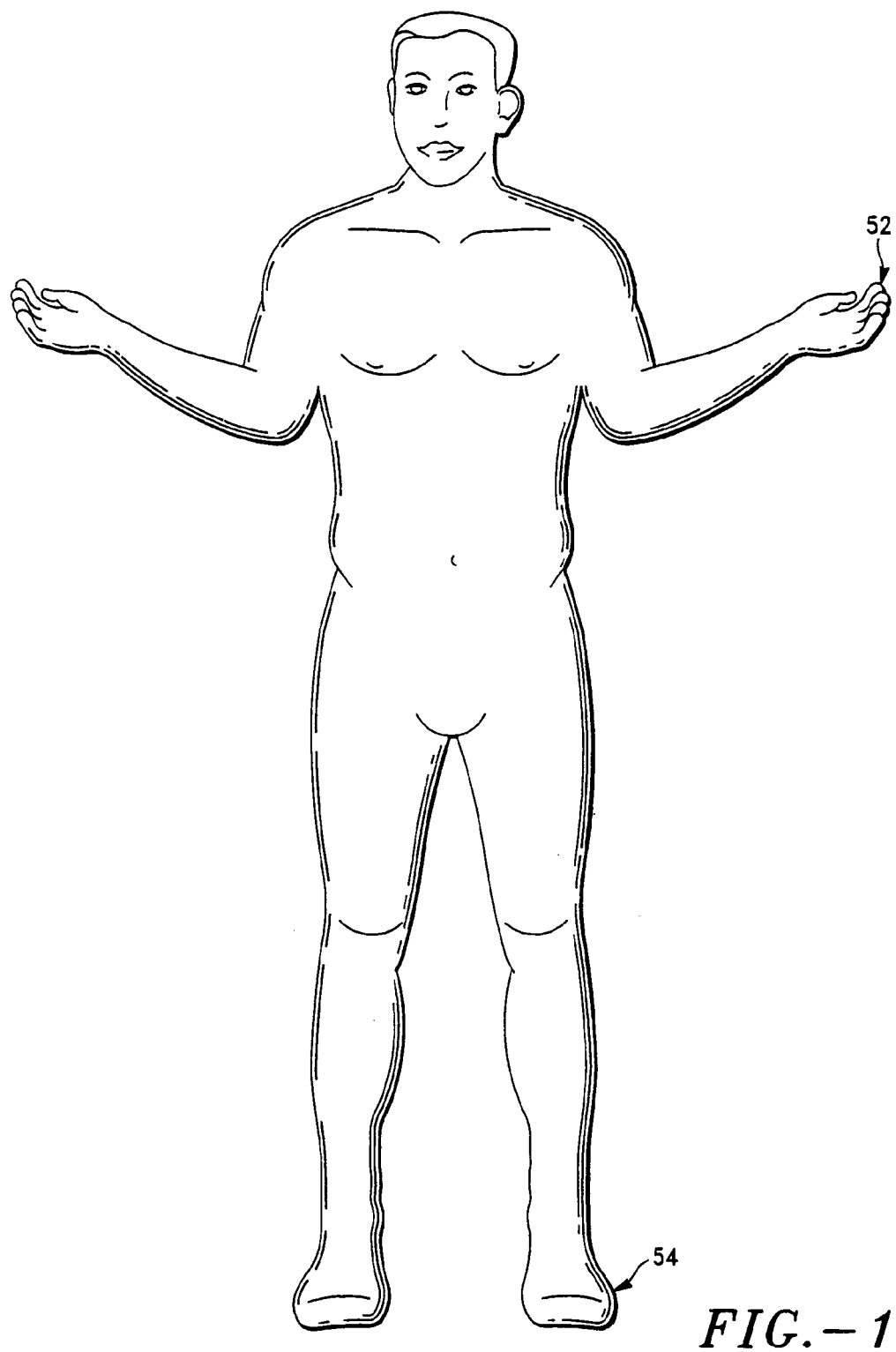
FIG. 17 is a schematic illustration of a patient with tissue probes placed on a finger and toe, according to the invention.
Figure 18:
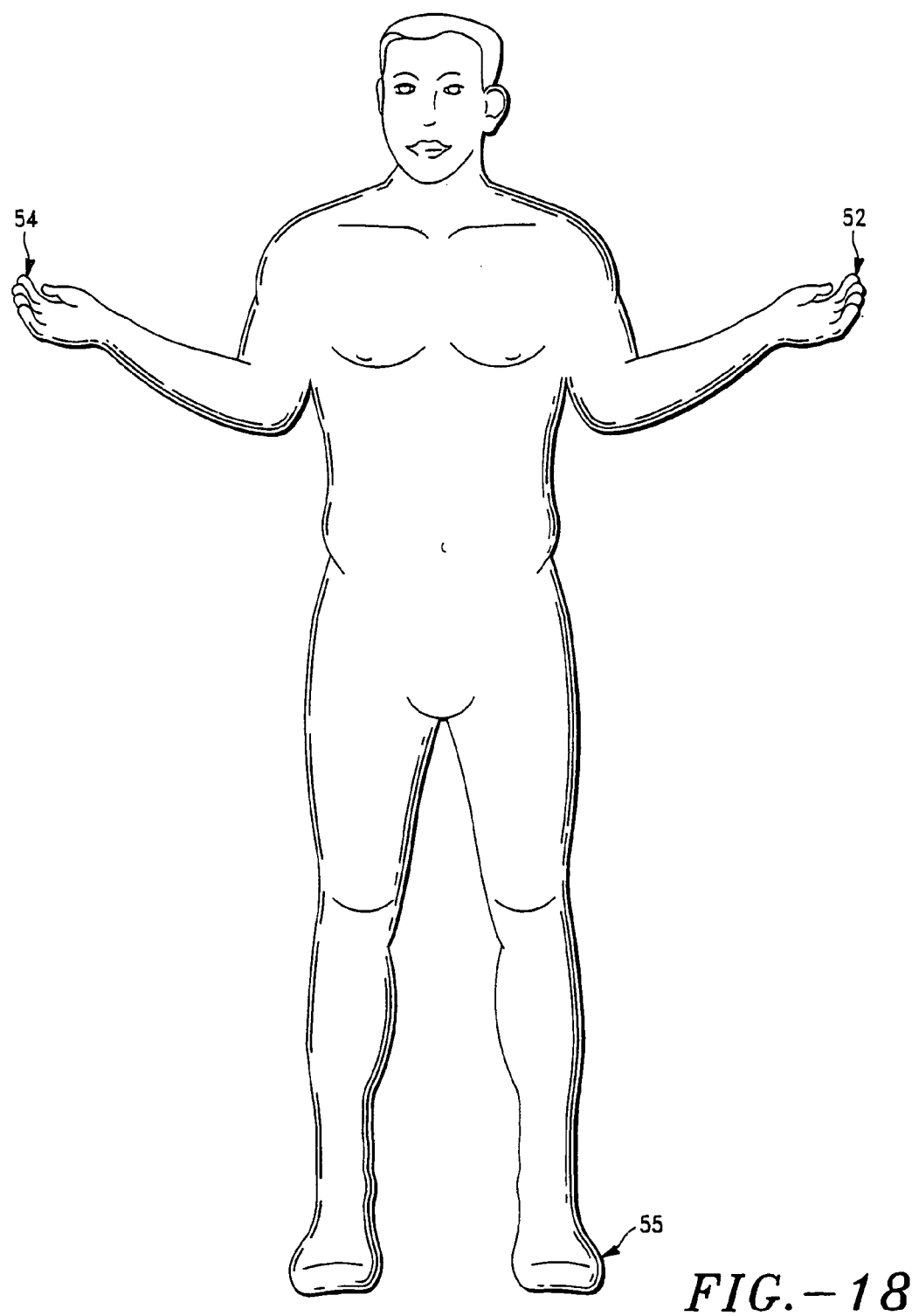
FIG. 18 is a schematic illustration of a patient with tissue probes placed on opposite fingers and a toe, according to the invention.
Figure 20:
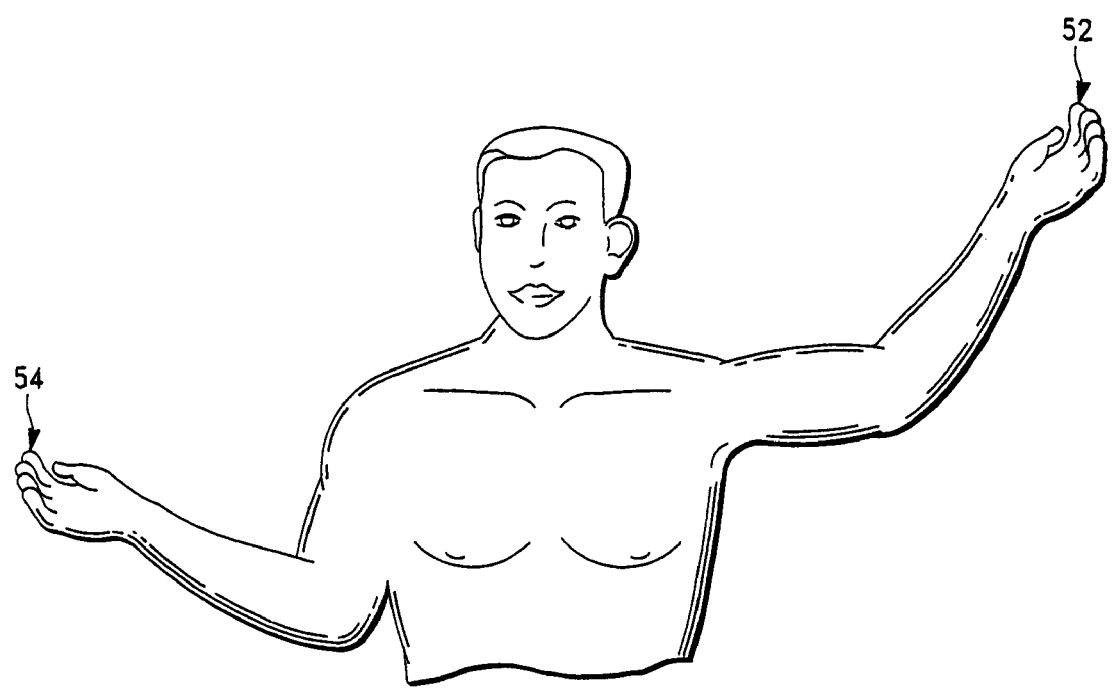
Figure 21:
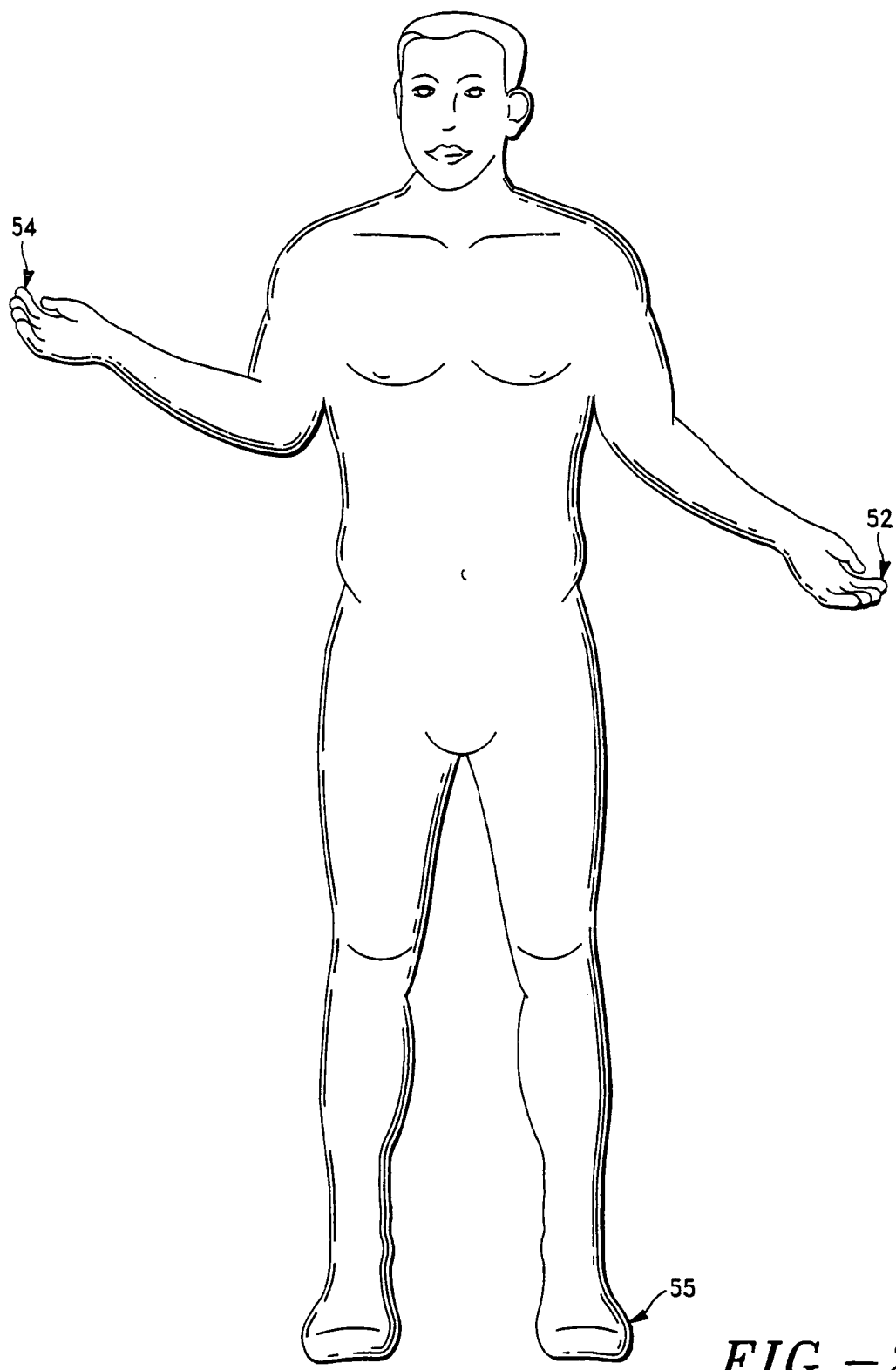
FIG. 21 is a schematic illustration of a patient with tissue probes placed on a toe and opposite fingers positioned at different heights, according to the invention.

As one of ordinary skill in the art will appreciate, the placement of the various probes discussed above will affect the types of measurements that can be taken. As discussed above, FIGS. 9 and 10 show probes placed on opposite extremities to enable measurement of pulse wave delay. FIG. 16 shows an embodiment of the invention with probe 52, such as in FIG. 1, placed on the digit, and a probe 54, such as in FIG. 2, placed on the arm near the brachial artery. This could measure the pulse wave velocity in the arm (as well as pulse oximetry). A similar embodiment could measure pulse wave velocity in the leg. FIG. 17 shows probes 52 and 54 placed on a finger and on a toe to measure the pulse wave delay. FIG. 18 shows probes 52 and 54 placed on opposite digits and probe 55 placed on a toe. This allows measurement of the differential pulse wave delay between the fingers and toe, and allows calibration of the toe probe to be used in place of a finger probe (if only one finger probe could be used, such as in hand surgery). The use of appropriate probes also allows a diagnostic-quality ECG. FIGS. 19 and 20 show probes 52 and 54 placed on opposite digits. One arm of the subject is placed at the level of the heart, while one arm is moved to different positions, both above and below the level of the heart. By generating different hydrostatic pressures in the vessels, the pulse velocity and hence pulse wave delay changes. In addition, the amplitude of the pulse wave, and amplitude of venous absorbance changes. This allows the additional computations of arterial blood pressure and venous pressure. FIG. 21 shows probes 52 and 54 placed on opposite digits and probe 55 placed on a toe. The differential hydrostatic pressures in the vessels allow measurements of pulse wave velocity and pulse wave delay, as well as arterial blood pressure and venous pressure. Use of probes with suitable ECG leads will also allow the invention to perform a diagnostic-quality ECG. In addition, heart rate and respiratory rate can be calculated, and cardiac output and several other cardiovascular characteristics computed.

Figure 22:
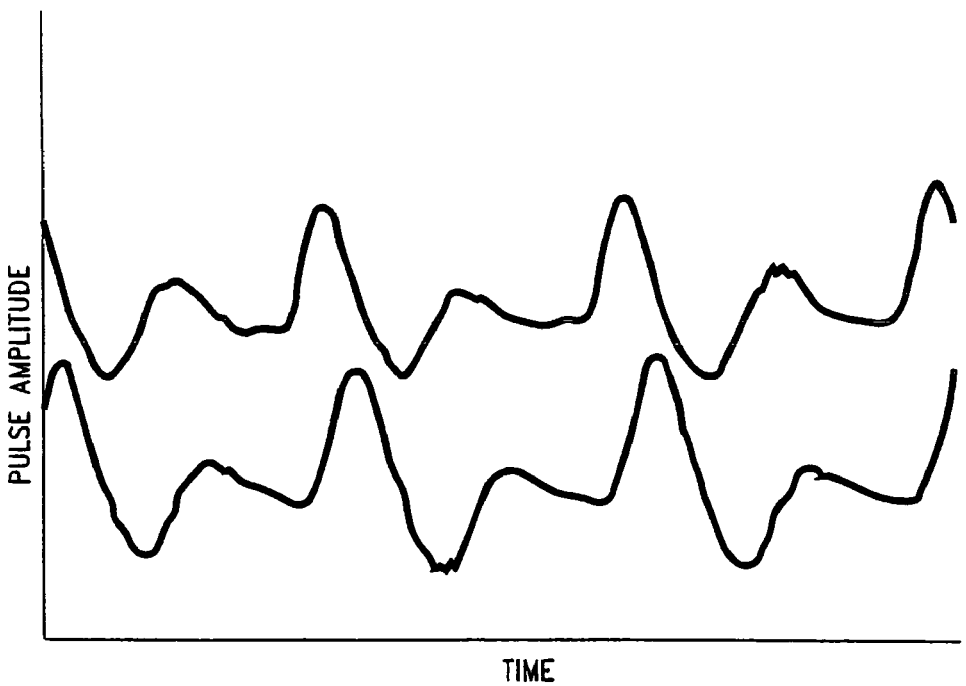
FIGS. 22-25 are graphical illustrations of oscilloscope tracings showing recordings using methods of the invention wherein the probes are placed on index fingers of opposite hands, and the pulse velocities and relative arrival times are varied by changing the heights of the probes relative to the heart.

As discussed above, the controllers of the invention preferably output the results of the measurements and computations to a display. Referring now to FIG. 22, there are shown two oscilloscope tracings from pulse oximeter probes, such as those shown in FIG. 1, placed on the index fingers of both hands. The pulse wave delay is visable as the slight phase difference between the two tracings. As the probes are at the same level, the pulse amplitudes are essentially identical.

Figure 23:
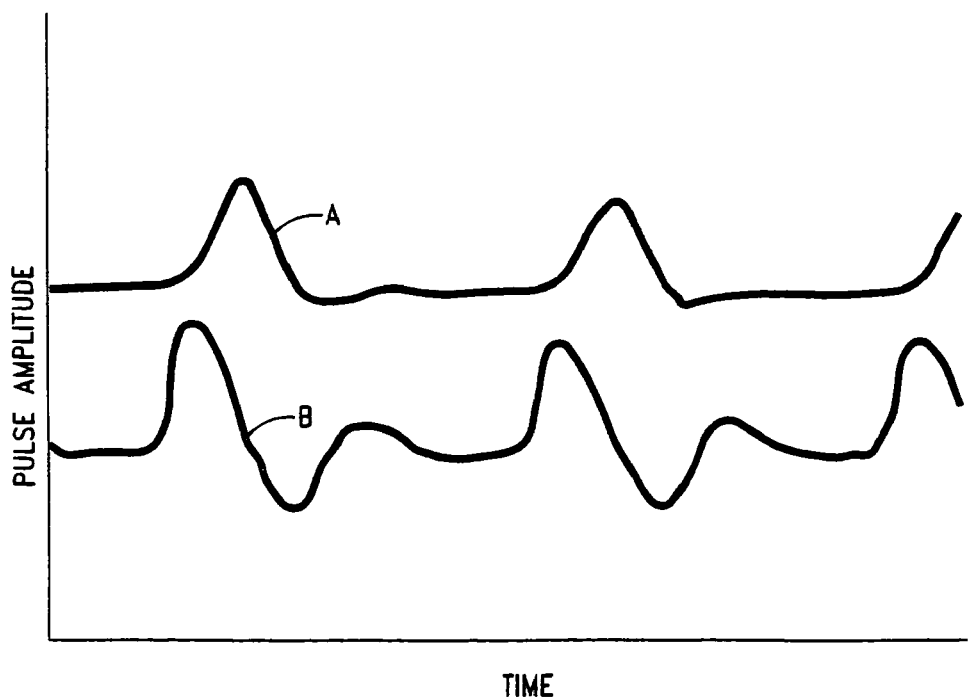

Referring to FIG. 23, there are shown oscilloscope tracings for a probe on a hand placed at a level higher than the heart (Curve A) and a probe on a hand placed at a level lower than the heart (Curve B). The induction of a pressure differential between the two probes effects a change in the pulse delay. The change in pressure also correspondingly alters the pulse amplitudes.

Figure 24:
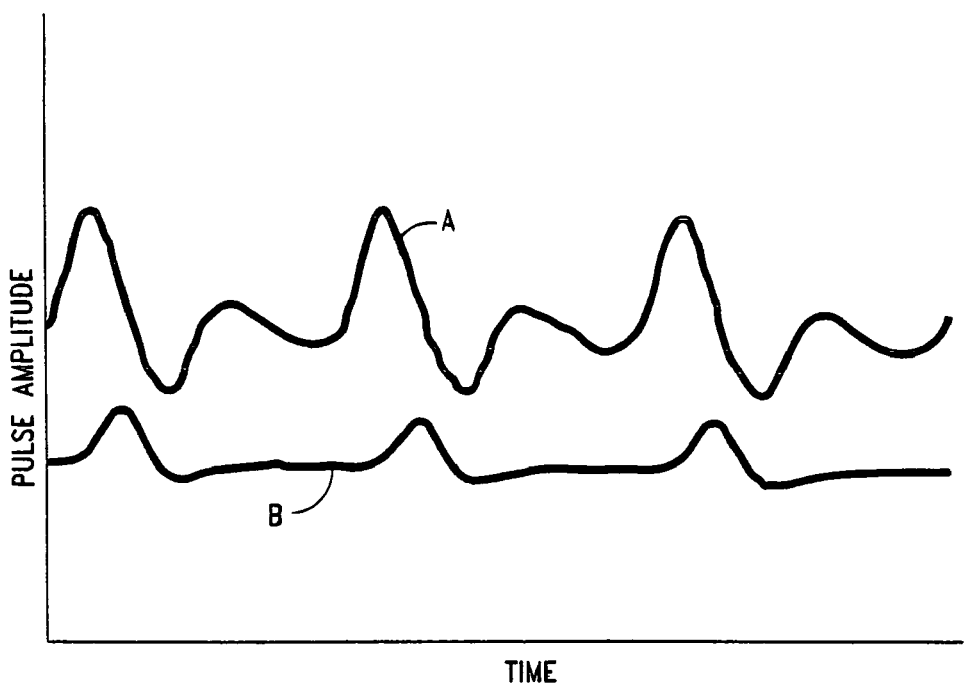
Figure 25:
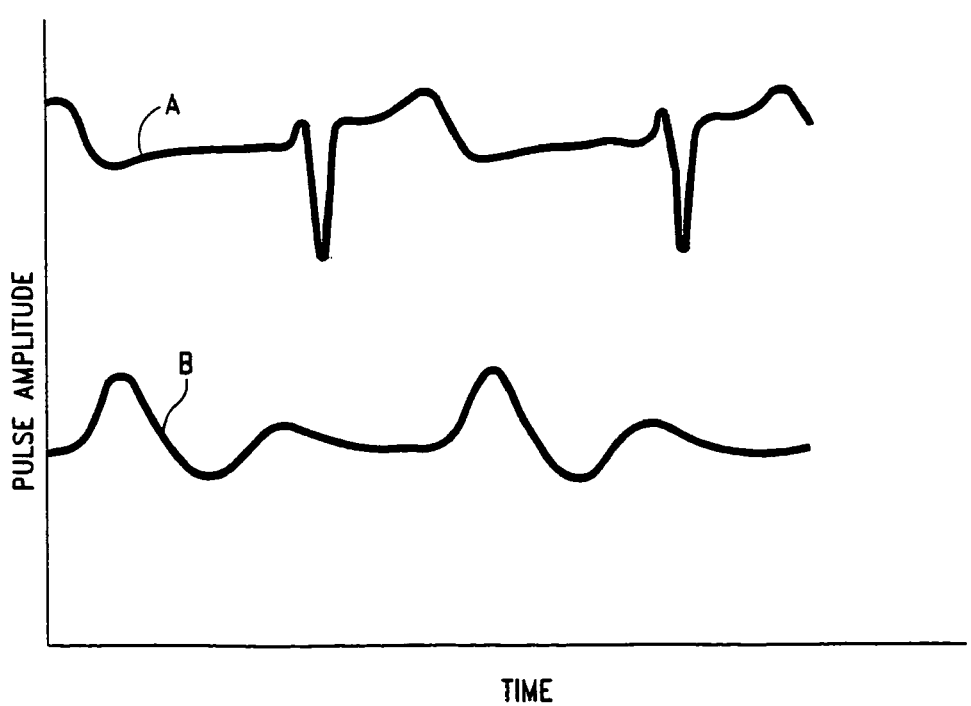

Referring now to FIG. 24, there are shown oscilloscope tracings for a probe on a hand placed at a level lower than the heart (Curve A) and a probe on a hand placed at a level higher than the heart (Curve B). Here, the pulse delay has substantially reversed as have the pulse amplitudes. FIG. 25 are oscilloscope tracings showing an electrocardiogram (Curve A) in conjunction with a pulse waveform (Curve B).

The algorithms outlined below serve as examples, but modifications are possible to arrive at the indicated results, and are meant to be included within the spirit of this application. Various additional components of the device will be discussed in more detail below with reference to the following exemplary determinations.

(D-1). Determination of Arterial Blood Pressure

A probe, such as that shown in FIG. 1, is placed on an extremity that is moved in relation to the heart. As mentioned above, the hydrostatic pressure within the arteries and arterioles changes as a function of height with respect to the heart. Because of this, both the pulse wave velocity and pulse wave amplitude change as a function of probe height. These two parameters can be mapped against known distance above or below the heart. In this way, function curves of pressure vs. pulse wave amplitude and pressure vs. pulse wave velocity can be drawn. For example, a full excursion of the arm in a standing adult produces hydrostatic changes of greater than 50 cm of water in both directions. Using an arm and a leg, a gradient of well over 200 cm of water can be generated. This is a significant portion of the normal blood pressure range, and certainly enough to produce the function curves mentioned above.

There is a huge amount of medical literature describing arterial behavior, so the curves can be extrapolated if necessary. These curves serve as calibration.

It can thus be determined if "recalibration" is necessary—if either pulse amplitude or pulse wave velocity changes, and the other parameter does not change correspondingly. In other words, a shift on one curve should be matched by a corresponding shift on the other curve. If this shift does not occur as predicted, recalibration is required. Of course, the process of recalibration is the simple procedure outlined above.

In a preferred embodiment, a first probe having a position sensor is placed level with the patient's heart. A second probe, such as one shown in FIG. 8, having a position sensor and a pulse detector is placed on the patient's finger. The patient's arm is held out level with the heart so there is zero displacement between probes. Pulse amplitude is recorded from probe. The patient's arm is slowly raised, while pulse amplitude and relative displacement of probe are recorded. The hydrostatic pressure difference between probes is also computed. By comparing the recorded pulse amplitude to the hydrostatic pressure difference, a mathematical function relating pressure to pulse amplitude can be derived. Preferably, circuitry similar to that shown in FIG. 13 is used to aid the process. This process is repeated while lowering the arm back to heart level, then lowering the arm to below heart level and, finally, raising the arm back to heart level. Similar steps can be applied to measure pulse delay, pulse velocity and pulse contour. Also preferably, frequency or Fourier analysis may be used to make the requisite determinations.

(D-2). Determination of Cardiac Output

Cardiac output can be determined by measuring delays in pulse arrival times in coupled organs or members on opposite sides of the body. In a preferred embodiment of the invention, probes such as those shown in FIG. 1, having sensors for detecting a patient's pulse are placed on opposite fingers of the patient. The patient positions both arms straight out from the side. The blood pressure of the patient can be determined either through conventional means or by the methods of the invention. The pulse delay between the two probes can be measured utilizing circuitry such as that shown in FIG. 14 or 15, for example. The dicrotic notch of the pulse may be determined by standard methods, and used to calculate the ejection time based on the timing. The size of the aortic root can be estimated by standard means and the consequently the pulse distance differential at the aortic root. This allows the calculation of the pulse velocity c at the aortic route by the following equation:

$$c = (\text{pulse distance})/(\text{pulse delay}) \qquad \text{Eq. 4}$$

The value of c can then be used to determine the flow wave velocity based on the following equation:

$$p = c * u * \rho \qquad \text{Eq. 5}$$

where:
c=pulse wave velocity;
u=flow wave velocity; and
$\rho$=density of the blood (approximately 1.055 grams/cm$^3$).

According to the invention, cardiac stroke volume can be determined by multiplying the aortic root area by the flow wave velocity and by the cardiac ejection time. Cardiac minute output can be calculated by multiplying the cardiac stroke volume by the pulse rate. These steps can be augmented by raising and lowering the patient's arms with respect to each other to vary the pressure and the pulse wave velocity.

Experiments by the inventor using a "single breath of oxygen" technique outlined below have shown that having the arms at different levels (and thus, different arterial blood pressures) results in different blood flows to the arms. The blood flow is thus obeying the classic fluidic version of Ohm's law:

$$p = f * r \qquad \text{Eq. 6}$$

where:
p=pressure
f=flow
r=resistance

Because of this, varying the pressure by small amounts (large amounts would cause changes in autoregulation) can be used to calculate blood flow and thus cardiac output. Since the pulse arrives at the two hands at different times, if the "faster" arm is raised, the pulse wave velocity slows. The pressure difference necessary to make the pulse arrive in both hands simultaneously can be calculated. In view of the pressure-flow relationship above, the ratio of pressure should be the same as the ratio of flow. The time difference, or number of heartbeats, of the flow arrivals in the two hands when they are level with the heart can be computed. In turn, this gives the cardiac index, as the closer the flow arrival times are, the higher the cardiac output. Likewise, the greater the flow arrival time difference is, the lower the cardiac output.

Alternatively, cardiac output can be determined by placing probes such as those shown in FIG. 5 on a patient's finger and toe. The probes measure oxygen saturation at each pulse. The oxygen saturation for each pulse at the first probe is compared to the oxygen saturation of that pulse and subsequent pulses at the second probe. With continuous monitoring, this allows the determination matching oxygen saturation, within given tolerance limits, of the pulses from the probes. The patient's blood volume and the physical separation of the probes can be determined by standard methods. This allows the computation of cardiac stroke volume by dividing the blood volume displaced by the number of pulses. Then, the cardiac minute output can be calculated by multiplying the cardiac stroke volume by pulse rate. Circuitry such as that shown in FIG. 11 or 12 is suitable for use with this embodiment.

In yet another embodiment, the principles used above may be used to calculate cardiac output on the basis of flow wave propagation as opposed to pulse wave. As described above, the propagation of the flow wave (physical passage of blood through the arterial system) happens much more slowly than that of the pulse wave (celerity). Thus, blood that is ejected during a single cardiac cycle will arrive at the two hands at a slightly different time, while the time difference between the arrival at a hand versus a foot may be much longer, in the order of several seconds.

The difficulty lies in determining the blood that was ejected during the same cardiac cycle. Two parameters that can be used to determine this are the hemoglobin oxygen saturation and the pH (acid-base balance). As will be discussed below in their respective sections, hemoglobin concentration and blood pH can be measured using the probes and techniques of the invention. All blood that is ejected during a single cardiac cycle can be assumed to have the same saturation and pH, because blood is very well mixed in the left atrium and left ventricle prior to ejection. Also, it can be assumed that the saturation and pH change very little during the passage of the blood through the arterial system, as the arteries behave like pipes, conveying the liquid but consuming or releasing minimal metabolites.

Figure 26:
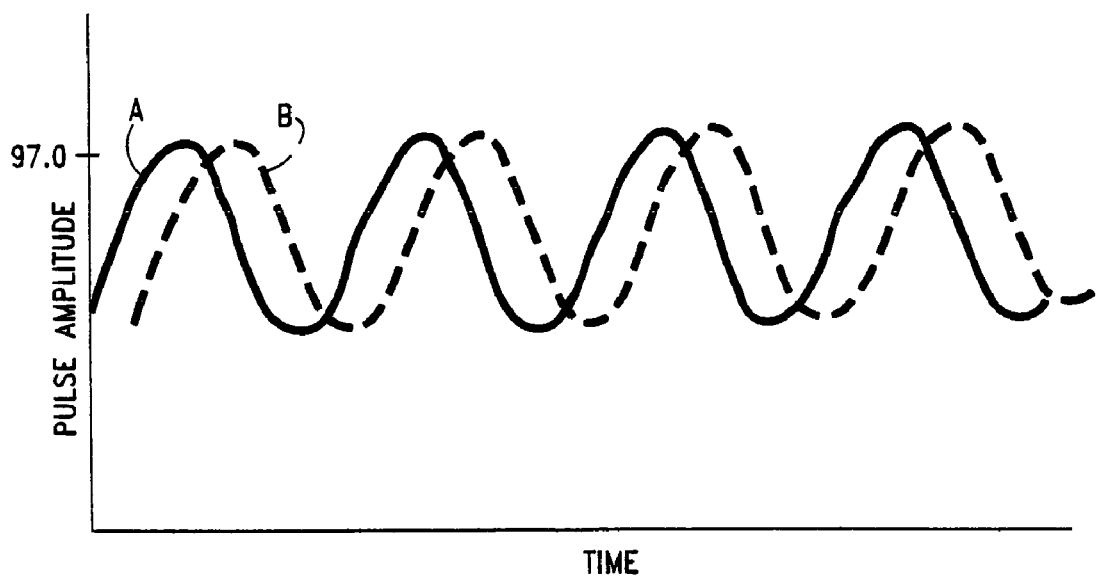
FIG. 26 is a graphical illustration of oscilloscope tracings showing trains of pulses with varying oxygen saturation values.

Both the saturation and pH change slightly in a continuous fashion due to the respiratory cycle and other factors. In addition, large changes can be caused by maneuvers such as voluntary hyperventilation or breathholding. Because of this, a pattern in either the saturation or the pH can be recognized, allowing one to "match" the pulses which reflect the blood ejected during the same heartbeat. The difference in arrival times can then be used to compute the cardiac output. By way of illustration, referring to FIG. 26, the first pulse train (Curve A) corresponds to the hand. The second pulse train (Curve B), which arrives later, corresponds to the foot.

Figure 27:
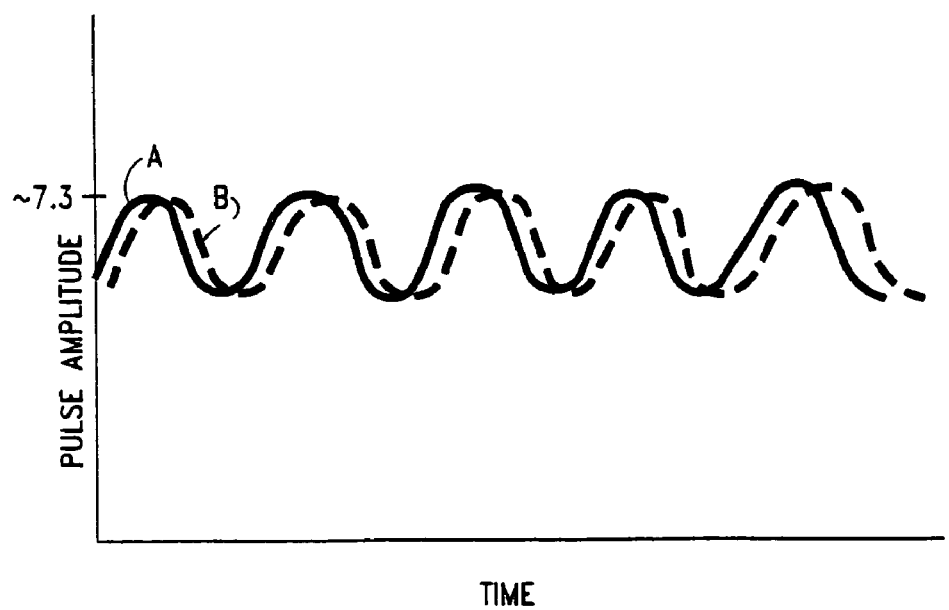
FIG. 27 is a graphical illustration of oscilioscope tracings showing trains of pulses with varying pH values.

FIG. 27 similarly illustrates this phenomenon for pulses of differing pH. The first pulse train (Curve A), which arrives earlier, corresponds to the hand. The second pulse train (Curve B) corresponds to the foot. According to the invention, additional, known parameters in addition to oxygen saturation and pH can also be employed.

Figure 28:
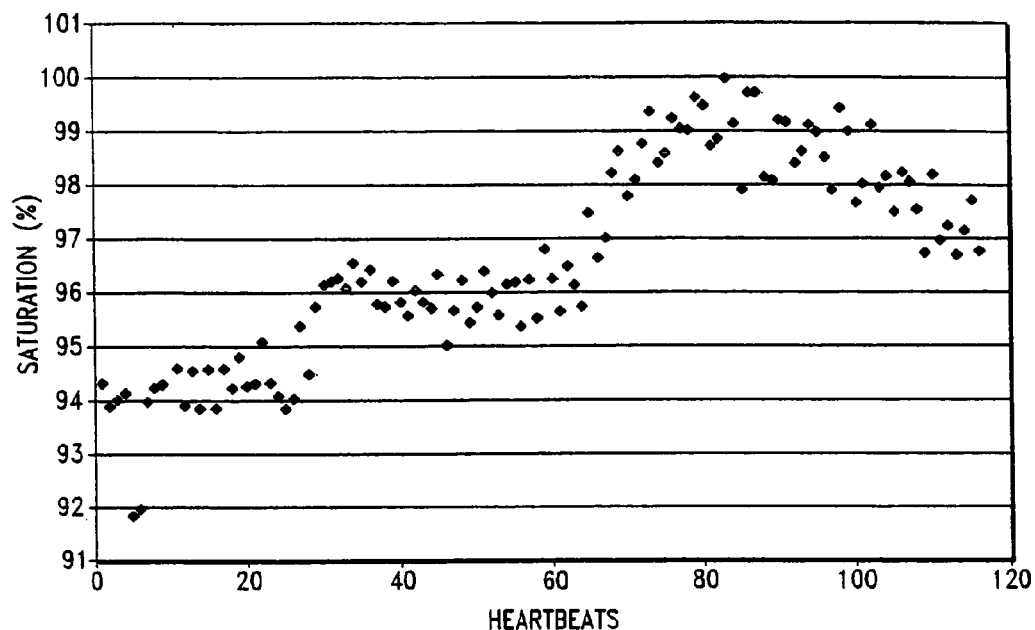
FIG. 28 is a graphical illustration of oxygen saturation versus heart rate showing the effects of induced changes in oxygen saturation measured at the toe.
Figure 29:
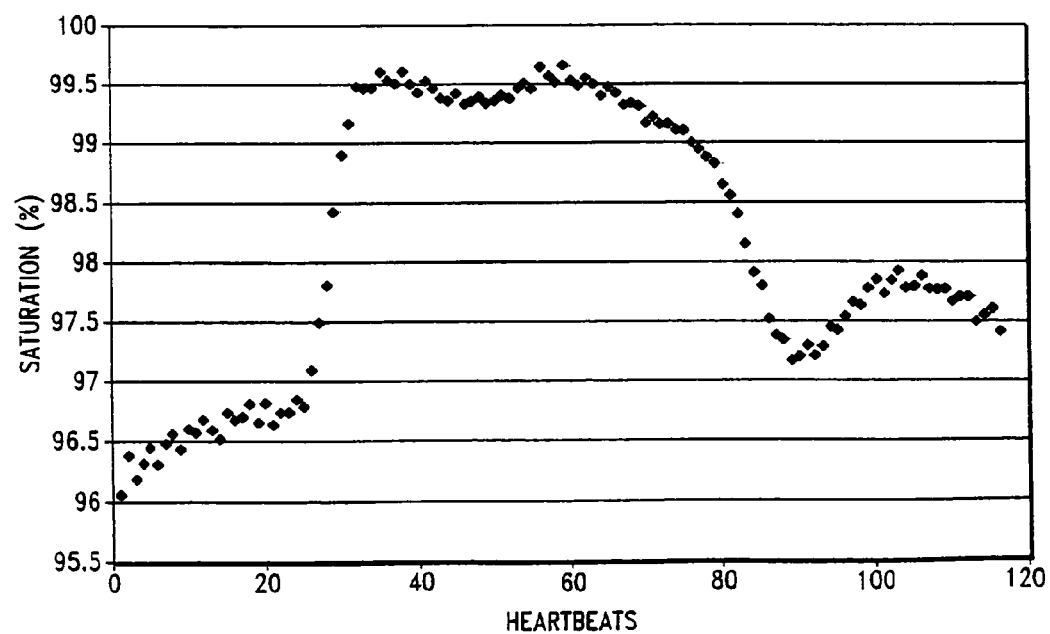
FIG. 29 is a graphical illustration of oxygen saturation versus heart rate showing the effects of induced changes in oxygen saturation measured at the left hand.
Figure 30:
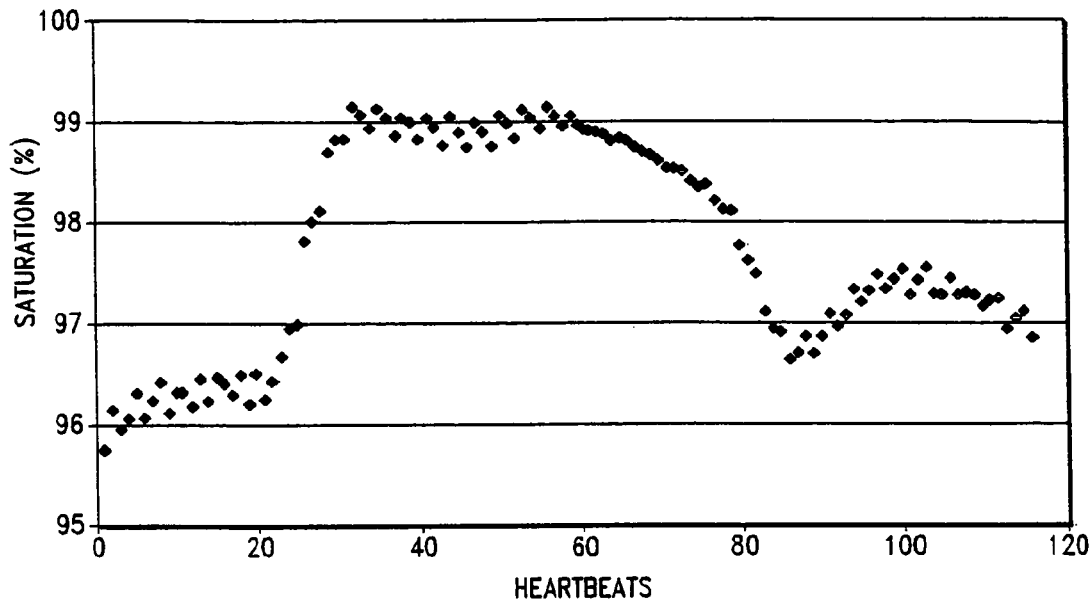
FIG. 30 is graphical illustration of oxygen saturation versus heart rate showing the effects of induced changes in oxygen saturation measured at the right hand.

As is well known in the art, oxygen saturation varies a small amount normally, even in the "steady state". The idea is that this variation can be used to "match" pulses that are of the same saturation, but are "out of phase." That is, they arrive at different parts of the body (opposite hands or hand and foot, for example) at different times. Changes in pH follow similar patterns. Referring to FIGS. 28-30, there are shown induced changes in oxygen saturation caused by a single breath of oxygen, as measured by probes on the toe (FIG. 28), left hand (FIG. 29) and right hand (FIG. 30), respectively.

The concept of induced change in either oxygen saturation of pH is very important. Taking one of more breaths of oxygen will raise one's oxygen saturation. If one is already receiving oxygen therapy, then taking one of more breaths of a higher inspired concentration of oxygen ("richer mixture") will do. Conversely, breath holding, or breathing a gas other that oxygen, such as nitrogen, will decrease your oxygen saturation. For pH, breath holding or breathing a gas mixture containing carbon dioxide will lower your blood pH, whereas rapid breathing will raise your pH. As shown in FIGS. 28-30, the rise starts a few heartbeats earlier on the right hand compared to the left, and the foot is many beats later.

For computing a value for cardiac output, the method is that an index can be generated based on patient's height or body surface area (BSA). The delay in the arrival of a given pulse (identified by saturation or pH) between different parts of the body generates an index for each pair of points. For example, the longer the delay between hand and foot, the lower the cardiac output. The shorter the delay, the higher the cardiac output.

With the addition of the induced saturation change (or pH), one can calculate all these indices more easily (since the change is more noticeable and easier to measure). Importantly, however, there is another index—the time between the breath inspiring the increased oxygen and the first heart beat in which the change is noted. This is the same principle—the shorter this time period, the greater the cardiac output, and the longer the time, the lower the flow.

In summary, giving a subject a single breath of oxygen and continuously measuring the oxygen saturation in an extremity can be used for 3 measurements. First, the time or number of heartbeats from the inspiration to the first change of saturation in the extremity (first pulse that has different saturation from baseline) can be used to compute the cardiac index (and thus cardiac output and stroke volume). Second, the time or number of heartbeats from the beginning of the change in saturation to the maximum change can be used to compute the cardiac ejection fraction. Finally, the time intervals of total time from inspiration until the saturation has returned to baseline, total time from beginning of saturation change to return to baseline and "rebound" in saturation after return to baseline can be used to compute blood volume.

(D-3). Determination of Venous Saturation and Pressure

Determination of arterial oxygen saturation can be determined by pulse oximetry and techniques well delineated in both the patent and medical literature. Hydrostatic changes as described in this application allow the determination of venous saturation and pressure as well.

Place a probe, such as that shown in FIG. 1, on a finger. Make measurements of both total absorbance and pulsatile absorbance. Raise the probe a known distance. Again measure both total absorbance and pulsatile absorbance. Both will be decreased. This is because the pulse amplitude is less because the arterial blood pressure within the probe is less (due to decrease in hydrostatic pressure). However, the total absorbance will also decrease, as the distending pressure in the venous system is less, and hence the veins and venules are smaller. All changes in absorbance can be assumed to be due to changes in blood volume. Saturation is calculated using the ratios of absorbance of distinct wavelengths.

In one embodiment, the central venous pressure (CVP) can be estimated. A probe containing a position sensor is place level with a patient's heart. A second probe, such as the one shown in FIG. 8, also comprising a position sensor is placed on the patient's finger. The patient positions the arm so that the second probe is initially lower than the first probe. The total absorbance measured at the second probe is continuously monitored. The patient's arm is slowly raised, and the rate of change of absorbance of the second probe is computed with respect to the relative displacement to the first probe. When the rate of change changes by a predetermined amount representing an abrupt decrease, the arm position corresponding to the point of central venous drainage has been reached. The CVP can then be calculated by computing the hydrostatic pressure difference between the first probe and the second probe at that arm position. The circuitry shown in FIG. 13 is suitable for use with this embodiment.

(D-4). Determination of Hemoglobin Concentration

Pulse oximeters in clinical use measure hemoglobin absorbance at 2 different wavelengths, commonly 660 and 940 nanometers (nm). Ratiometric analysis of the 2 absorbances at the 2 wavelengths allow determination of the relative amounts of the 2 species of hemoglobin, oxyhemoglobin and deoxyhemoglobin, which normally constitute blood. Standard 2 wavelength oximeters assume that there only these 2 species. Though others may be present, they are usually so in very low concentrations.

As discussed above, the basic equation governing the absorbance of light is Beer's Law:

$$A = E * C * L \qquad \text{Eq. 7}$$

where:
- A=absorbance;
- E=the extinction coefficient;
- L=the path length of light travel; and
- C=concentration of hemoglobin.

The extinction coefficient of the medium through which the light is being transmitted can be thought of as transparency or opacity.

Using this nomenclature, the absorbance of the 660 nm wavelength is $A_{660}$, and the absorbance of the 940 nm wavelength is $A_{940}$. Also, oxy will refer to oxyhemoglobin and deox to deoxyhemoglobin.

Writing out the absorbances in terms of Beer's Law provides:

$$A_{660} = E_{660oxy} * C_{oxy} * L + E_{660deox} * C_{deox} * L \qquad \text{Eq. 8}$$

$$A_{940} = E_{940oxy} * C_{oxy} * L + E_{940deox} * C_{deox} * L \qquad \text{Eq. 9}$$

As sampling can be performed very quickly (optically and electronically), it can be assumed that path length L does not change between 2 successive measurements. Thus, L will cancel out when a division is performed.

$$\frac{A_{660}}{A_{940}} = \frac{E_{660oxy} * C_{oxy} * L + E_{660deox} * C_{deox} * L}{E_{940oxy} * C_{oxy} * L + E_{940deox} * C_{deox} * L}$$

$$= \frac{E_{660oxy} * C_{oxy} + E_{660deox} * C_{deox}}{E_{940oxy} * C_{oxy} + E_{940deox} * C_{deox}}$$

This can then be combined:

$$E_{660oxy} * C_{oxy} * A_{940} + E_{660deox} * C_{deox} * A_{940} = E_{940oxy} * C_{oxy} * A_{660} + E_{940deox} * C_{deox} * A_{660}$$

With rearrangement:

$$E_{660oxy} * C_{oxy} * A_{940} - E_{940oxy} * C_{oxy} * A_{660} = E_{940deox} * C_{deox} * A_{660} - E_{660deox} * C_{deox} * A_{940}$$

$$C_{oxy} * (E_{660oxy} * A_{940} - E_{940oxy} * A_{660}) = C_{deox} * (E_{940deox} * A_{660} - E_{660deox} * A_{940})$$

$$C_{oxy} / C_{deox} = (E_{940deox} * A_{660} - E_{660deox} * A_{940}) / (E_{660oxy} * A_{940} - E_{940oxy} * A_{660})$$

As the absorbances are measured and the extinction coefficients are known experimentally, this allows computation of $C_{oxy}/C_{deox}$. Designating this ratio $R_s$, the oxygen saturation of the blood (S) can be computed and the percentage of the blood that is oxyhemoglobin from the following:

$$S = R_s / (1 + R_s) \qquad \text{Eq. 10}$$

Unfortunately, Eq. 10 only allows determination of the ratio of the 2 species of hemoglobin, not the total concentration of hemoglobin, more commonly termed the "blood count".

The inability of previous attempts to determine hemoglobin concentration from absorbance measurements is because Beer's Law has 2 unknowns, C and L, with only a single measurement, A. As C and L are products, it is impossible to distinguish between them. Forming another equation by making another measurement of absorbance at, for example, a different path length, the new absorbance is simply a multiple of the first, and no new information is gained.

It will thus be appreciated that what is needed is the substitution for either C or L in a way that they are no longer linearly coupled. Since a non-linear result is desirable, multiplication or logarithms would be good choices to manipulate the equation.

An absorbance measurement for hemoglobin can be expressed as:

$$A = C * L * k \qquad \text{Eq. 11}$$

where:
- k=a value based on the extinction coefficients for the wavelength and the oxygen saturation of the blood.

If there is only one species of hemoglobin present, k is the extinction coefficient for that wavelength. Dividing out this known value to provides:

$$A_1 = C * L_1 \qquad \text{Eq. 12}$$

The absorbance measurements can then be taken at a different path length, resulting in different values for $A_1$ as well as $L_1$. However, it is not necessary to repeat measurements, as once absorbance values for a given path length are known, so are the values for all possible path lengths. This also holds for saturation.

$$A_2 = C * L_2 \qquad \text{Eq. 13}$$

Multiplying these Equations 11 and 12 provides:

$$A_1 * A_2 = C * L_1 * C * L_2 = C^2 * L_1 * L_2$$

Further, taking the logarithm of the new equation provides:

$$\log(A_1 * A_2) = 2\log(C) + \log(L_1) + \log(L_2) \qquad \text{Eq. 14}$$

Since the arithmetic operations may be performed in reverse order, this can be rewritten as:

$$\log(L_1) + \log(L_2) = \log(A_1 * A_2) - 2\log(C) \qquad \text{Eq. 15}$$

Taking logarithms first:

$$\log(A_1) = \log(C) + \log(L_1) \qquad \text{Eq. 16}$$

$$\log(A_2) = \log(C) + \log(L_2) \qquad \text{Eq. 17}$$

Next, multiplying these terms provides:

$$\log(A_1) * \log(A_2) = [\log(C) + \log(L_1)] * [\log(C) + \log(L_2)] \qquad \text{Eq. 18}$$

$$= \log^2(C) * \log(C) * [\log(L_1) + \log(L_2)] + \log(L_1) * \log(L_2) \qquad \text{Eq. 19}$$

Substituting the term $[\log(L_1) + \log(L_2)]$ in Equation H2 provides:

$$\log(A_1) * \log(A_2) = \log^2(C) + \log(C) * [\log(A_1 * A_2) - 2\log(C)] + \log(L_1) * \log(L_2) \qquad \text{Eq. 20}$$

Rearrangement provides:

$$\log(A_1) * \log(A_2) = \log(L_1) * \log(L_2) + \qquad \text{Eq. 21}$$
$$\log(C) * \log(A_1 * A_2) - \log(C) *$$
$$2\log(C) + \log^2(L)$$
$$= \log(L_1) * \log(L_2) + \log(C) *$$
$$\log(A_1 * A_2) - 2\log^2(C) + \log^2(C)$$
$$= \log(L_1) * \log(L_2) + \log(C) *$$
$$\log(A_1 * A_2) - \log^2(C)$$

As above, taking the absorbance measurements at different path lengths, will give different values for $A_1$ and $A_2$, as well as $L_1$ and $L_2$. These new values are all multiples of our original $A_1$ and $L_1$. Subscripts 3 and 4 are used to denote these new equations (measurements). The equations thus become:

$$\log(A_1)*\log(A_2)=\log(L_1)*\log(L_2)+\log(C)*\log(A_1*A_2)-\log^2(C) \qquad \text{Eq. 22}$$

$$\log(A_3)*\log(A_4)=\log(L_3)*\log(L_4)+\log(C)*\log(A_3*A_4)-\log^2(C) \qquad \text{Eq. 23}$$

Since the term $\log^2(C)$ occurs in both equations, the term will be eliminated if the equations are subtracted from each other. Thus subtracting Equation 23 from Equation 22 provides:

$$\begin{aligned}\log(A_1)*\log(A_2) &- \log(A_3)*\log(A_4) \\ &= \log(L_1)*\log(L_2) + \log(C)* \\ &\quad \log(A_1*A_2) - \log^2(C) - \\ &\quad [\log(L_3)*\log(L_4) + \log(C)* \\ &\quad \log(A_3*A_4) - \log^2(C)] \\ &= \log(L_1)*\log(L_2) - \log(L_3)* \\ &\quad \log(L_4) + \log(C)* \\ &\quad \log(A_1*A_2) - \log(C)* \\ &\quad \log(A_3*A_4) \\ &= \log(L_1)*\log(L_2) - \log(L_3)* \\ &\quad \log(L_4) + \log(C)* \\ &\quad [\log(A_1*A_2) - \log(A_3*A_4)]\end{aligned} \qquad \text{Eq. 24}$$

These manipulations have broken the linear coupling of C and L, as L occurs as a square in this expression, while C has an exponent of 1. Further, the A terms are in different combinations on opposite sides of the equation. In addition, multiplying either C or L by a given factor results in a different equation, not just a multiple of the same equation. New equations can thus be formed by taking multiples of either L or C. This equation also answers the questions: How can you tell C and L apart? How do you know that C is not half as large and L twice as large? The absorbance measurement is still the same.

If L1 is doubled and C halved, the A values should not change. Thus the left hand side of Equation 24 will not change. For the right hand side, halving C causes the value of the C term to decrease by:

$$\log 2*[\log(A_1*A_2)-\log(A_3*A_4)] \qquad \text{Eq. 25}$$

Since the value of all the L will increase by log 2, the quantity of the L term will be:

$$\begin{aligned}\log(L_1*2)*\log(L_2*2) &- \\ \log(L_3*2)*\log(L_4*2) &= [\log(L_1)+\log 2]* \\ [\log(L_2)+\log 2] - [\log(L_3)+\log 2]*[\log(L_4)+\log 2] &= \\ \log(L_1)*\log(L_2) + \log 2*(\log L_1 + \log L_2) + \\ \log^2 2 - [\log(L_3)*\log(L_4) + \log 2*(\log L_3 + \log L_4) + \\ \log^2 2] &= \log(L_1)*\log(L_2) - \log(L_3)*\log(L_4) + \\ \log 2*(\log L + \log L_2 - \log L_3 - \log L_4)\end{aligned} \qquad \text{Eq. 26}$$

Subtracting the original L term causes a change of:

$$\log 2*(\log L_1+\log L_2-\log L_3-\log L_4) \qquad \text{Eq. 27}$$

This is not equal to the change in the C term (if it were, L could be solved in terms of A), so C and L are not interchangeable.

Referring to Equation 24, it is noted that the log(C) term could be eliminated if new equations with 4 different path lengths were formed and the process repeated. There is nothing preventing this, as any number of equations at different path lengths can be formed, and all will be different.

$$\begin{aligned}\log(A_5)*\log(A_6)-\log(A_7)*\log(A_8) &= \log(L_5)*\log(L_6)- \\ \log(L_7)*\log(L_8)+\log(C)*[\log(A_5*A_6)-\log(A_7*A_8)]\end{aligned} \qquad \text{Eq. 28}$$

To subtract Equation 28 from Equation 24, the coefficients of the log(C) terms must be equal, so Equation 28 is multiplied by the following term:

$$[\log(A_1*A_2)-\log(A_3*A_4)]/[\log(A_5*A_6)-\log(A_7*A_8)]$$

To simplify, constants values that are known or already measured or determined are represented.

$$k_{1234}=\log(A_1)*\log(A_2)-\log(A_3)*\log(A_4) \qquad \text{Eq. 29}$$

$$k_{5678}=\log(A_5)*\log(A_6)-\log(A_7)*\log(A_8) \qquad \text{Eq. 30}$$

$$k_d=[\log(A_1*A_2)-\log(A_3*A_4)]/[\log(A_5*A_6)-\log(A_7*A_8)] \qquad \text{Eq. 31}$$

A new equation is formed by multiplying Equation 28 by $k_d$. This ensures that the log(C) terms are equal. Subtracting this new equation from Equation 24 eliminates the log(C) term:

$$k_{1234}-(k_d*k_{5678})=\log(L_1)*\log(L_2)-\log(L_3)*\log(L_4)-k_d*[\log(L_5)*\log(L_6)-\log(L_7)*\log(L_8)]$$

At this point, an equation with a constant (known number value) on one side, and 4 terms in log(L) on the other is obtained. Equations at 8 path lengths have been used, but these path lengths are all known multiples of each other. Thus, the equations can be expressed as:

$$L_2=L_1*A_2/A_1 \qquad \text{Eq. 32}$$

$$L_3=L_1*A_3/A_1 \qquad \text{Eq. 33}$$

$$L_4=L_1*A_4/A_1 \qquad \text{Eq. 34}$$

$$L_5=L_1*A_5/A_1 \qquad \text{Eq. 35}$$

$$L_6=L_1*A_6/A_1 \qquad \text{Eq. 36}$$

$$L_7=L_1*A_7/A_1 \qquad \text{Eq. 37}$$

$$L_8=L_1*A_8/A_1 \qquad \text{Eq. 38}$$

The equation now becomes:

$$\begin{aligned}k_{1234} - (k_d*k_{5678}) &= \log(L_1)*\log(L_1*A_2/A_1) - \\ &\quad \log(L_1*A_3/A_1)*\log(L_1*A_4/A_1) - \\ &\quad k_d*\log(L_1*A_5/A_1)* \\ &\quad \log(L_1*A_6/A_1)+k_d* \\ &\quad \log(L_1*A_7/A_1)*\log(L_1*A_8/A_1) \\ &= \log(L_1)*[\log(L_1)+\log(A_2/A_1)] - \\ &\quad [\log(L_1)+\log(A_3/A_1)]*[\log(L_1)+\end{aligned} \qquad \text{Eq. 39}$$

-continued $$\log(A_4/A_1)] - k_d * [\log(L_1) +$$
$$\log(A_5/A_1)] * [\log(L_1) +$$
$$\log(A_6/A_1)] + k_d * [\log(L_1) +$$
$$\log(A_7/A_1)] * [\log(L_1) + \log(A_8/A_1)]$$
$$= \log^2(L_1) + \log(L_1) * \log(A_2/A_1)] -$$
$$[\log^2(L_1) + [\log(L_1) * (\log(A_3/A_1) +$$
$$\log(A_4/A_1)] + \log(A_3/A_1) *$$
$$\log(A_4/A_1)] - k_d * [\log^2(L_1) +$$
$$\log(L_1) * (\log(A_5/A_1) +$$
$$\log(A_6/A_1)] + \log(A_5/A_1) *$$
$$\log(A_6/A_1)] + k_d * [\log^2(L_1) +$$
$$[\log(L_1) * (\log(A_7/A_1) +$$
$$\log(A_8/A_1)] + \log(A_7 A_1) *$$
$$\log(A_8/A_1)]$$

As noted, the $\log^2$ terms have coefficient 1. Further, since 2 terms are added while 2 are subtracted they will be eliminated.

Combining all the A terms (which are known) that occur as coefficients, creates $k_{Ac}$. Then, combining all the A terms that occur alone ($k_{Aa}$), the equation becomes:

$$k_{1234} - (k_d * k_{5678}) = \log(L_1) * k_{Ac} + k_{Aa} \qquad \text{Eq. 40}$$

where:

$$\log(L_1) = [k_{1234} - (k_d * k_{5678}) k_{Aa}]/k_{Ac}$$

$$L_1 = \text{antilog}\{[k_{1234} - (k_d * k_{5678}) - k_{Aa}]/k_{Ac}\}$$

This leaves a single unknown, $L_1$. Note that all A values are different, so neither side of the equation should be zero. If this does occur, choice of one or more different A values will guarantee a non-zero result.

Since the equation has been solved for $L_1$, returning to the original equation provides:

$$A_1 = C * L_1 \qquad \text{Eq. 41}$$

$$C = A_1/L_1 \qquad \text{Eq. 42}$$

Now, the concentration of hemoglobin, C, can be solved. An example of a suitable computational algorithm is provided in FIG. 33.

A similar analysis can be performed, varying C instead of L. Maintaining the assumption of only 2 species of hemoglobin, then the wavelength absorbances can be expressed as:

$$A_{660} = A_{660oxy} + A_{660deox} \qquad \text{Eq. 43}$$

$$A_{940} = A_{940oxy} + A_{940deox} \qquad \text{Eq. 44}$$

Furthermore, $$A_{oxy} = A_{660oxy} + A_{940oxy} \qquad \text{Eq. 45}$$

$$A_{deox} = A_{660deox} + A_{940deox} \qquad \text{Eq. 46}$$

and $$A_{oxy} = E_{660oxy} * C_{oxy} * L + E_{940oxy} * C_{oxy} * L \qquad \text{Eq. 47}$$

$$A_{deox} = E_{660deox} * C_{deox} * L + E_{940deox} * C_{deox} * L \qquad \text{Eq. 48}$$

Thus:

$$\frac{A_{660oxy}}{A_{660deox}} = \frac{E_{660oxy} * C_{oxy} * L}{E_{660deox} * C_{deox} * L} \qquad \text{Eq. 49}$$

Since the ratios of $C_{oxy}:C_{deox}$ are known, the equations can be written (canceling L in the process):

$$\frac{A_{660oxy}}{A_{660deox}} = \frac{E_{660oxy} * C_{tot} * S}{E_{660deox} * C_{tot} * (1-S)} = \frac{E_{660oxy} * S}{E_{660deox} * (1-S)} \qquad \text{Eq. 50}$$

Knowing saturation S and the extinction coefficients, permits the ratio, defined as $R_{660}$, to be solved. Returning to the absorbance equations $A_{660oxy}$ and $A_{660deox}$:

$$A_{660oxy} = A_{660} * [R_{660}/(1 + R_{660})]$$

$$A_{660deox} = A_{660} - A_{660oxy}$$

The process can be repeated for the 940 nm absorbance, $A_{940}$. In summary, each of the individual absorbances, i.e., $A_{660oxy}$, $A_{660deox}$, $A_{940oxy}$, $A_{940deox}$ has been determined. Combining them as above provides: $A_{oxy}$, $A_{deox}$, which can be rewritten:

$$A_{oxy} = C_{oxy} * L * (E_{660oxy} + E_{940oxy}) \qquad \text{Eq. 51}$$

$$A_{deox} = C_{deox} * L * (E_{660deox} + E_{940deox}) \qquad \text{Eq. 52}$$

At this point it is convenient to divide out the known extinction coefficient values to get $A'_{oxy}$ and $A'_{deox}$ which remain known values:

$$A'_{oxy} = C_{oxy} * L \qquad \text{Eq. 53}$$

$$A'_{deox} = C_{deox} * L \qquad \text{Eq. 54}$$

As above, these equations can be manipulated with multiplication and logarithms. Multiplying first:

$$A'_{oxy} * A'_{deox} = C_{oxy} * L * C_{deox} * L = C_{oxy} * C_{deox} * L^2 \qquad \text{Eq. 55}$$

Then taking the logarithm:

$$\log(A'_{oxy} * A'_{deox}) = \log(C_{oxy}) + \log(C_{deox}) + 2\log(L) \qquad \text{Eq. 56}$$

This can be rewritten as:

$$\log(C_{oxy}) + \log(C_{deox}) = \log(A'_{oxy} * A_{deox}) - 2\log(L) \qquad \text{Eq. 57}$$

The operations can now be performed in reverse order.

Taking the logarithms first:

$$\log(A'_{oxy}) = \log(C_{oxy}) + \log(L) \qquad \text{Eq. 58}$$

$$\log(A'_{deox}) = \log(C_{deox}) + \log(L) \qquad \text{Eq. 59}$$

Now multiplying these terms:

$$\log(A'_{oxy}) * \log(A^*_{deox}) = [\log(C_{oxy}) + \log(L)] * \qquad \text{Eq. 60}$$
$$[\log(C_{deox}) + \log(L)]$$
$$= \log(C_{oxy}) * \log(C_{deox}) + \log(L) *$$
$$[\log(C_{oxy}) + \log(C_{deox})] + \log^2(L)$$

Now substituting for $\log(C_{oxy})+\log(C_{deox})$ from Equation 57 into Equation 60:

$$\log(A'_{oxy})*\log(A'_{deox})=\log(C_{oxy})*\log(C_{deox})+\log(L)*[\log(A'_{oxy}*A'_{deox})-2\log(L)]+\log^2(L) \quad \text{Eq. 61}$$

Rearranging this equation provides:

$$\log(A'_{oxy})*\log(A'_{deox}) = \log(C_{oxy})*\log(C_{deox}) + \log(L)* \quad \text{Eq. 62}$$
$$\log(A'_{oxy}*A'_{deox}) - \log(L)*$$
$$2\log(L) + \log^2(L)$$
$$= \log(C_{oxy})*\log(C_{deox}) +$$
$$\log(L)(A'_{oxy}*A'_{deox}) - 2\log^2(L) +$$
$$\log^2(L)$$
$$= \log(C_{oxy})*\log(C_{deox}) + \log(L)*$$
$$\log(L)*\log(A'_{oxy}*A'_{deox}) - \log^2(L)$$

Taking absorbance measurements at a different saturation gives different values for $A'_{oxy}$ and $A'_{deox}$, as well as $C_{oxy}$ and $C_{deox}$. As above, once absorbance values for a given saturation are known, they are known for all possible saturations.

Therefore, $A'_{oxy}$ and $A'_{deox}$ can be calculated for a different saturation, and performing the multiplication and logarithm manipulations will generate a new equation. The original values of $A'_{oxy}$ and $A'_{deox}$ are specified as $A_{oxy1}$ and $A_{deox1}$, and the new values, $A_{oxy2}$ and $A_{deox2}$.

The equations thus become:

$$\log(A_{oxy1})*\log(A_{deox1})=\log(C_{oxy1})*\log(C_{deox1})+\log(L)*\log(A_{oxy1}*A_{deox1})-\log^2(L) \quad \text{Eq. 63}$$

$$\log(A_{oxy2})*\log(A_{deox2})=\log(C_{oxy2})*\log(C_{deox2})+\log(L)*\log(A_{oxy2}*A_{deox2})-\log^2(L) \quad \text{Eq. 64}$$

Since the term $\log^2(L)$ occurs in both equations, it will be eliminated by subtracting the equations from each other. Thus, subtracting Equation 64 from Equation 63 provides:

$$\log(A_{oxy1})*\log(A_{deox1}) - \log(A_{oxy2})*\log(A_{deox2}) = \quad \text{Eq. 65}$$
$$\log(C_{oxy1})*\log(C_{deox}) + \log(L)*\log(A_{oxy1}*A_{deox}) -$$
$$\log^2(L) - [\log(C_{oxy2})*\log(C_{deox2}) + \log(L)*\log(A_{oxy2}*A_{deox2}) -$$
$$\log^2(L) = \log(C_{oxy1})*\log(C_{deox1}) -$$
$$\log(C_{oxy2})*\log(C_{deox2}) + \log(L)*\log(A_{oxy1}*A_{deox1}) -$$
$$\log(L)*\log(A_{oxy2}*A_{deox2})$$

$$= \log(C_{oxy1})*\log(C_{deox1}) - \log(C_{oxy2})*\log(C_{deox2}) + \quad \text{Eq. 66}$$
$$\log(L)*[\log(A_{oxy1}*A_{deox1}) - \log(A_{oxy2}*A_{deox2})]$$

Referring to Eq. 66, it can be seen that the log(L) term could be eliminated according to the invention, by forming new equations with 2 different saturations and repeating the process. Again, any number of equations at different saturations can be formed, and all will be different.

Using reference numerals 3 and 4 to denote these new relationships, provides:

$$\log(A_{oxy3})*\log(A_{deox3})-\log(A_{oxy4})*\log(A_{deox4})=\log(C_{oxy3})$$
$$*\log(C_{deox3})-\log(C_{oxy4})*\log(C_{deox4})+\log(L)*[\log(A_{oxy3}*A_{deox3})$$
$$-\log(A_{oxy4}*A_{deox4})] \quad \text{Eq. 67}$$

To subtract Equation 67 from Equation 66, the coefficients of the log(L) terms must be equal, so Equation 67 can be multiplied by the following:

$$[\log(A_{oxy1}*A_{deox1})-\log(A_{oxy2}*A_{deox2})]/$$
$$[\log(A_{oxy3}*A_{deox3})-\log(A_{oxy4}*A_{deox4})]$$

To simplify, representing by values of constants that are known or already measured or determined:

$$k_{12}=\log(A_{oxy1})*\log(A_{deox1})-\log(A_{oxy2})*\log(A_{deox2}) \quad \text{Eq. 68}$$

$$k_{34}=\log(A_{oxy3})*\log(A_{deox3})-\log(A_{oxy4})*\log(A_{deox4})k_m \quad \text{Eq. 69}$$

$$=[\log(A_{oxy1}*A_{deox1})-\log(A_{oxy2}*A_{deox2})]/$$
$$[\log(A_{oxy3}*A_{deox3})-\log(A_{oxy4}*A_{deox4})] \quad \text{Eq. 70}$$

A further equation is formed by multiplying Equation 67 by $k_m$. This ensures that the log(L) terms are equal. Subtracting this new equation from Equation 66 eliminates the log(L) term:

$$k_{12}-(k_m*k_{34})=\log(C_{oxy1})*\log(C_{deox1})-\log(C_{oxy2})*$$
$$\log(C_{deox2})-k_m*[\log(C_{oxy3})*\log(C_{deox3})-$$
$$\log(C_{oxy4})*\log(C_{deox4})] \quad \text{Eq. 71}$$

At this point, the equation has a constant on one side, and 4 terms in $\log^2 C$ on the other. Equations at 4 values of saturation have been used, but these saturation values are all known. Thus:

$$C_{oxy1}=C_{tot}*S_1 \quad \text{Eq. 72}$$

$$C_{deox1}=C_{tot}*(1-S_1) \quad \text{Eq. 73}$$

$$C_{oxy2}=C_{tot}*S_2 \quad \text{Eq. 74}$$

$$C_{deox2}=C_{tot}*(1-S_2) \quad \text{Eq. 75}$$

$$C_{oxy3}=C_{tot}*S_3 \quad \text{Eq. 76}$$

$$C_{deox3}=C_{tot}*(1-S_3) \quad \text{Eq. 77}$$

$$C_{oxy4}=C_{tot}*S_4 \quad \text{Eq. 78}$$

$$C_{deox4}=C_{tot}*(1-S_4) \quad \text{Eq. 79}$$

The equation now becomes:

$$k_{12}-(k_m*k_{34})=\log(C_{tot}*S_1)*\log(C_{tot}*(1-S_1))-$$
$$\log(C_{tot}*S_2)$$
$$*\log(C_{tot}*(1-S_2))-k_m*\log(C_{tot}*S_3)*\log(C_{tot}*(1-S_3))+$$
$$k_m$$
$$*\log(C_{tot}*S_4)*\log(C_{tot}*(1-S_4)) \quad \text{Eq. 80}$$

Inspecting the 4 terms on the right hand side of this equation individually:

$$\log(C_{tot}*S_1)*\log(C_{tot}*(1-S_1)) = [\log(C_{tot}) + \log(S_1)]* \quad \text{Eq. 81}$$
$$[\log(C_{tot}) + \log(1-S_1)]$$
$$= \log^2(C_{tot}) + \log(C_{tot})*\log(S_1) +$$
$$\log(C_{tot})*\log(1-S_1)] +$$
$$\log(S_1)*\log(1-S_1)$$
$$= \log^2(C_{tot}) + \log(C_{tot})*[\log(S_1) +$$
$$\log(1-S_1)] + \log(S_1)*$$
$$\log(1-S_1)$$

-$\log(A_{oxy4}*A_{deox4})] \quad \text{Eq. 67}$

Note that the log² term has 1 as coefficient. Since there are 4 symmetrical terms, 2 adding and 2 subtracting, the log² terms will cancel out i.e., $$k_{12}-(k_m*k_{34})=\log(C_{tot})*[\log(S_1)+\log(1-S_1)]+\log(S_1)$$

$$*\log(1-S_1)-\log(C_{tot})*[\log(S_2)+\log(1-S_2)]-\log(S_2)$$

$$*\log(1-S_2)-k_m*[\log(C_{tot})*[\log(S_3)+\log(1-S_3)]+\log(S_3)$$

$$*\log(1-S_3)]+k_m*[\log(C_{tot})*[\log(S_4)+\log(1-S_4)]+\log(S_4)$$

$$*\log(1-S_4)]\qquad\text{Eq. 82}$$

All terms containing only log(S) or log(1−S) are known, so they can be collected and replaced with $k_s$. Further, collecting all terms with $C_{tot}$ provides:

$$k_{12}-(k_m*k_{34})=\qquad\text{Eq. 83}$$
$$\log(C_{tot})*[[\log(S_1)+\log(1-S_1)]-[\log(S_2)+\log(1-S_2)]-$$
$$k_m*[\log(S_3)+\log(1-S_3)]+k_m*[\log(S_4)+\log(1-S_4)]]+k_s$$

Again, all terms with log(S) or log(1−S) are known, so they can be collected and replaced with $k_{cs}$. Note that $k_{cs}$ cannot be zero, as the saturations are all different. The equation thus becomes:

$$k_{12}-(k_m*k_{34})=\log(C_{tot})*k_{cs}+k_s$$

where:

$$k_{12}-(k_m*k_{34})-k_s=\log(C_{tot})*k_{cs}$$

$$\log(C_{tot})=[k_{12}-(k_m*k_{34})-k_s]/k_{cs}$$

$$C_{tot}=\text{antilog}\{[k_{12}-(k_m*k_{34})-k_s]/k_{cs}\}$$

In summary, $C_{tot}$, the concentration of hemoglobin, has been determined based entirely on known or measured values. It will be appreciated that, while this analysis assumes only 2 species of hemoglobin, the determinations can be made with additional species present by utilizing additional wavelengths of light.

If the saturation is known, the determination can be made using a single absorbance measurement from a single wavelength of light. For illustration, absorbance employing a wavelength of 660 nm is detailed below.

$$A_{660}=A_{660oxy}+A_{660deox}\qquad\text{Eq. 85}$$

$$A_{660}=E_{660oxy}*C_{oxy}*L+E_{660deox}*C_{deox}*L$$

$$\frac{A_{660oxy}}{A_{660deox}}=\frac{E_{660oxy}*C_{oxy}*L}{E_{660deox}*C_{deox}*L}$$

Rewriting this equation to incorporate the known saturation S gives:

$$\frac{A_{660oxy}}{A_{660deox}}=\frac{E_{660oxy}*C_{tot}*S}{E_{660deox}*C_{tot}*(1-S)}=\frac{E_{660oxy}*S}{E_{660deox}*(1-S)}\qquad\text{Eq. 86}$$

As above, this equation can be solved, providing the ratio $R_{660}$. Returning and solving for the actual absorbances $A_{660oxy}$ and $A_{660deox}$ provides:

$$A_{660oxy}=A_{660}*[R_{660}/(1+R_{660})]$$

$$A_{660deox}=A_{660}-A_{660oxy}\qquad\text{Eq. 87}$$

Finally, dividing out the known extinction coefficient values provides $A'_{660oxy}$ and $A'_{660deox}$:

$$A'_{660oxy}=C_{oxy}*L\qquad\text{Eq. 88}$$

$$A'_{660deox}=C_{deox}*L\qquad\text{Eq. 89}$$

At this point, the same algorithm as above will work for the single wavelength, allowing the substitution of the 660 nm absorbances for the total absorbances. That is, substituting $A'_{660oxy}$ for $A'_{oxy}$, etc. It will also be appreciated that performing analysis by both methods (manipulating C or manipulating L) independently can be used to verify results obtained by either technique.

An alternative measurement method utilizing venous absorbance follows. The technique is equally suitable for arterial measurements. Two probes, such as shown in FIG. 8, are placed on two separate digits. These probes should be of fixed or at least known dimensions. The probes can be on one hand or both hands, as in FIG. 9. Raising the hand well above the heart causes the venous absorbance signal to fall to near zero, as height of the probes will cause the pressure in the venous system within the probes to be below the CVP. Slowly lowering the digits will cause the veins to no longer be collapsed at some point. While this should happen at the same point for both probes, it is not essential to the technique. As the lowering of the digits continues, the volume and pressure will rise above zero, and will continue rising as the digits are lowered. The important concept is that the absorbances will not be the same in both probes. Two dissimilar fingers, such as a thumb and fifth finger can be chosen, but in any case absorbances will not be identical even between similar fingers. Circuitry such as that shown in FIG. 13, may be used to facilitate the measurements.

Since the dimensions of the probes are known, the concentration C of the blood within the probes can be imputed. Of course, this C will be much higher than the true concentration since the space within the probes is occupied by other tissue and only a small part is blood. If H represents the hydrostatic distance that the probes have moved since the beginning of venous absorbance (this is convenient to establish a zero point for a graph), then a graph of H vs. C will be different for the two probes, as the amount of absorbing blood within the two probes is different. Given that the true concentration of hemoglobin in the blood is the same throughout the vascular system, there is a further distance D (a fraction of H) that a first probe with the lower concentration would have to be physically lowered in order to achieve the same concentration as the second probe. Preferably, the dimensions of the probes should be minimized to increase the accuracy of the concentration estimates, since the path length of the probes is much greater than the path length of blood. For example, halving the diameter of the probes doubles the measured concentration.

Since the true path length of non-scattering blood absorbance is very small, the point where H and (H+D) are in the same ratio as the imputed concentrations yields the true concentrations. That is, if the concentration ratios are 1:2 (twice as much absorbance in one probe), the true concentrations would be where H and D are equal. The actual concentration of hemoglobin is that at point (H,C). The further length D represents the additional non-blood path length through the other probe. Note that this C occurs at only one point. Also note that H is not the true path length, but C is in fact the true concentration.

Advantageously, this technique can be repeated many times for one arm movement, can be used for both arterial and venous measurements, and arterial and venous measurements can be done simultaneously, and checked against each other.

In another embodiment of the invention, hemoglobin concentration can be derived by taking ratios of absorbance at different pressures. Pressure is equal to dynes divided by the square of the path length, i.e., $$P=D/L^2 \qquad \text{Eq. 90}$$

and, as indicated above, Beer's Law is:

$$A=E*C*L \qquad \text{Eq. 91}$$

Multiplying P by $A^2$ provides:

$$E^2*C^2*D \qquad \text{Eq. 92}$$

Successive measurements give $E^2*C^2*D_1, E^2*C^2*D_2, \ldots E^2*C^2*D_x$ from which ratios can be formed. Next, the values $P+A^2$ and $P^{-1}+A^2$ are known quantities, and substituting Beer's Law and the pressure to length relationship allows the latter to be written as:

$$L^2/D^2+E^2*C^2*L^2 \qquad \text{Eq. 93}$$

Dividing by $L^2$ provides:

$$L^2*(D^{-2}+E^2*C^2) \qquad \text{Eq. 94}$$

As before, successive measurements gives values $L_1^2*(D_1^{-2}+E^2*C^2), L_2^2*(D_2^{-2}+E^2*C^2), \ldots L_x^2*(D_x^{-2}+E^2*C^2)$. Since the path length ratios are known, the values can be divided by L and the successive values can be divided to give the ratio:

$$(D_1^{-2}+E^2*C^2)/(D_2^{-2}+E^2*C^2)=m \qquad \text{Eq. 95}$$

Further, $D_1^{-2}/D_2^{-2}$ can be expressed in terms of $D_2/D_1$, which, as discussed above, is a known ratio. As $E^2*C^2$ is a constant, equation 95 is taking a known ratio, adding a constant to the numerator and denominator, and arriving at another known ratio. Thus, the value of the constant can be determined uniquely and precisely. As E is known, this allows determination of C, the concentration of hemoglobin. Once C is determined, A=ECL allows computation of L, the path length and determination of L allows the computation of D as validation.

(D-5). Determination of pH and Acid-Base Balance

Figure 34:
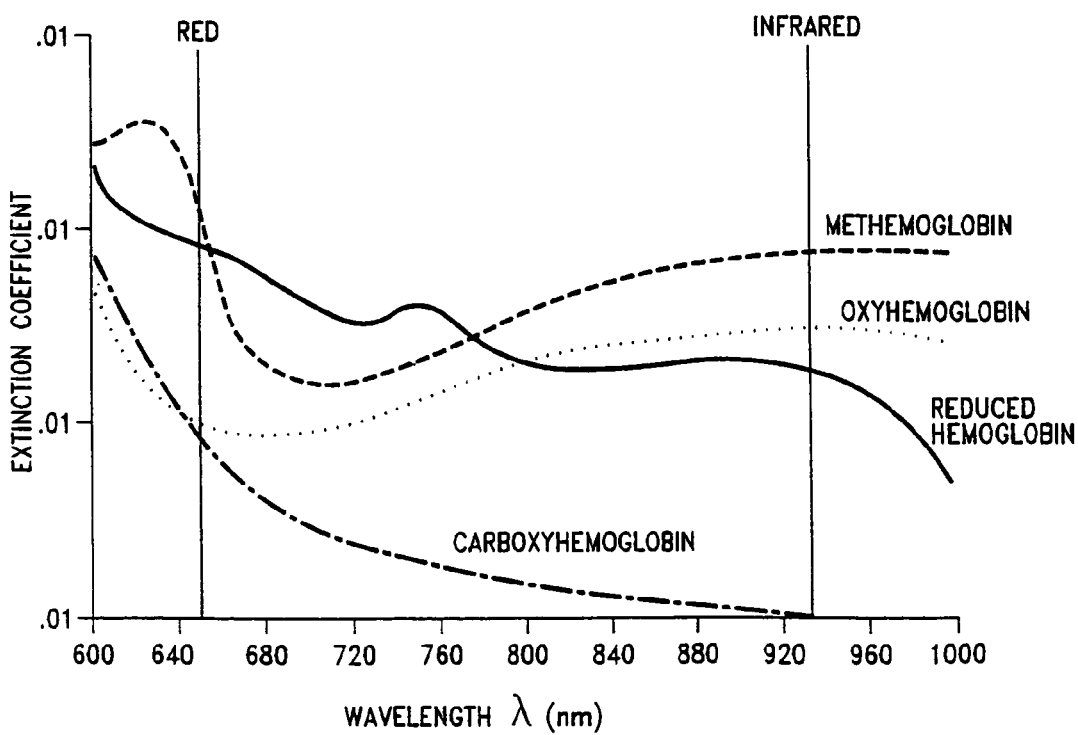
FIG. 34 is a graphical illustration of optical extinction curves of four species of hemoglobin at light wavelengths in the range of 600 to 950 nm.

This probes and methods of this invention allow the pH and acid-base balance of a patient's blood to be determined noninvasively, continuously and in real time. Generally, a probe such as those described above, containing one or more sources of emitted light is used, for example as shown in FIGS. 5 and 8. Preferably, the invention utilizes light in the visible and near-infrared spectra, but other wavelengths could be successfully used. Detection of transmitted light is made by a photodetector. Suitable circuitry is shown in FIGS. 11 and 14, for example. Determination of absorbance of the emitted light is done using Beer's law. The emission, detection, and determination of absorbance described are all similar to that used in pulse oximeters, common in modern hospital settings. Using either pulse oximetry (filtering out all non-pulsatile signal components) or conventional spectrophotometry, identification of methemoglobin, oxyhemoglobin, deoxyhemoglobin, and carboxyhemoglobin, species of human hemoglobin, is made by utilizing known absorbance spectrums, such as those shown in FIG. 34.

Figure 35:
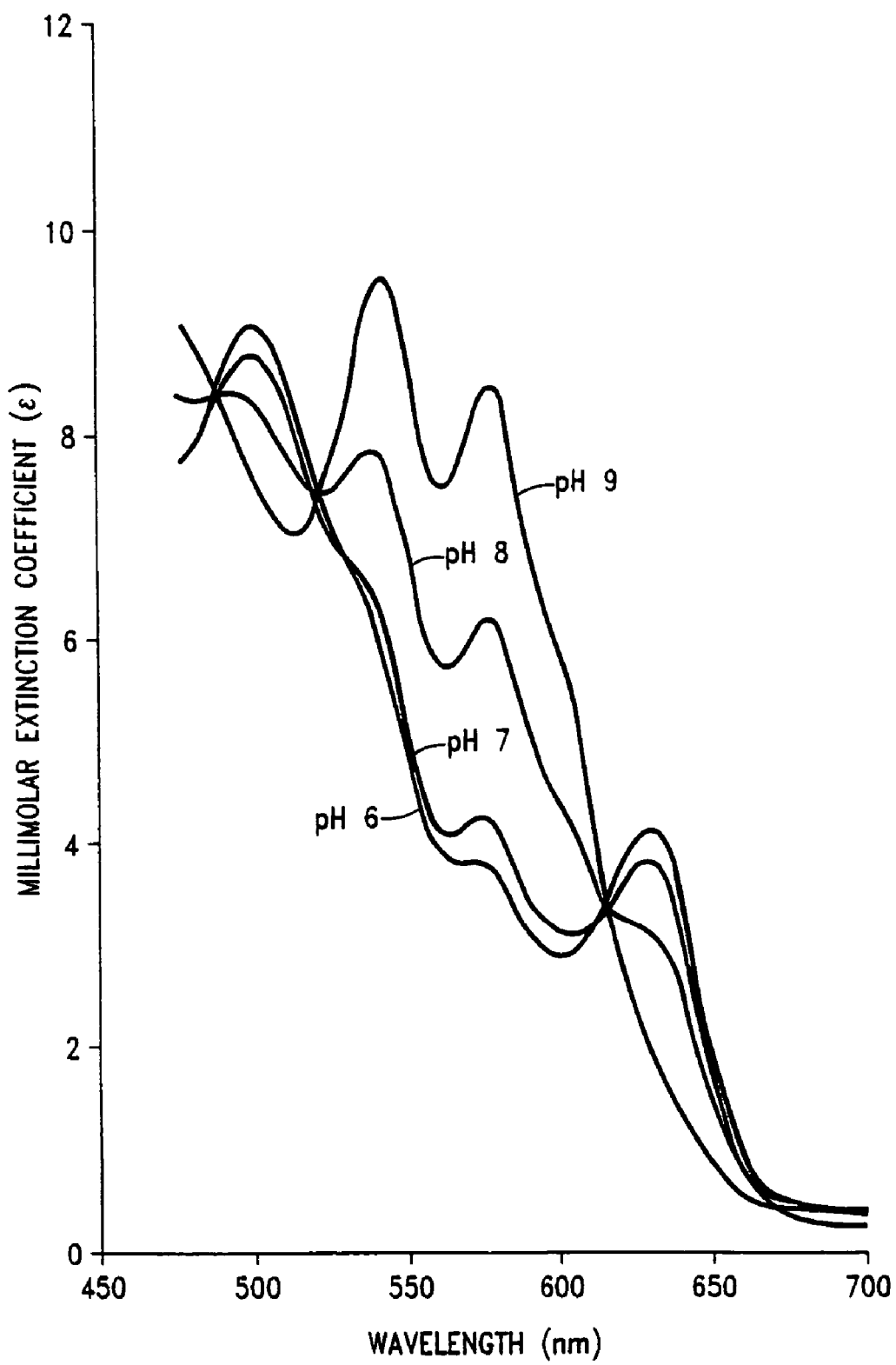
FIG. 35 is a graphical illustration of optical extinction curves for hemoglobin A at four different pH values and at light wavelengths in the range of 500 to 600 nm.

The absorbance spectra of oxyhemoglobin, deoxyhemoglobin, and carboxyhemoglobin, the more common hemoglobin species, are conventionally understood to be essentially unaffected by acid-base balance over the most commonly used spectrophotometric range of 650-1000 nm. However, all proteins and organic molecules are affected by pH to some extent. FIG. 35 shows the absorption spectrum of hemoglobin A (deoxyhemoglobin) between 500 and 650 nm for 4 different pH values—pH 6, 7, 8, and 9. It can be clearly seen that pH does have a significant effect on the absorption spectrum. Thus, the spectrum of hemoglobin species is in fact altered by pH in the clinical range. The changes are small, and have largely been ignored by the prior art because they are too small to be considered clinically important for oxygen saturation measurements.

Figure 36:
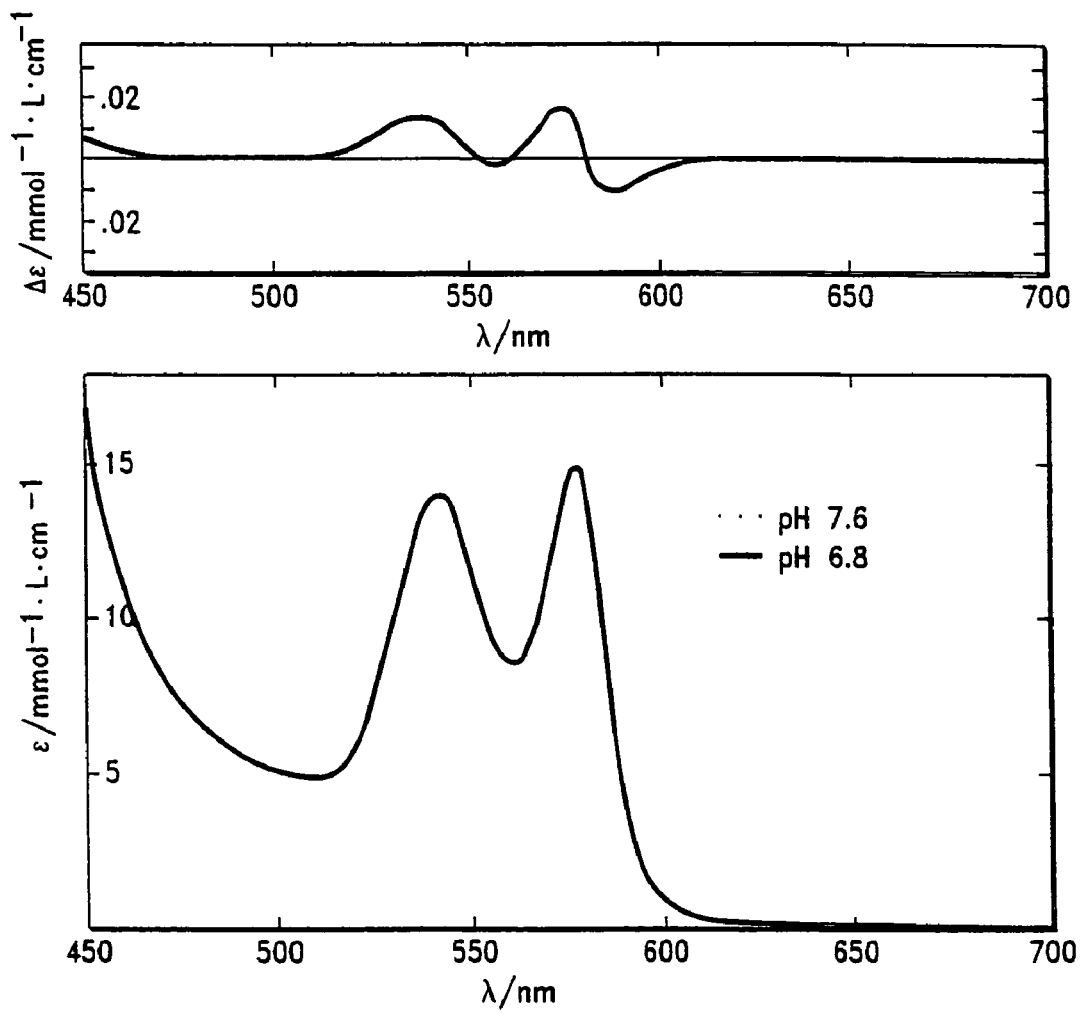
FIG. 36 is an absorption spectrum for oxyhemoglobin between measurements at pH 7.6 and pH 6.8.

While many wavelengths may be affected, specific alterations have been found at wavelengths 535, 577, and 600 nm. For example, oxyhemoglobin shows absorption peaks at 535 and 577 nm that are greater at higher pH, while the trough near 600 nm is slightly deeper as illustrated in FIG. 36. The upper panel is a difference spectrum magnified 10-fold to more clearly illustrate the absorption pattern. The total hemoglobin concentration in both curves was normalized arbitrarily at a wavelength of 506 nm. It is estimated that this produces a difference in calculated saturation of about 3% from pH 7.6 to pH 6.8. Thus, saturation measurements accurate to 0.1% should define pH to within 0.05 pH units.

Ratiometric techniques similar to pulse oximetry can be used to exploit these spectral differences in order to determine pH of the blood. As pH has relatively little effect at the near infrared wavelengths, performing pulse oximetry using two wavelengths such as 660 and 940 can be used to determine the "true" oxygen saturation of the blood (for now, assuming only the two species oxyhemoglobin and deoxyhemoglobin). An additional simultaneous measurement of at least one other wavelength—one known to be affected by pH, for example 535 or 577 nm—is performed. By making pair-wise comparisons of the ratios at all the wavelengths, the pH can be measured from the saturation values. Preferably, a multi-wavelength spectrophotometer allows multiple comparisons.

Figure 31:
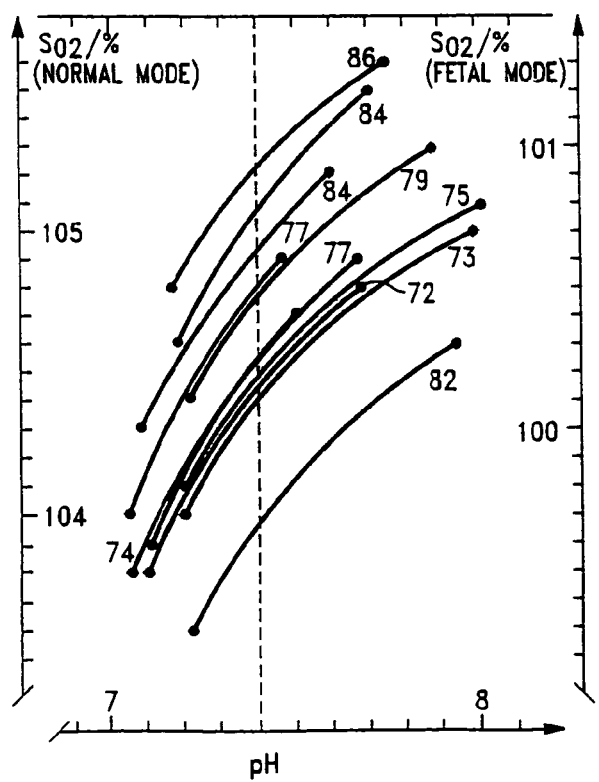
FIGS. 31 and 32 are graphical illustrations of oxygen saturation ($SO_2$) versus pH showing the effect of plasma pH on oxygen saturation measurements for umbilical cord blood samples equilibrated with 100% oxygen.
Figure 32:
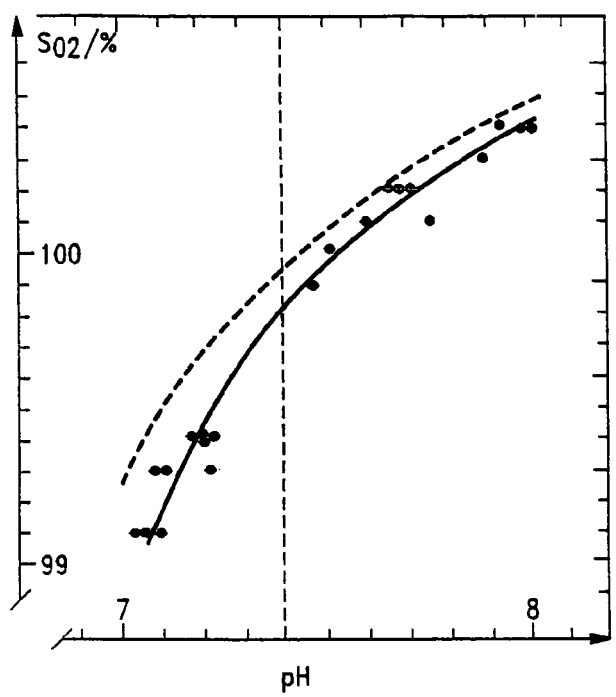
Figure 37:
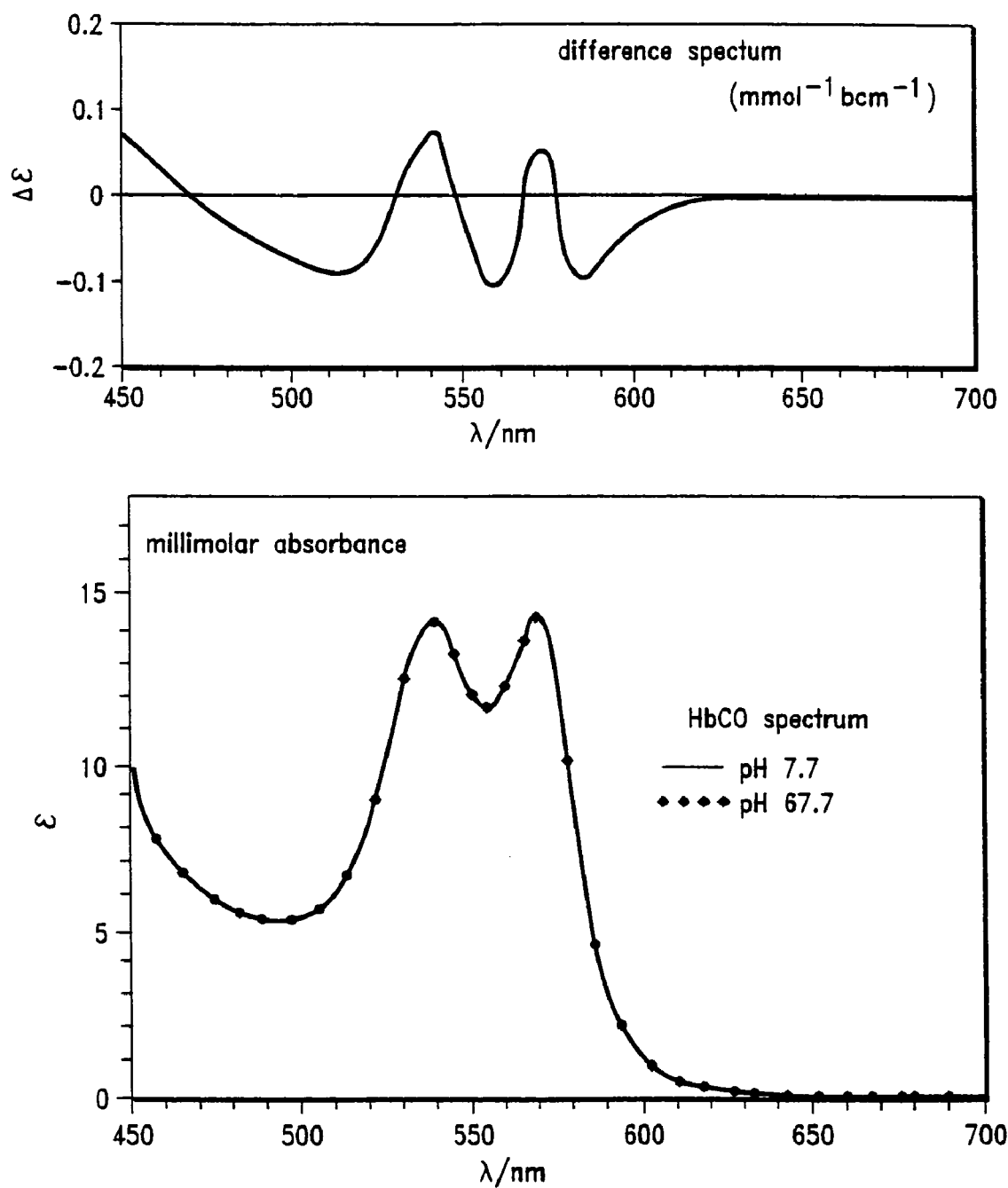
FIG. 37 is an absorption spectrum for carboxyhemoglobin between measurements at pH 7.6 and pH 6.8.

Similarly, there are small pH-dependent changes in the absorption spectra of carboxyhemoglobin and fetal hemoglobin. A pH effect has been determined on the carboxyhemoglobin (COHb) absorption spectrum. There is a bias of about 3% COHb per pH unit if pH is not taken into account. FIG. 37 illustrates an absorption spectrum and shows that the absorption peaks at 535 and 577 nm are higher, and the trough near 600 nm is slightly lower, at the higher pH value. Thus, the use of ratiometric determinations of predicted versus actual fraction of carboxyhemoglobin can be used to calculate pH of blood noninvasively using oximetric techniques. Differences have been found in the absorption spectra of species of fetal hemoglobin due to pH, especially fetal carboxyhemoglobin. This is illustrated in FIGS. 31 and 32. Accordingly, noninvasive pH determinations can be made from its absorption ratios.

As mentioned above, the absorbance spectra of oxyhemoglobin, deoxyhemoglobin, and carboxyhemoglobin, the more common hemoglobin species, are affected relatively little by acid-base balance. Another embodiment of the invention exploits the optical spectrum of methemoglobin, which is very sensitive to pH in the physiologic range. Specifically, at pH 7 and below, the spectrum of aquomethemoglobin with maximum at wavelength 630 nm is observed. At alkaline pH, the spectrum of hydroxymethemoglobin with disappearance of the maximum at 630 nm is seen. In terms of electron paramagnetic resonance spectra reflecting the electronic spin state of the iron atom, in aquomethemoglobin the iron atom has a "high spin" state and is strongly paramagnetic. With increasing pH and the formation of hydroxymethemoglobin, the iron atom goes to a low spin state, accompanied by a decrease in atomic radius. Since methemoglobin exists as an equilibrium mixture of structures, the relative amount of each can be used to determine the pH of the medium, blood.

Referring now to Table I, there is shown a table by which the extinction coefficients for methemoglobin for selected wavelengths of light can be determined, since the absorbance varies with the acid-base balance of the blood.

TABLE I

| Species | Wavelength | | | | |
|---|---|---|---|---|---|
| | 540 | 560 | 570 | 576 | 640 |
| Oxyhemoglobin | 1.53 | 0.906 | 1.23 | 1.65 | 0.015 |
| deoxyhemoglobin | 1.08 | 1.34 | 1.16 | 1.01 | 0.115 |
| carboxyhemoglobin | 1.44 | 1.22 | 1.51 | 1.13 | 0.023 |

| pH | Methemoglobin | | | | |
|---|---|---|---|---|---|
| 6.2 | 0.609 | 0.373 | 0.355 | 0.358 | 0.412 |
| 6.4 | 0.610 | 0.374 | 0.356 | 0.360 | 0.410 |
| 6.6 | 0.613 | 0.379 | 0.365 | 0.370 | 0.409 |
| 6.8 | 0.623 | 0.389 | 0.380 | 0.385 | 0.406 |
| 7.0 | 0.638 | 0.405 | 0.400 | 0.406 | 0.401 |
| 7.2 | 0.658 | 0.424 | 0.425 | 0.433 | 0.393 |
| 7.4 | 0.682 | 0.450 | 0.455 | 0.465 | 0.380 |
| 7.6 | 0.710 | 0.481 | 0.492 | 0.507 | 0.360 |
| 7.8 | 0.746 | 0.520 | 0.537 | 0.558 | 0.324 |
| 8.0 | 0.788 | 0.567 | 0.590 | 0.620 | 0.306 |
| 8.2 | 0.835 | 0.616 | 0.647 | 0.682 | 0.280 |
| 8.4 | 0.882 | 0.665 | 0.703 | 0.745 | 0.254 |
| 8.6 | 0.926 | 0.710 | 0.755 | 0.800 | 0.230 |
| 8.8 | 0.964 | 0.749 | 0.801 | 0.850 | 0.208 |

From the information in Table I, Tables IIA and IIB can be created, which gives the ratios of the extinction coefficients for methemoglobin at the various pH values. To determine the pH using Tables IIA and IIB, one first determines either the absorbance due to methemoglobin at each wavelength of interest, or the percentage of methemoglobin compared to other hemoglobin species. These determinations can be done using techniques described elsewhere in this application, or in other works. Once this has been done, the ratio of absorbances at the different wavelengths can be used to compute the pH.

For example, if the ratio of absorbance of methemoglobin for a 540 nm wavelength light source to the absorbance of methemoglobin for a 560 wavelength light source is 1.633, the pH is 6.2. If the ratio is instead 1.516, the pH is approximately 7.4. Similar calculations can be made for other wavelengths, and the results compared to ensure accuracy.

TABLE IIA

| | Methemoglobin | | | | |
|---|---|---|---|---|---|
| pH | 540/560 | 540/570 | 540/576 | 540/640 | 560/570 |
| 6.2 | 1.633 | 1.715 | 1.701 | 1.478 | 1.051 |
| 6.4 | 1.631 | 1.713 | 1.694 | 1.488 | 1.051 |
| 6.6 | 1.617 | 1.679 | 1.657 | 1.499 | 1.038 |
| 6.8 | 1.602 | 1.639 | 1.618 | 1.534 | 1.024 |
| 7.0 | 1.575 | 1.595 | 1.571 | 1.591 | 1.013 |
| 7.2 | 1.552 | 1.548 | 1.520 | 1.674 | 0.998 |
| 7.4 | 1.516 | 1.499 | 1.467 | 1.795 | 0.989 |
| 7.6 | 1.476 | 1.443 | 1.400 | 1.972 | 0.978 |
| 7.8 | 1.435 | 1.389 | 1.337 | 2.302 | 0.968 |

TABLE IIA-continued

| | Methemoglobin | | | | |
|---|---|---|---|---|---|
| pH | 540/560 | 540/570 | 540/576 | 540/640 | 560/570 |
| 8.0 | 1.390 | 1.336 | 1.271 | 2.575 | 0.961 |
| 8.2 | 1.356 | 1.291 | 1.224 | 2.982 | 0.952 |
| 8.4 | 1.326 | 1.255 | 1.184 | 3.472 | 0.946 |
| 8.6 | 1.304 | 1.226 | 1.158 | 4.026 | 0.940 |
| 8.8 | 1.287 | 1.203 | 1.134 | 4.635 | 0.935 |

TABLE IIB

| | Methemoglobin | | | | |
|---|---|---|---|---|---|
| pH | 560/576 | 560/540 | 570/576 | 570/640 | 576/640 |
| 6.2 | 1.042 | 0.905 | 0.992 | 0.862 | 0.869 |
| 6.4 | 1.039 | 0.912 | 0.989 | 0.868 | 0.878 |
| 6.6 | 1.024 | 0.927 | 0.986 | 0.892 | 0.905 |
| 6.8 | 1.010 | 0.958 | 0.987 | 0.936 | 0.948 |
| 7.0 | 0.998 | 1.010 | 0.985 | 0.998 | 1.012 |
| 7.2 | 0.979 | 1.079 | 0.982 | 1.081 | 1.102 |
| 7.4 | 0.968 | 1.184 | 0.978 | 1.197 | 1.224 |
| 7.6 | 0.949 | 1.336 | 0.970 | 1.367 | 1.408 |
| 7.8 | 0.932 | 1.605 | 0.962 | 1.657 | 1.722 |
| 8.0 | 0.915 | 1.853 | 0.952 | 1.928 | 2.026 |
| 8.2 | 0.903 | 2.200 | 0.949 | 2.311 | 2.436 |
| 8.4 | 0.893 | 2.618 | 0.944 | 2.768 | 2.933 |
| 8.6 | 0.888 | 3.087 | 0.944 | 3.283 | 3.478 |
| 8.8 | 0.881 | 3.601 | 0.942 | 3.851 | 4.087 |

In these embodiments of the invention, it is not necessary to compute the actual concentration of any hemoglobin species. Indeed, merely the ratio or relative amount compared to other species yields sufficient information to determine blood pH and acid-base balance. In general, the separate identification of n species will require at least n different wavelengths of light to be used. If desired, more than the minimum number of wavelengths may be used.

Figure 38:
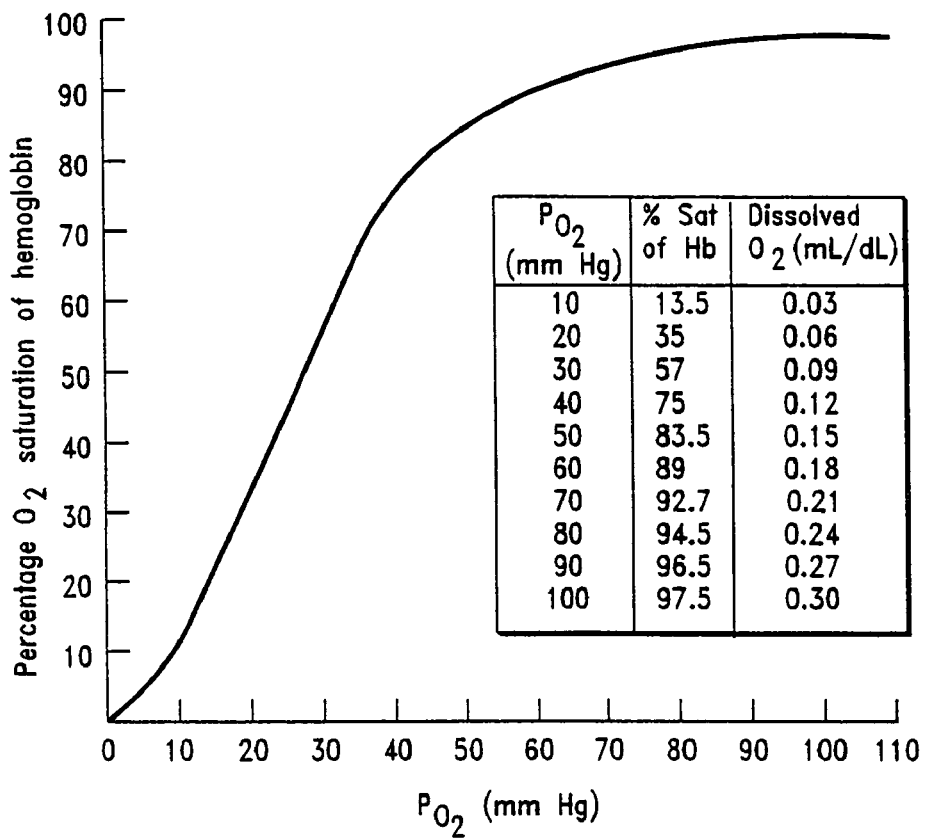
FIG. 38 is a graphical illustration of a normal hemoglobin-oxygen dissociation curve (HODC)
Figure 39:
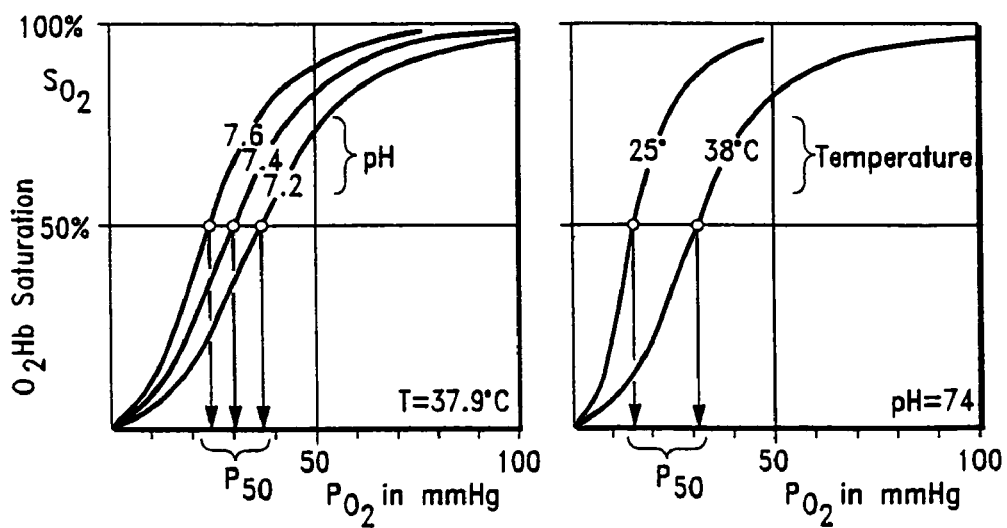
FIG. 39 is a graphical illustration of HODC's showing shifts due to pH and temperature.

These embodiments of the invention can be supplemented by considering the effect of temperature on the pH of blood. Temperature not only affects the hemoglobin oxygen dissociation curve, but has an independent effect on pH. FIG. 38 is a graph of the normal hemoglobin-oxygen dissociation curve (HODC). FIG. 39 shows the effect of temperature and pH on the HODC of FIG. 38. Thus, measurements of spectra can be taken at more that one temperature (and thus more than one pH), improving the accuracy of determinations. The Henderson-Hasselbach equation, describes the dissolution of an acid in terms of pH, pK (dissolution or dissociation constant), and the concentrations of the acid and its salt or base. The solubility, $\lambda$ of carbon dioxide ($CO_2$) is temperature-dependent and the pK for $CO_2$ also depends on temperature. Thus, for $CO_2$ the Henderson-Hasselbach equation becomes $pH=pK+\log([HCO_3]/\lambda PCO_2)$, or an alternate form can be used. The temperature dependence of the pK for carbonic acid is shown in Tables IIIA-IIIE below.

TABLE IIIA

| Temperature | PH | | | | | | | |
|---|---|---|---|---|---|---|---|---|
| | 7.6 | 7.59 | 7.58 | 7.57 | 7.56 | 7.55 | 7.54 | 7.53 |
| 40 | 6.07 | 6.0705 | 6.071 | 6.0715 | 6.072 | 6.0725 | 6.073 | 6.0735 |
| 39 | 6.07 | 6.0705 | 6.071 | 6.0715 | 6.072 | 6.0725 | 6.073 | 6.0735 |
| 38 | 6.08 | 6.0805 | 6.081 | 6.0815 | 6.082 | 6.0825 | 6.083 | 6.0835 |
| 37 | 6.08 | 6.0805 | 6.081 | 6.0815 | 6.082 | 6.0825 | 6.083 | 6.0835 |

TABLE IIIA-continued

| Temperature | PH | | | | | | | |
|---|---|---|---|---|---|---|---|---|
| | 7.6 | 7.59 | 7.58 | 7.57 | 7.56 | 7.55 | 7.54 | 7.53 |
| 36 | 6.09 | 6.0905 | 6.091 | 6.0915 | 6.092 | 6.0925 | 6.093 | 6.0935 |
| 35 | 6.1 | 6.1005 | 6.101 | 6.1015 | 6.102 | 6.1025 | 6.103 | 6.1035 |
| 33 | 6.1 | 6.1005 | 6.101 | 6.1015 | 6.102 | 6.1025 | 6.103 | 6.1035 |
| 30 | 6.12 | 6.1205 | 6.121 | 6.1215 | 6.122 | 6.1225 | 6.123 | 6.1235 |

TABLE IIIB

| Temperature | PH | | | | | | | |
|---|---|---|---|---|---|---|---|---|
| | 7.52 | 7.51 | 7.5 | 7.49 | 7.48 | 7.47 | 7.46 | 7.45 | 7.44 |
| 40 | 6.074 | 6.0745 | 6.075 | 6.0755 | 6.076 | 6.0765 | 6.077 | 6.0775 | 6.078 |
| 39 | 6.074 | 6.0745 | 6.075 | 6.0755 | 6.076 | 6.0765 | 6.077 | 6.0775 | 6.078 |
| 38 | 6.084 | 6.0845 | 6.085 | 6.0855 | 6.086 | 6.0865 | 6.087 | 6.0875 | 6.088 |
| 37 | 6.084 | 6.0845 | 6.085 | 6.0855 | 6.086 | 6.0865 | 6.087 | 6.0875 | 6.088 |
| 36 | 6.094 | 6.0945 | 6.095 | 6.0955 | 6.096 | 6.0965 | 6.097 | 6.0975 | 6.098 |
| 35 | 6.104 | 6.1045 | 6.105 | 6.1055 | 6.106 | 6.1065 | 6.107 | 6.1075 | 6.108 |
| 33 | 6.104 | 6.1045 | 6.105 | 6.1055 | 6.106 | 6.1065 | 6.107 | 6.1075 | 6.108 |
| 30 | 6.124 | 6.1245 | 6.125 | 6.1255 | 6.126 | 6.1265 | 6.127 | 6.1275 | 6.128 |

TABLE IIIC

| Temperature | PH | | | | | | | |
|---|---|---|---|---|---|---|---|---|
| | 7.43 | 7.42 | 7.41 | 7.4 | 7.39 | 7.38 | 7.37 | 7.36 | 7.35 |
| 40 | 6.0785 | 6.079 | 6.0795 | 6.08 | 6.0805 | 6.081 | 6.0815 | 6.082 | 6.0825 |
| 39 | 6.0785 | 6.079 | 6.0795 | 6.08 | 6.0805 | 6.081 | 6.0815 | 6.082 | 6.0825 |
| 38 | 6.0885 | 6.089 | 6.0895 | 6.09 | 6.0905 | 6.091 | 6.0915 | 6.092 | 6.0925 |
| 37 | 6.0885 | 6.089 | 6.0895 | 6.09 | 6.0905 | 6.091 | 6.0915 | 6.092 | 6.0925 |
| 36 | 6.0985 | 6.099 | 6.0995 | 6.1 | 6.1005 | 6.101 | 6.1015 | 6.102 | 6.1025 |
| 35 | 6.1085 | 6.109 | 6.1095 | 6.11 | 6.1105 | 6.111 | 6.1115 | 6.112 | 6.1125 |
| 33 | 6.1085 | 6.109 | 6.1095 | 6.11 | 6.1105 | 6.111 | 6.1115 | 6.112 | 6.1125 |
| 30 | 6.1285 | 6.129 | 6.1295 | 6.13 | 6.1305 | 6.131 | 6.1315 | 6.132 | 6.1325 |

TABLE IIID

| Temperature | PH | | | | | | | |
|---|---|---|---|---|---|---|---|---|
| | 7.34 | 7.33 | 7.32 | 7.31 | 7.3 | 7.29 | 7.28 | 7.27 | 7.26 |
| 40 | 6.083 | 6.0835 | 6.084 | 6.0845 | 6.085 | 6.0855 | 6.086 | 6.0865 | 6.087 |
| 39 | 6.083 | 6.0835 | 6.084 | 6.0845 | 6.085 | 6.0855 | 6.086 | 6.0865 | 6.087 |
| 38 | 6.093 | 6.0935 | 6.094 | 6.0945 | 6.095 | 6.0955 | 6.096 | 6.0965 | 6.097 |
| 37 | 6.093 | 6.0935 | 6.094 | 6.0945 | 6.095 | 6.0955 | 6.096 | 6.0965 | 6.097 |
| 36 | 6.103 | 6.1035 | 6.104 | 6.1045 | 6.105 | 6.1055 | 6.106 | 6.1065 | 6.107 |
| 35 | 6.113 | 6.1135 | 6.114 | 6.1145 | 6.115 | 6.1155 | 6.116 | 6.1165 | 6.117 |
| 33 | 6.113 | 6.1135 | 6.114 | 6.1145 | 6.115 | 6.1155 | 6.116 | 6.1165 | 6.117 |
| 30 | 6.133 | 6.1335 | 6.134 | 6.1345 | 6.135 | 6.1355 | 6.136 | 6.1365 | 6.137 |

TABLE IIIE

| Temperature | PH | | | | | |
|---|---|---|---|---|---|---|
| | 7.25 | 7.24 | 7.23 | 7.22 | 7.21 | 7.2 |
| 40 | 6.0875 | 6.088 | 6.0885 | 6.089 | 6.0895 | 6.09 |
| 39 | 6.0875 | 6.088 | 6.0885 | 6.089 | 6.0895 | 6.09 |
| 38 | 6.0975 | 6.098 | 6.0985 | 6.099 | 6.0995 | 6.1 |
| 37 | 6.0975 | 6.098 | 6.0985 | 6.099 | 6.0995 | 6.1 |

TABLE IIIE-continued

| Temperature | PH | | | | | |
|---|---|---|---|---|---|---|
| | 7.25 | 7.24 | 7.23 | 7.22 | 7.21 | 7.2 |
| 36 | 6.1075 | 6.108 | 6.1085 | 6.109 | 6.1095 | 6.11 |
| 35 | 6.1175 | 6.118 | 6.1185 | 6.119 | 6.1195 | 6.12 |
| 33 | 6.1175 | 6.118 | 6.1185 | 6.119 | 6.1195 | 6.12 |
| 30 | 6.1175 | 6.118 | 6.1185 | 6.119 | 6.1195 | 6.12 |

Since $[TCO_2]$ is very close to the sum of $[HCO_3^-]$ and $\lambda PCO_2$, $[HCO_3^-]=[TCO_2]-\lambda PCO_2$, then:

$$pH = pK + \log(([TCO_2] - \lambda PCO_2)/\lambda PCO_2) \qquad \text{Eq. 96}$$

The degree of shift of the HODC can be calculated by:

$$\text{temperature factor} = \text{antilog}\{0.024*(37-\text{temperature})\} \qquad \text{Eq. 97}$$

$$\text{pH factor} = \text{antilog}\{0.48*(pH-7.40)\} \qquad \text{Eq. 98}$$

$$\text{base excess factor} = \text{antilog}\{-0.0013*\text{base excess}\} \qquad \text{Eq. 99}$$

Calculation of blood oxygen content can be made as follows:

content (ml $O_2$/dl)=$THb$(g/dl)*502*1.38(ml $O_2$/g $HbO_2$)+0.003*$PO_2$  Eq. 100

Conversion of $PO_2$ to $SO_2$ (and of $SO_2$ to $PO_2$) is done using modifications of Adair's equation or Kehman's computation:

$$SO_2 = (25*(0.0257*PO_2 + 2*0.00075*PO_2^2 +$$
$$3*0.00000444*PO_2^3 + 4*0.00000255*PO_2^4)/$$
$$(1 + 0.0257*PO_2 + 0.00078*PO_2^2 +$$
$$0.00000444*PO_2^3 + 0.00000255*PO_2^4))$$   Eq. 101

Calculation of base excess can be done by the following formula, or other known means:

base excess=(1−0.0143*Hb)*([$HCO_3^-$]−24)  Eq. 102

These calculations and conversions represent approximate values as understood by those of skill in the art and the invention is not limited to them. As improved estimations become available, they may be used with the methods of the invention. Accordingly, alterations of this algorithm will be suggested to those skilled in the art, and are meant to be included within the scope and spirit of this application.

Alternatively, values for $PCO_2$ and bicarbonate can be computed without the use of temperature perturbation if the pH is known at two or more values. For example, techniques described elsewhere in this application show that we can perform simultaneous measurements for arterial and venous blood. The two compartments have the same temperature but different pH values, and this allows formation of the Henderson-Hasselbach formulation into two equations for two unknowns: $PCO_2$ and [$HCO_3^-$].

(D-6). Determination of Temperature

The shifts in the HODC shown in FIG. 39 relative to the curve shown in FIG. 38 are caused primarily by two factors: pH and temperature. Thus, the pH of two samples of blood at the same temperature will define which curve the blood is at, and thus what the temperature of the blood is. The techniques described elsewhere in this application can be used to provide simultaneous determinations of arterial and venous blood pH within a probe. As these pH values will be slightly different, the HODC can be defined, and temperature calculated quite accurately. This method of the invention gives a true, noninvasive measurement of blood temperature. Since the blood flow to the finger or other member within the probe is continuously refreshed, the measurement is a very accurate estimate of central or "core" temperature.

(D-7). Determination of Glucose Concentration

Most substances in blood are present in essentially the same concentration in arterial and venous blood. However, this is not true for substances that are consumed in significant quantities in the metabolic process. The most prominent of these are oxygen and glucose. This is especially true when dealing with molar quantities, as in spectrophotometry. The technique for determining venous oxygen saturation has been described above. Once both arterial and venous saturation are determined, their absorbances can be "normalized". This can also be performed for pH, as above. A subtraction of hemoglobin absorbance may then be performed, effectively removing it. What remains is the absorbance due to non-hemoglobin absorbers. This provides an estimation of glucose concentration since the largest non-hemoglobin absorber is glucose.

Additionally, the absorbance at each wavelength can be compared for arterial and venous blood. A vast majority of the non-hemoglobin absorbers, but not glucose, will be of the same concentration in both arterial and venous blood. By subtracting out the constant absorbance between arterial and venous blood, the remaining glucose absorbance can be measured, and glucose concentration can be accurately determined.

(D-8). Determination of Chemical Analytes

Once the concentration of hemoglobin is known, the concentration of many substances in blood could be determined as ratios of the concentration of hemoglobin. The use of multiple wavelengths will allow differentiation between molecules, and comparison can be made to concentration of hemoglobin even without knowledge of path length. A further embodiment of the invention establishes standards by creating layers or films containing known amounts of analytes of interest. These can then be compared optically with the changes due to blood volume shifts within a probe. Such techniques are not possible with conventional pulse oximetry as the signal from the film would simply be filtered out with all other unchanging (DC) signal. This invention overcomes this drawback by using venous measurements, and thus does not require limitation to pulsatile (AC) signal.

One exemplary method includes the steps of placing a film that contains a known concentration of an analyte within a probe system, such as one configured for a finger. The absorbance of the finger plus film system is measured for a given number of wavelengths of light. The blood volume of the finger is changed by raising or lowering it with respect to the heart (as outlined elsewhere in this application). As it can be assumed that the change in absorbance is due to change in blood volume, one can compare blood absorbance to film absorbance, and hence relative concentration of the analyte in blood to that in the film. Sufficient wavelengths must be examined to provide specificity for the analyte in question, as there are many potential absorbers in blood.

(D-9). Determination of Congenital Heart Disease and Anatomic Anomalies

Diagnosis of many disorders with anatomic anomalies can be made by the detection of unexpected propagation times, and abnormal propagation delays between right- and left-sided organs. The ability to measure both arterial and venous saturation, as well as arterial and venous pressures, can aid further in investigations.

For example, coarctation of the aorta is a common congenital abnormality. It is a narrowing or constriction of the thoracic aorta. It can occur before or after the origin of the left subclavian artery. In either case, the blood pressure will be much lower in the legs than the arms. Because of the constriction, both pressure and flow waves will be greatly delayed in the lower limbs as compared to the upper. If a child has a coarctation proximal to the origin of the left subclavian artery, there will be a significant discrepancy in the pulse and flow wave arrival times of the two arms, with the right preceding the left.

(D-10). Determination of Dysrhythmias

By measuring blood pressure and the electrocardiogram simultaneously, the diagnosis of dysrhythmias can be aided greatly. Both arterial and venous pressure are recorded simultaneously with the ECG, allowing differentiation of atrial vs. ventricular arrhythmias as well as correlation to Q-T interval.

It can be difficult to distinguish dysrhythmias of atrial conduction from those of ventricular conduction. However, these often manifest much different hemodynamic effects. Those with normal ventricular conduction and eject often maintain cardiac output and blood pressure closer to normal.

(D-11). Determination of Additional Cardiovascular Parameters

By measuring blood pressure and the electrocardiogram simultaneously, many additional parameters, such as systolic and diastolic pressure time indices, can be determined. An enormous amount of information can be gleaned from the use of probes on opposite sides of the body combined with hydrostatic perturbations. The time of arrival of a pulse to paired members is different, but the velocity of the pulse is also different. Examination of pulse propagation time, pulse propagation phase or delay, pulse velocity, and pulse amplitude gives four parameters that may change in different ways for each perturbation. Circuitry such as that shown in FIG. 13, is suitable for use in such embodiments. In one embodiment, raising and lowering an arm by the same amount may give different changes. Raising and lowering the other arm by the same amount may give still different changes. In an alternative embodiment, raising an arm by a given amount, then raising again by the same amount, may give different changes. Raising the other arm by the given amount, then raising again by the same amount, may give still different changes. Similarly measurement can be taken for lowering.

(D-12). Determination of Aortic Pressure

Using the methods and probes of the invention allows the aortic pressure to be determine and the reconstruction of the aortic pressure curve. This can be accomplished through fluid mechanics or changing the reflection wave from the lower extremities. Details of exemplary techniques may be found in U.S. Pat. Nos. 5,265,011, 5,882,311, and 6,010,457 which are hereby incorporated by reference thereto.

(D-13). Determination of Carotid Stenosis

The carotids are paired arteries running from the chest through the neck to the head, and provide the major source of blood supply to the head and brain. As they have different origins, they have different path lengths for pulse transmission and blood flow from the heart. A significant discrepancy in pulse and flow wave velocity in one carotid artery as compared to the other, or in paired arteries arising from the carotids (such as the facial arteries) suggest a stenosis on the side exhibiting the delay.

(D-14). Determination of Peripheral Vascular Disease

Peripheral vascular disease results in narrowing of the lumen of peripheral arteries, most commonly the large arteries of the leg. Because of this stenosis, the blood flow characteristics of the artery affected are altered, and thus the pulse and flow waves distal to the obstruction. If a probe is placed distal to the obstruction, significant delays will be noted. Again, this is best done when compared to a paired organ; for example, placing probes on the great toes of both feet to compare the wave characteristics of the arteries of the two legs.

(D-15). Determination of Compartment Syndrome

Compartment syndrome is hypoperfusion and resulting ischemia of a body member, commonly an arm or a leg, secondary to swelling caused by tissue damage. If the swelling is significant, the increased volume of the tissue may increase the pressure in the limb (compartment) to such an extent that it cuts off the arterial blood supply. This can be monitored by placing a probe distal to the compartment to measure the pulse and flow wave velocities. This is done preferably with a paired organ to compare the two. Slowing of the pulse wave and increase in the arrival time signal diminishing blood pressure within the compartment, which can eventually result in ischemia and gangrene if steps are not taken to relieve the pressure, normally with surgery.

(D-16). Determination of Autonomic Activity Sedation and Depth of Anesthesia

There are normal variations in pulse baseline, pulse amplitude, and beat-to-beat variability. These factors are thought to be indicative of autonomic nervous activity or "tone". All these factors can be measured by the device and techniques of the invention. An alternative embodiment invention can also be used as a monitor of autonomic activity, sedation, or "depth of anesthesia".

(D-17). Determination of Heart Rate

According to the invention, heart rate can be determined by counting the pulsatile arterial signal for a known length of time, or by the ECG impulse.

(D-18). Determination of Respiratory Rate

The impedance changes of the chest due to filling and emptying can be measured from the electrocardiogram tracing. During normal breathing, negative pressure is created within the chest by lowering of the diaphragm and expansion of the rib cage. This negative pressure causes blood to empty more rapidly from the peripheral into the central veins. This is also the case when respiration is assisted by a negative-pressure device such as the "iron lung".

During modern mechanically-assisted ventilation (with "ventilators"), positive pressure is created within the chest by forcing air into the lungs. For both positive- and negative-pressure ventilation, expiration is passive. This respiratory variation by itself can be used as an estimate of cardiac filling, giving left heart pressures. This determination can be assisted by the use of the hydrostatic techniques described above.

(D-19). Determination of EEG and EMG

Just as leads capable of detecting and transmitting electrocardiogram (ECG) signals can be included in the probes (as outlines elsewhere in this application), similar techniques will allow monitoring of the electroencephalogram (EEG) and electromyogram (EMG).

(D-20). Determination of Cardiac Ejection Fraction

This determination is made based upon the rate of change of saturation. If blood in a container is of a stable, known saturation, and blood of a different saturation is added, the rate of change is dependent on two things: the saturation of the blood being added, and the amount of blood that is flowing in (equivalent to blood flowing out). The stroke volumes of the right and left ventricles must be the same, so the inflow per heartbeat to the left ventricle must be the same as the outflow. While the saturation of blood flowing from the lungs to the left heart may not be precisely known, it will quickly equilibrate. This equilibration process allows the determination of ejection fraction to be made.

The saturation of the blood in the left side of the heart, specifically the left ventricle, is completely dependent on the oxygenation of the blood pumped into the lung by the right ventricle. The blood pumped by the left ventricle into the arterial tree maintains its saturation until it reaches the capillary beds of the organs. The blood returning to the right heart is a combination of widely varying saturations (due to the greatly differing extractions of the various organs). However, the blood pumped by the right ventricle equilibrates over the vast capillary network of the lungs. Furthermore, any differences in saturation of blood in the pulmonary venous system are thoroughly mixed in the left atrium and left ventricle.

Breathing an oxygen-enriched gas mixture will change the alveolar concentration of oxygen. A single deep breath after exhalation may be the preferred method. While healthy subjects can inhale a vital capacity (VCII) breath of near total lung capacity (TLC), one cannot expect this of all patients. However, it is not necessary to know the precise oxygen level in the lungs. All that is necessary is to induce a change in saturation. This works well for the determination, as it is much easier to produce saturation change in disease states, because the patient starts farther away from the maximum value of 100%. Preferably, this may be achieved through a breath-hold after the inspiration. Wash-out can be accounted for (one knows that the inspired gas is air), however, this complicates the otherwise simple mathematics. The breath holding is required for only several heartbeats, normally only a few seconds.

Even with holding one's breath, oxygen levels within the lung drop due to absorption by blood. However, even with high hemoglobin levels, the normal amount of oxygen carried by blood is about 20 cc/dL, and, as mixed venous saturation is normally about 75%, only about 5 cc/dL are taken up. Given a cardiac stroke volume of 100 cc (higher than normal), this is only 5 cc per heartbeat. A small breath will provide enough oxygen for several heartbeats, which should be all that is required.

Thus, an approximation is made that the concentration of oxygen in the lungs after oxygen inhalation is stable for several heartbeats. The first heartbeat after the inhalation will result in blood of a changed saturation entering the left heart from the lungs (may be 2nd heartbeat, accounting for "dead space" of the pulmonary veins). This will mix with the blood remaining from the last cardiac ejection. This remaining blood is the end-systolic volume of the left ventricle. It is the end-dastolic volume minus the stroke volume. The saturation of the blood in the left ventricle after mixing is between that of the end-systolic blood and the fresh blood from the lungs. The saturation of the mixed blood is measured after it is ejected to the periphery. The arrival of the blood at the periphery can be judged by the change in saturation from the baseline measurement. The saturation rises depending on the ratio of end-systolic blood to stroke volume. The higher the stroke volume, the faster the change in saturation. This can be looked at as either a "wash in" or "wash out" function.

Figure 40:
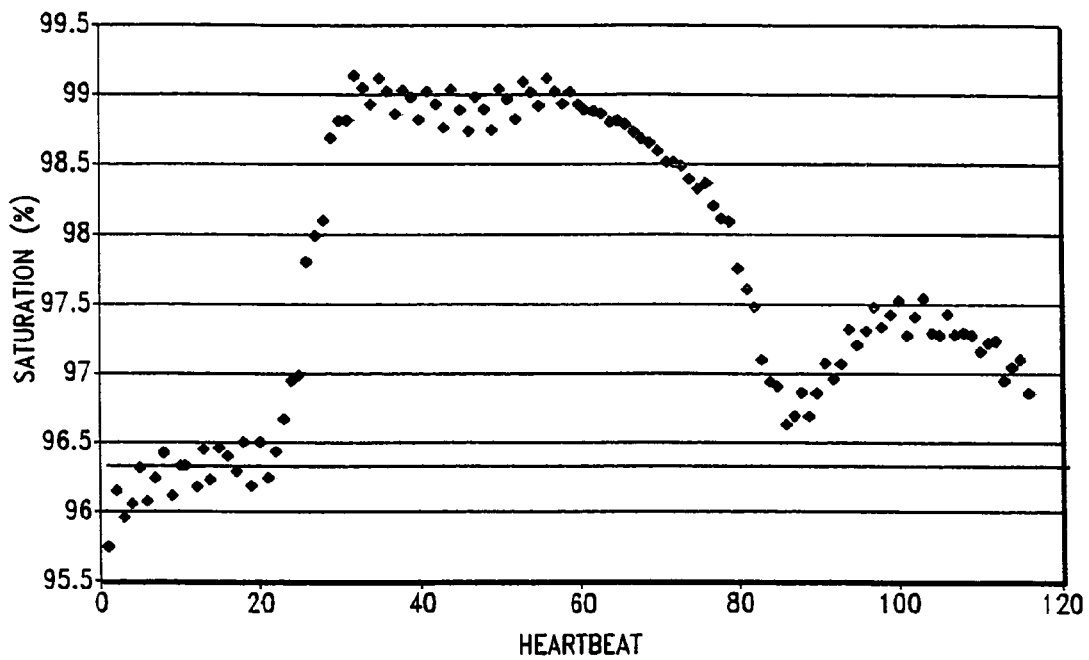
FIG. 40 is a graphical illustration of oxygen saturation versus heart rate showing the change of oxygen saturation corresponding to high cardiac fraction ejection.
Figure 41:
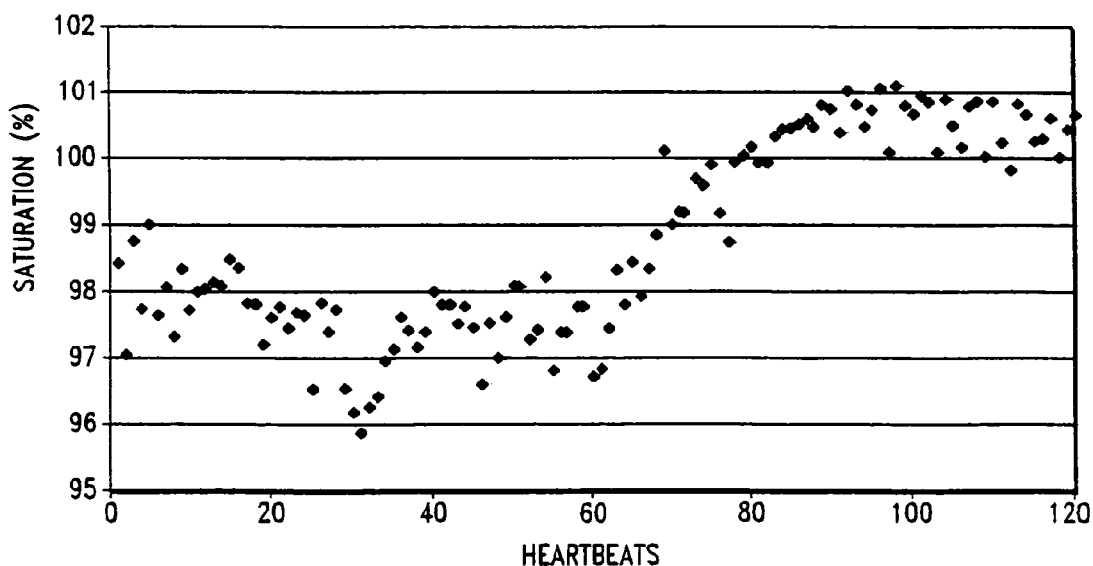
FIG. 41 is a graphical illustration of oxygen saturation versus heart rate showing a change of oxygen saturation corresponding to low cardiac fraction ejection.

Thus, a high ejection fraction results in a rapid change in saturation as shown in FIG. 40. The rapid change is represented by the relatively steep slope of the plot. In contrast, a low ejection fraction causes a slow change in saturation as shown in FIG. 41. Correspondingly, the slow change is represented by a relatively shallow slope of the plot. The exact same physiologic process reveals information about the cardiac output. As blood leaves the left ventricle, it travels to the aorta and then to the periphery. Just as the pulse arrives at different points of the body at different times, so does the blood flow from a given heartbeat. The blood travels much more slowly than the pulse wave, so the time delays are much greater. The change in oxygen saturation produces identifies the blood from individual beats to trace its arrival time to different parts of the body. By placing pulse oximeter probes at different points of the body (a finger and a toe, for example) and continuously monitoring saturation, the saturation change produced by the oxygen inhalation will occur in all parts of the arterial tree, but at different time intervals. The timing and ratio of these intervals is determined by the cardiac output—the longer the arrival time of the saturation change (and the greater the interval between finger and toe), the lower the cardiac output. Conversely, the shorter the arrival time of the saturation change (and the shorter the interval between finger and toe), the higher the cardiac output. Note that it is not necessary to maintain a breath-hold through the measurement since only a change in saturation is required.

An exemplary determination of cardiac ejection fraction starts with baseline saturation and saturation increasing because of inhalation of oxygen-rich gas:

Let dS be change in saturation S.

After 1 time constant, dS will have risen to approximately 63% of its final value.

After 2 time constants, dS will have risen to approximately 86.5% of its final value.

After 3 time constants, dS will have risen to approximately 95% of its final value.

After 5 time constants, dS will have risen to approximately 99% of its final value.

If the resting ("control") saturation is 95%, and it rises to 99% after oxygenation, total dS is 4.0%. Thus, 1 time constant is 0.63*4.0=2.52 percent, for a saturation value of 95.0+2.5=97.5%.

2 time constants are 0.865*4.0=3.46 percent, for a saturation value of 95.0+3.46=98.5%.

3 time constants are 0.95*4.0=3.80 percent, for a saturation value of 95.0+3=98.8%.

5 time constants are 0.99*4.0=3.96 percent, for a saturation value of 95.0+2=98.96%.

For this system, the time constant is the number of heartbeats that it would take to fill the ventricle from the empty state, or empty the ventricle from the full state. For example, an ejection fraction of 50% implies two heartbeats to fill or empty the ventricle, so the time constant is 2 beats. An EF of 80% implies a time constant of 1.25 beats, although this might be expressed more physiologically as 5 heartbeats are 4 time constants. A "worst case" scenario of an EF around 20% corresponds to a time constant of 5 heartbeats. Clinically, some type of calibration may be required, as actual measurements may not correspond exactly to these theoretical values.

It is expected that a minimum of 2 time constants are required to produce a satisfactory measurement, so an EF 20% would take 10 or more heartbeats. However, there is the trade-off in that there are more beats to analyze, so the curve can be fitted more precisely. Thus, it should be possible in almost all cases to produce an accurate determination within a few heartbeats after noting the saturation change.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A method for noninvasively determining physiological parameters of a patient, comprising the steps of:

providing a first tissue probe, said first tissue probe including a first radiation emitter adapted to emit first radiation having a first wavelength and a first radiation detector adapted to receive said first radiation after absorbance through a first radiation path length of the patient's blood;

providing a second tissue probe, said second tissue probe including a second radiation emitter adapted to emit second radiation having a second wavelength and a second radiation detector adapted to receive said second radiation after absorbance through a second radiation path length;

varying the volume and pressure of the patient's blood at first and second patient sites, said first patient site being proximate said first tissue probe, said second patient site being proximate second tissue probe;

measuring first absorbance of the patient's blood at said first patient site as said blood volume and pressure are varied by transmitting said first radiation at said first wavelength through the patient's blood and detecting said first radiation after passage through the patient's blood;

measuring second absorbance of the patient's blood at said second patient site as said blood volume and pressure are varied by transmitting said second radiation at said second wavelength through the patient's blood and detecting said second radiation after passage through the patient's blood;

timing the arrival of pulse and flow waves at said first and second patient sites by comparing said first and second absorbances measured at said first and second patient sites; and determining a cardiac characteristic based on said arrival times of said pulse and flow waves.

2. The method of claim 1, further comprising the step of measuring the electrical potential of the patient's heart using an electrocardiogram, said electrocardiogram providing an ECG signal, and correlating said timing of said first and second absorbances with said ECG signal.

3. A method for non-invasively determining a cardiac characteristic of a patient, comprising the steps of:

determining pulse wave velocity in a first extremity;

determining pulse wave velocity in a second, opposite extremity;

determining flow wave velocity as a function of ratios of said pulse wave velocities in said first and second extremities; and determining at least one cardiac output characteristic based on said flow wave velocity.

4. The method of claim 3, wherein said cardiac characteristic is selected from the group comprising cardiac output, cardiac index, cardiac stroke volume, cardiac ejection fraction, and blood volume.

5. The method of claim 3, wherein said steps of measuring pulse wave velocity in said first and second extremities comprises measuring arrival times of pulse waves in said first and second extremities.

6. The method of claim 3, further comprising the step of measuring blood pressure and, wherein said flow wave velocity is determined as a function of said blood pressure.

7. The method of claim 3, wherein the steps of measuring pulse wave velocity in said first and second extremities includes the steps of continuously monitoring oxygen saturation in the patient's blood in said first and second extremities and inducing a change in oxygen saturation in said first and second extremities.

8. The method of claim 7, wherein said cardiac characteristic is selected from the group comprising cardiac index, cardiac stroke volume and cardiac output, and wherein said cardiac characteristic is computed by determining a time interval between said induced change in oxygen saturation and a first measured change in oxygen saturation.

9. The method of claim 7, wherein said cardiac characteristic comprises cardiac ejection fraction, and wherein said cardiac ejection fraction is computed by determining the time interval between a first measured change in oxygen saturation and maximal change in oxygen saturation.

10. The method of claim 7, wherein said cardiac characteristic comprises blood volume, and wherein said blood volume is computed by determining a time interval between said induced change in oxygen saturation and a return to a baseline measured oxygen saturation.

* * * * *